United States Patent
De Kimpe et al.

(10) Patent No.: US 9,243,245 B2
(45) Date of Patent: Jan. 26, 2016

(54) MEANS AND METHODS FOR COUNTERACTING MUSCLE DISORDERS

(75) Inventors: Josephus Johannes De Kimpe, Utrecht (NL); Gerard Johannes Platenburg, Voorschoten (NL); Judith Christina Theodora Van Deutekom, Dordrecht (NL); Annemieke Aartsma-Rus, Hoofddorp (NL); Garrit-Jan Boudewijn Van Ommen, Amsterdam (NL)

(73) Assignees: Academisch Ziekenhuis Leiden, Leiden (NL); BioMarin Technologies B.V., Leiden (NL)

( * ) Notice: Subject to any disclaimer, the term of this patent is extended or adjusted under 35 U.S.C. 154(b) by 0 days.

(21) Appl. No.: 12/767,702

(22) Filed: Apr. 26, 2010

(65) Prior Publication Data
US 2011/0294753 A1    Dec. 1, 2011

Related U.S. Application Data

(63) Continuation of application No. PCT/NL2008/050673, filed on Oct. 27, 2008.

(60) Provisional application No. 61/000,670, filed on Oct. 26, 2007.

(30) Foreign Application Priority Data

Oct. 26, 2007    (EP) .................................... 07119351

(51) Int. Cl.
| | |
|---|---|
| A61K 48/00 | (2006.01) |
| C07H 21/02 | (2006.01) |
| C07H 21/04 | (2006.01) |
| A01N 45/00 | (2006.01) |
| C12N 15/113 | (2010.01) |
| A61K 31/56 | (2006.01) |
| A61K 31/57 | (2006.01) |
| A61K 38/17 | (2006.01) |
| A61K 31/7088 | (2006.01) |
| A61K 45/06 | (2006.01) |

(52) U.S. Cl.
CPC .............. *C12N 15/113* (2013.01); *A61K 31/56* (2013.01); *A61K 31/57* (2013.01); *A61K 31/7088* (2013.01); *A61K 38/1719* (2013.01); *A61K 45/06* (2013.01); *A61K 48/00* (2013.01); *C12N 2310/11* (2013.01); *C12N 2310/315* (2013.01); *C12N 2310/321* (2013.01); *C12N 2310/3233* (2013.01); *C12N 2320/33* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,418,139 A | 5/1995 | Campbell |
| 5,541,308 A | 7/1996 | Hogan et al. |
| 5,593,974 A | 1/1997 | Rosenberg et al. |
| 5,608,046 A | 3/1997 | Cook et al. |
| 5,627,263 A | 5/1997 | Ruoslahti et al. |
| 5,658,764 A | 8/1997 | Pergolizzi et al. |
| 5,741,645 A | 4/1998 | Orr et al. |
| 5,766,847 A | 6/1998 | Jackle et al. |
| 5,853,995 A | 12/1998 | Lee |
| 5,869,252 A | 2/1999 | Bouma et al. |
| 5,916,808 A | 6/1999 | Kole et al. |
| 5,962,332 A | 10/1999 | Singer et al. |
| 5,968,909 A | 10/1999 | Agrawal et al. |
| 5,976,879 A | 11/1999 | Kole et al. |
| 6,124,100 A | 9/2000 | Jin |
| 6,130,207 A | 10/2000 | Dean et al. |
| 6,133,031 A | 10/2000 | Monia et al. |
| 6,172,208 B1 | 1/2001 | Cook ........................... 536/23.1 |
| 6,172,216 B1 | 1/2001 | Bennett et al. |
| 6,210,892 B1 | 4/2001 | Bennett et al. .................... 435/6 |
| 6,251,589 B1 | 6/2001 | Tsuji et al. |
| 6,280,938 B1 | 8/2001 | Ranum et al. |
| 6,300,060 B1 | 10/2001 | Kantoff et al. |
| 6,322,978 B1 | 11/2001 | Kahn et al. |
| 6,329,501 B1 | 12/2001 | Smith et al. |
| 6,355,481 B1 | 3/2002 | Li et al. |
| 6,355,690 B1 | 3/2002 | Tsuji |
| 6,369,038 B1 | 4/2002 | Blumenfeld et al. |
| 6,379,698 B1 | 4/2002 | Leamon |
| 6,399,575 B1 | 6/2002 | Smith et al. |
| 6,514,755 B1 | 2/2003 | Ranum et al. |
| 6,623,927 B1 | 9/2003 | Brahmachari et al. |

(Continued)

FOREIGN PATENT DOCUMENTS

| | | |
|---|---|---|
| CA | 2319149 | 10/2001 |
| CA | 2526893 | 11/2004 |

(Continued)

OTHER PUBLICATIONS

Reiter et al (Brain Dev. 17(suppl): 39-43, 1995).*
Aartsma-Rus et al (A. J. Hum. Genet. 74: 83-92, 2004).*
Takeshima et al (Ped. Res. 39(3): 690-694, 2006).*
Politano et al (Acta Myologica 22: 15-21, 2003).*
Alter et al (Nature Med. 12(2): 175-177, 2006).*
Duboc et al (J. Am. Coll. Cardiol. 45(6): 2005).*
Rosen et al (Cancer 35: 622-630, 1975).*
O'Shaughnessy et al (Journal of Clinical Oncology, vol. 20, No. 12 Jun. 15, 2002).*

(Continued)

*Primary Examiner* — Richard Schnizer
(74) *Attorney, Agent, or Firm* — Sunstein Kann Murphy & Timbers LLP

(57) ABSTRACT

The invention provides means and methods for alleviating one or more symptom(s) of Duchenne Muscular Dystrophy and/or Becker Muscular Dystrophy. Therapies using compounds for providing patients with functional muscle proteins are combined with at least one adjunct compound for reducing inflammation, preferably for reducing muscle tissue inflammation, and/or at least one adjunct compound for improving muscle fiber function, integrity and/or survival.

22 Claims, 28 Drawing Sheets

(56) References Cited

U.S. PATENT DOCUMENTS

| | | | |
|---|---|---|---|
| 6,653,466 B2 | 11/2003 | Matsuo | |
| 6,653,467 B1 | 11/2003 | Matsuo et al. | |
| 6,670,461 B1 | 12/2003 | Wengel et al. | |
| 6,727,355 B2 | 4/2004 | Matsuo et al. | 536/24.5 |
| 6,794,192 B2 | 9/2004 | Parums et al. | |
| 6,902,896 B2 | 6/2005 | Ranum et al. | |
| 6,982,150 B2 | 1/2006 | Sheetz et al. | |
| 7,001,994 B2 | 2/2006 | Zhu | 536/4.1 |
| 7,118,893 B2 | 10/2006 | Ranum et al. | |
| 7,189,530 B2 | 3/2007 | Botstein et al. | |
| 7,202,210 B2 | 4/2007 | Wolfman et al. | |
| 7,250,404 B2 | 7/2007 | Felgner et al. | |
| 7,355,018 B2 | 4/2008 | Glass | 530/399 |
| 7,405,193 B2 | 7/2008 | Lodish et al. | 514/2 |
| 7,442,782 B2 | 10/2008 | Ranum et al. | 536/23.1 |
| 7,514,551 B2 | 4/2009 | Rabbani et al. | 536/26.6 |
| 7,534,879 B2 | 5/2009 | van Deutekom | 536/24.5 |
| 7,589,189 B2 | 9/2009 | Ichiro et al. | 536/24.5 |
| 7,655,785 B1 | 2/2010 | Bentwich | 536/24.1 |
| 7,771,727 B2 | 8/2010 | Fuselier et al. | 424/185.1 |
| 7,807,816 B2 | 10/2010 | Wilton et al. | 536/24.5 |
| 7,902,160 B2 | 3/2011 | Matsuo et al. | 514/44 |
| 7,960,541 B2 | 6/2011 | Wilton et al. | 536/24.5 |
| 8,232,384 B2 | 7/2012 | Wilton et al. | 536/24.5 |
| 8,324,371 B2 | 12/2012 | Popplewell et al. | 536/24.5 |
| 8,450,474 B2 | 5/2013 | Wilton et al. | 536/24.5 |
| 8,455,634 B2 | 6/2013 | Wilton et al. | 536/24.5 |
| 8,455,635 B2 | 6/2013 | Wilton et al. | 536/24.5 |
| 8,455,636 B2 | 6/2013 | Wilton et al. | 536/24.5 |
| 8,476,423 B2 | 7/2013 | Wilton et al. | 536/24.5 |
| 8,486,907 B2 | 7/2013 | Wilton et al. | 514/44 |
| 8,524,880 B2 | 9/2013 | Wilton et al. | 536/24.5 |
| 8,637,483 B2 | 1/2014 | Wilton et al. | 514/44 A |
| 2001/0056077 A1 | 12/2001 | Matsuo | |
| 2002/0049173 A1 | 4/2002 | Bennett et al. | |
| 2002/0055481 A1 | 5/2002 | Matsuo et al. | |
| 2002/0115824 A1 | 8/2002 | Engler et al. | |
| 2002/0165150 A1 | 11/2002 | Ben-Sasson | |
| 2003/0073215 A1 | 4/2003 | Baker et al. | |
| 2003/0082763 A1 | 5/2003 | Baker et al. | |
| 2003/0082766 A1 | 5/2003 | Baker et al. | |
| 2003/0109476 A1 | 6/2003 | Kmiec et al. | |
| 2003/0124523 A1 | 7/2003 | Asselbergs et al. | |
| 2003/0134790 A1 | 7/2003 | Langenfeld | |
| 2003/0235845 A1 | 12/2003 | van Ommen et al. | |
| 2003/0236214 A1 | 12/2003 | Wolff et al. | |
| 2004/0101852 A1 | 5/2004 | Bennett et al. | |
| 2004/0132684 A1 | 7/2004 | Sampath et al. | |
| 2004/0226056 A1 | 11/2004 | Roch et al. | |
| 2005/0096284 A1 | 5/2005 | McSwiggen | |
| 2005/0222009 A1 | 10/2005 | Lamensdorf et al. | |
| 2005/0246794 A1 | 11/2005 | Khvorova et al. | |
| 2005/0277133 A1 | 12/2005 | McSwiggen | |
| 2006/0074034 A1 | 4/2006 | Collins et al. | |
| 2006/0148740 A1 | 7/2006 | Platenburg | |
| 2007/0082861 A1 | 4/2007 | Matsuo et al. | |
| 2007/0141628 A1 | 6/2007 | Cunningham et al. | 435/7.1 |
| 2007/0275914 A1 | 11/2007 | Manoharan et al. | |
| 2007/0292408 A1 | 12/2007 | Singh et al. | 424/130.1 |
| 2008/0015158 A1 | 1/2008 | Ichiro et al. | 514/44 |
| 2008/0039418 A1 | 2/2008 | Freir | 514/44 |
| 2008/0113351 A1 | 5/2008 | Naito et al. | 435/6 |
| 2008/0207538 A1 | 8/2008 | Lawrence et al. | 514/41 |
| 2008/0249294 A1 | 10/2008 | Haeberli et al. | 536/24.5 |
| 2010/0081627 A1 | 4/2010 | Sampath et al. | 514/47 |
| 2010/0099750 A1 | 4/2010 | McSwiggen et al. | 514/44 R |
| 2011/0015253 A1 | 1/2011 | Wilton et al. | 514/44 A |
| 2011/0015258 A1 | 1/2011 | Wilton et al. | 514/44 R |
| 2011/0046203 A1 | 2/2011 | Wilton et al. | 514/44 A |
| 2011/0263686 A1 | 10/2011 | Wilton et al. | 514/44 A |
| 2012/0022144 A1 | 1/2012 | Wilton et al. | 514/44 A |
| 2012/0022145 A1 | 1/2012 | Wilton et al. | 514/44 A |
| 2012/0029057 A1 | 2/2012 | Wilton et al. | 514/44 A |
| 2012/0029058 A1 | 2/2012 | Wilton et al. | 514/44 A |
| 2012/0029059 A1 | 2/2012 | Wilton et al. | 514/44 A |
| 2012/0029060 A1 | 2/2012 | Wilton et al. | 514/44 A |
| 2012/0041050 A1 | 2/2012 | Wilton et al. | 514/44 A |
| 2013/0116310 A1 | 5/2013 | Wilton et al. | 514/44 A |
| 2013/0217755 A1 | 8/2013 | Wilton et al. | 514/44 A |
| 2013/0253033 A1 | 9/2013 | Wilton et al. | 514/44 A |
| 2013/0253180 A1 | 9/2013 | Wilton et al. | 536/24.5 |
| 2013/0274313 A1 | 10/2013 | Wilton et al. | 514/44 A |

FOREIGN PATENT DOCUMENTS

| | | | |
|---|---|---|---|
| EP | 438512 A1 | 7/1991 | |
| EP | 558697 | 9/1993 | |
| EP | 614977 A2 | 9/1994 | |
| EP | 850300 | 7/1998 | |
| EP | 1054058 | 5/2000 | |
| EP | 1015628 A1 | 7/2000 | |
| EP | 1133993 | 9/2001 | |
| EP | 1160318 | 12/2001 | |
| EP | 1191097 | 3/2002 | |
| EP | 1191098 | 3/2002 | |
| EP | 1380644 | 1/2004 | |
| EP | 1 487 493 A2 | 12/2004 | |
| EP | 1495769 | 1/2005 | |
| EP | 1501931 | 2/2005 | |
| EP | 1544297 | 6/2005 | |
| EP | 1567667 A1 | 8/2005 | |
| EP | 1568769 | 8/2005 | |
| EP | 1619249 | 1/2006 | |
| EP | 1857548 | 11/2007 | C12N 15/11 |
| KR | 20030035047 | 5/2003 | |
| WO | WO-9301286 A2 | 1/1993 | |
| WO | WO-95/16718 A1 | 6/1995 | |
| WO | WO-9530774 | 11/1995 | |
| WO | WO-9712899 | 4/1997 | |
| WO | WO-9730067 | 8/1997 | |
| WO | WO-9818920 A1 | 5/1998 | |
| WO | WO-9849345 A1 | 11/1998 | |
| WO | WO 98/53804 | 12/1998 | A61K 31/00 |
| WO | WO 00/24885 | 5/2000 | C12N 15/11 |
| WO | WO-0179283 A1 | 10/2001 | |
| WO | WO 01/83503 | 11/2001 | C07H 21/00 |
| WO | WO-0183695 | 11/2001 | |
| WO | WO-0202406 | 1/2002 | |
| WO | WO-0224906 | 3/2002 | |
| WO | WO-0226812 A1 | 4/2002 | |
| WO | WO-0229056 | 4/2002 | |
| WO | WO-03002739 | 1/2003 | |
| WO | WO-03/014145 A2 | 2/2003 | |
| WO | WO-03013437 | 2/2003 | |
| WO | WO-03037172 | 5/2003 | |
| WO | WO-03095647 | 11/2003 | |
| WO | WO-2004/011060 A2 | 2/2004 | |
| WO | WO-2004015106 | 2/2004 | |
| WO | WO-2004016787 | 2/2004 | |
| WO | WO 2004/037854 | 5/2004 | C07K 1/04 |
| WO | WO-2004048570 | 6/2004 | |
| WO | WO-2004083432 | 9/2004 | |
| WO | WO-2004083446 | 9/2004 | |
| WO | WO-2004101787 | 11/2004 | |
| WO | WO-2004108157 | 12/2004 | |
| WO | WO 2005/023836 | 3/2005 | |
| WO | WO-2005019453 A2 | 3/2005 | |
| WO | WO-2005035550 | 4/2005 | |
| WO | WO-2005085476 A1 | 9/2005 | |
| WO | WO-2005086768 | 9/2005 | |
| WO | WO-2005105995 A2 | 11/2005 | |
| WO | WO 2005/115439 | 12/2005 | C12N 15/85 |
| WO | WO 2005/115479 | 12/2005 | A61K 48/00 |
| WO | WO-2005115439 | 12/2005 | |
| WO | WO-2005116204 A1 | 12/2005 | |
| WO | 2006/007910 A1 | 1/2006 | |
| WO | WO-2006000057 | 1/2006 | |
| WO | WO-2006017522 | 2/2006 | |
| WO | WO-2006031267 | 3/2006 | |
| WO | WO-2006/054262 A2 | 5/2006 | |
| WO | WO-2006083800 | 8/2006 | |
| WO | WO-2006108052 | 10/2006 | |
| WO | WO-2006112705 | 10/2006 | |
| WO | WO-2006121960 A2 | 11/2006 | |

(56) References Cited

FOREIGN PATENT DOCUMENTS

| WO | WO 2007/004979 | 1/2007 | ............ A61K 38/00 |
| WO | WO-2007002904 A2 | 1/2007 | |
| WO | WO-2007044362 | 4/2007 | |
| WO | WO-2007089584 | 8/2007 | |
| WO | WO-2007089611 A2 | 8/2007 | |
| WO | WO 2007/135105 | 11/2007 | ............ C12N 15/11 |
| WO | WO-2007123402 | 11/2007 | |
| WO | WO 2008/011170 | 1/2008 | ............... C12Q 1/68 |
| WO | WO 2008/043561 | 4/2008 | ............ A61K 48/00 |

OTHER PUBLICATIONS

Abdel-Salam et al (Pharmacological Research 47 (2003) 331-340).*
Fernandez et al (Atherosclerosis 196 (2008) 434-442).*
Dorchies et al (Am J Physiol Cell Physiol 290: C616-C625, 2006).*
Chamberlain (Basic Appl Myol. 7 (3&4): 257-255, 7997).*
Kendall et al (Sci Transl Med 4, 164ra160 (2012)).*
Xu et al (Ann N Y Acad Sci. Sep. 16, 1998;853:130-48).*
Ryanodine receptor. Retrieved from http://en.wikipedia.org/wiki/Ryanodine_receptor on Jun. 6, 2014.*
Rolland et al (Neurobiology of Disease 24 (2006) 466-474.*
Aartsma-Rus et al. "Antisense Mediated exon skipping; A Versatile Tool with Therapeutic and Research Applications" RNA 2007 pp. 1609-1624 vol. 13 No. 10.
Aartsma-Rus et al. Antisense-Induced Exon Skipping for Duplications in Duchenne Muscular Dystrophy Jul. 5, 2007 BMC Med. Genet. 8:43.
Aartsma-Rus et al. Therapeutic Modulation of DMD splicing by Blocking Exonic Splicing Enhancer Sites with Antisense Oligonucleotides Ann NY Acad Sci 2006 pp. 74-76 vol. 1082.
Aartsma-Rus, et al., "Functional Analysis of 114 Exon-Internal AONs for Targeted DMD Exon Indication for Steric Hindrance of SR Protein Binding Sites," Oligonucleotides, 2005, pp. 284-297, vol. 15.
Aartsma-Rus, et al., Antisense-Induced Multiexon Skipping for Duchenne Muscular Dystrophy Makes More Sense, Am. J. Hum. Genet, 2004 pp. 83-92, vol. 74.
Aartsma-Rus, et al., Exploring the Frontiers of Therapeutic Exon Skipping for Duchenne Muscular Dystrophy by Double Targeting within One or Multiple Exons, Molecular Therapy, 2006, pp. 1-7.
Aartsma-Rus, et al., Targeted exon skipping as a potential gene correction therapy for Duchenne muscular dystrophy, Neuromuscular Disorders, 2002, S71-S77, vol. 12.
Aartsma-Rus, et al., Therapeutic antisense-induced exon skipping in cultured muscle cells from six different patients, Human Molecular Genetics, 2003, pp. 907-914, vol. 12, No. 8.
Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.
Agrawal and Kandimalla, et al., "Antisense therapeutics: is it as simple as complementary base recognition?" Mol. Med. Today, Feb. 2000, vol. 6., pp. 72-81.
Arzumanov, et al. Inhibition of HIV-1 Tat-dependent trans activation by steric block chimeric 2'-O-methyl/LNA oligoribonucleotides. Biochemistry, 2001, vol. 40, pp. 14645-14654.
Austin et al. "Cloning and characterization of alternatively spliced isoforms of Dp71." Hum Mol Genetics 1995 vol. 4 No. 9 1475-1483.
Australian Office Action for AU 2009240879, dated Jun. 22, 2011.
Barabino et al. (1992) "Antisense probes targeted to an internal domain in US snRNP specifically inhibit the second step of pre-mRNA splicing" Nucleic Acids Res. 20(17):4457-4464.
Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.
Biopharmaceutiques, Merging Pharma & Biotech, Edition 48, Jan. 10, 2008. <http://www.biopharmaceutiques.com/en/num>, visited Jan. 11, 2008.
Bremmer-Bout, et al., Targeted exon skipping in transgenic hDMD mice: A model for direct preclinical screening of human-specific antisense oligonucleotides. Mol Ther. Aug. 2004; 10(2):232-40.
Brett et al., EST comparison indicates 38% of human m RNAs contain possible alternative splice forms. FEBS Lett 474(1): 83-86.
Brown, et al., "Structure and mutation of the dystrophin gene" in Dystrophin: Gene, protein and cell biology, (Brown and Lucy, eds). Cambridge University Press, Cambridge, 1997, pp. 1-16.
Canadian Office Action for CA 2,524,255, dated Jul. 6, 2011.
Cartegni, et al., Abstract, Listening to silence and understanding nonsense: exonic mutations that affect splicing, Nature Reviews Genetics, Apr. 2002, pp. 285-298, vol. 3.
Coulter et al. Identification of a new class of exonic splicing enhancers by in vivo selection. Mol. Cell. Biol. 17(4) 2143-50 (1997).
Crooke. In Basic Principles of Antisense Therapeutics, Springer-Verlag, Eds, New York, 1998, pp. 1-50.
Dahlqvist, et al., "Functional notch signaling is required for BMP4-induced inhibition of myogenic differentiation," Development 130:6089-6099 (2003).
De Angelis, et al., Chimeric snRNA molecules carrying antisense sequences against the splice junctions of exon 51 of the dystrophin pre-mRNA exon skipping and restoration of a dystrophin synthesis in delta 48-50 DMD cells, PNAS, Jul. 9, 2002, pp. 9456-9461, vol. 99, No. 14.
Declaration of Dr. Adrian Krainer (submitted in Third Party's Stmt for JP Appl. No. 2002-529499, dated Oct. 29, 2010).
Dickson, et al., Screening for antisense modulation of dystrophin pre-mRNA splicing, Neuromuscul. Disord., 2002, S67-70, Suppl. 1.
Dirkson, et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.
Dunckley, et al., Modification of splicing in the Dsytrophin gene in cultured Mdx muscle cells by antisense oligoribonucleotides. Hum Mol Genet. 1995 7(7):1083-90.
Dunckley, et al., Modulation of Splicing in the DMD Gene by Antisense Oligoribonucleotides, Nucleosides & Nucleotides, 1997, pp. 1665-1668, vol. 16, No. 7-9.
Erba et al., Structure, chromosome location, and expression of the human gamma-actin gene: differential evolution, location, and expression of the cytoskeletal beta- and gamma-actin genes. Mol. Cell. Biology, 1988, 8(4):1775-89.
Errington, et al., Target selection for antisense oligonucleotide induced exon skipping in the dystrophin gene. J Gene Med. Jun. 2003; 5(6):518-27.
European Patent Office Action dated Jan. 29, 2007.
Feener et al., Alternative splicing of human dystrophin mRNA generates isoforms at the carboxy terminus. Nature, 338 (6215): 509-511 (1989).
Fluiter, K., "In Vivo tumor growth inhibition and biodistribution studies of locked nucleic acid (LNA) antisense oligonucleotides," Nucl. Acids Research 2003, vol. 31., No. 3., pp. 953-962.
Genes VII, Jan. 2000, Benjamin Lewin, Chapter 22, Nuclear Splicing, pp. 704-705.
Ginjaar, et al., Dystrophin nonsense mutation induces different levels of exon 29 skipping and leads to variable phenotypes within one BMD family, European Journal of Human Genetics (2000) 8, 793-796.
Grady, Promising Dystrophy Drug Clears Early Test, The New York Times, Dec. 27, 2007.
Gryaznov, "Oligonucleotide N3' → P5' phosphoramidates as potential therapeutic agents." Biochemistry et Biophys. Acta, 1999, vol. 1489, pp. 131-140.
Hagiwara, et al. "A novel point mutation (G-1 to T) in a 5' splice donor site of intron 13 of the dystrophin gene results in exon skipping and is responsible for Becker muscular dystrophy." Am J. Hum Genet. Jan. 1994;54(1):53-61.
Hoffman, Skipping toward Personalized Molecular Medicine, N. England J. Med., Dec. 27, 2007, pp. 2719-2722, vol. 357, No. 26.
Hope for muscular dystrophy drug, The Daily Telegraph, Dec. 28, 2007.
Hussey, et al., Analysis of five Duchenne muscular dystrophy exons and gender determination using conventional duplex polymerase chain reaction on single cells, Molecular Human Reproduction, 1999, pp. 1089-1094, vol. 5, No. 11.

(56) References Cited

OTHER PUBLICATIONS

Iezzi, et al. "Deacetylase inhibitors increase muscle cell size by promoting myoblast recruitment and fusion through induction of follistation," Development Cell 6:673-684 (2004).
International Preliminary Examination Report, International Application No. PCT/NL01/00697, dated Aug. 1, 2002.
International Search Report, International Application No. PCT/NL 2008/050470, dated Jul. 2, 2009.
International Search Report, International Application No. PCT/NL 2008/050475, dated Jun. 25, 2009.
International Search Report, International Application No. PCT/NL01/00697, dated Dec. 21, 2002.
International Search Report, International Application No. PCT/NL2004/000196, dated Oct. 28, 2004.
International Search Report, International Application No. PCT/NL2006/000209, dated Oct. 5, 2006.
Karras, et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.
Kerr, et al., "BMP Regulates Skeletal Myogenesis at Two Steps," Molecular Cellular Proteomics 2.9:976. 123.8 (2003) (Abstract Only).
Kurrek, et al., "Design of antisense oligonucleotides stabilized by locked nucleic acids." Nucleic Acids Research, 2002, vol. 30, No. 9, pp. 1911-1918.
Laptev et al., (1994) "Specific inhibition of expression of a human collagen gene (COL1A1) with modified antisense oligonucleotides. The most effective target sites are clustered in double-stranded regions of the predicted secondary structure for the mRNA" Biochemistry 33(36):11033-11039.
Lee et al., "Receptor mediated uptake of peptides that bind the human transferrin receptor", Eur. J. Biochem. 268, 2004-2012 (2001).
Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.
Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).
Letter from Prosensa Therapeutics B.V. to Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.
Liu et al., "A mechanism for exon skipping caused by nonsense or missense mutations in BRCA1 and other genes." Nat Genet. Jan. 2001;27(1):55-8.
Liu, et al., Identification of functional exonic splicing enhancer motifs recognized by individual SR proteins, Genes & Development, 1998, pp. 1998-2012, vol. 12.
Lu et al. Functional Amounts of Dystrophin Produced by Skipping the Mutated Exon in the MDX Dystrophic Mouse 2003 Nat Med 8: 1009-1014.
Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.
LUMC and Prosensa report positive results of DMD study, Pharmaceutical Business Review Online, dated Dec. 28, 2007, <http://www.pharmaceutical-business-review.com/article_news_printasp?guid=8462FD44-F35D-4EOB-BC>.
Mann, et al., Antisense-induced exon skipping and synthesis of dystrophin in the mdx mouse. Proc Natl Acad Sci USA Jan. 2, 2001: 98(1):42-7.

Mann, et al., Improved antisense oligonucleotide induced exon skipping in the mdx mouse model of muscular dystrophy. J Gene Med. Nov.-Dec. 2002:4(6):644-54.
Matsuo et al. (1992) "Partial deletion of a dystrophin gene leads to exon skipping and to loss of an intra-exon hairpin structure from the predicted mRNA precursor" Biochem. Biophys. Res. Commun. 182(2):495-500.
Matsuo, et al., "Duchenne/Becker muscular dystrophy: from molecular diagnosis to gene therapy." Brain Dev. (1996) 18(3):167-172.
McClorey et al. Induced Dystrophin Exon Skipping in Human Muscle Explants Neuromuscul Disord 2006 pp. 583-590 vol. 16 No. 9-10.
Monaco, et al., An Explanation for the Phenotypic Differences between Patients Bearing Partial Deletions of the DMD Locus, Genomics, 1988, pp. 90-95, vol. 2.
Moon, et. al., "Target site Search and effective inhibition of leukaemic cell growth by a covalently closed multiple anti-sense oligonucleotide to c-myb" The Biochemical Journal, Mar. 1, 2000, vol. 346 Pt 2, pp. 295-303.
Munroe (1988) "Antisense RNA inhibits splicing of pre-mRNA in vitro" EMBO J. 7(8):2523-2532.
Muntoni et al. "A Mutation in the Dystrophin Gene Selectively Affecting Dystrophin Expression in the Heart." J. Clin Invest. vol. 96 Aug. 1995. 693-699.
New Clinical Trial Results Show How Personalized Medicine Will Alter Treatment of Genetic Disorders, Medical News Today, Dec. 29, 2007 <http://www.medicalnewstoday.com/article/92777.php>.
Nishio, et al., Identification of a novel first exon in the human dystrophin gene and of a new promoter located more than 500 kb upstream of the nearest known promoter. (1994) J. Clin. Invest. 94:1037-1042.
Notice of Opposition filed against EP 1 619 249 B, dated Jun. 23, 2009.
Office Action for U.S. Appl. No. 10/395,031, dated Apr. 2, 2009.
Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.
Office Action for U.S. Appl. No. 10/395,031, dated May 30, 2008.
Office Action for U.S. Appl. No. 10/395,031, dated Nov. 30, 2006.
Office Action for U.S. Appl. No. 10/395,031, dated Oct. 16, 2009.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated May 29, 2009.
Office Action for U.S. Appl. No. 11/233,507, dated Nov. 12, 2008.
Office Action for U.S. Appl. No. 11/982,285, dated May 4, 2009.
Office Action for U.S. Appl. No. 11/982,285, dated Sep. 18, 2009.
Opalinska and Gewirtz. "Nucleic-acid therapeutics: basic principles and recent applications." Nature Reviews Drug Discovery, 2002, vol. 1, pp. 503-514.
Oxford Dictionary of English, 2nd Edition, Revised, Oxford University Press, p. 158.
Patel, et al., "The Function of Myostatin and strategies of Myostatin blockade—new hope for therapies aimed at promoting growth of skeletal muscle," Neuromuscular Disorders 15(2):117-126 (2005).
Patentee's response during prosecution of opposed patent, dated Jan. 27, 2010.
Pramono, et al., Abstract, Induction of Exon Skipping of the Dystrophin Transcript in Lymphoblastoid Cells by Transfecting an Antisense Oligodeoxynucleotide Complementary to an Exon Recognition Sequence, Biochemical and Biophysical Research Communications, Sep. 13, 1996, pp. 445-449, vol. 226, No. 2.
Rando, Thomas A., "Oligonucleotide-mediated gene therapy for muscular dystrophies." Neuromuscular Disorders, 2002, vol. 12, pp. S55-S60.
Request for an Opinion under Section 74(A) in relation to Patent No. EP (UK) 1 619 249B in the name of Academisch Ziekenhuis Leiden, opinion issued on Jun. 4, 2009.
Request for UK IPO Opinion (Section 74A & Rule 93)—EP(UK) 1619249 dated Mar. 9, 2009.

(56) References Cited

OTHER PUBLICATIONS

Roberts et al., Direct detection of dystrophin gene rearrangements by analysis of dystrophin mRNA in peripheral blood lymphocytes. Am. J. Hum. Genet. 49(2): 298-310 (1991).
Roberts, et al., "Exon structure of the human dystrophin gene." Genomics, 1993, vol. 16, No. 2, pp. 536-538. (1993).
Roberts, et al., Direct diagnosis of carriers of Duchenne and Becker muscular dystrophy by amplification of lymphocyte RNA. Lancet, 336 (8730-8731): 1523-6 (1990).
Roberts, et al., Searching for the 1 in 2,400,000: a review of dystrophin gene point mutations. Hum. Mut. 4:1-11 (1994).
Scanlon, "Anti-genes: siRNA, ribozymes, and antisense." Curr. Pharmaceutical Biotechnology, 2004, vol. 5, pp. 415-420.
Sertic, et al., "Deletion screening of the Duchenne/Becker muscular dystrophy gene in Croatian population" Coll. Antropol. 1997, 1:151-156.
Shapiro and Senapathy, "RNA splice junctions of different classes of eukaryotes: sequence statistics and functional implications in gene expression." Nucleic Acids Research, 1987, vol. 15. No. 17, pp. 7155-7174.
Sherratt, et al., Exon Skipping and Translation in Patients with Frameshift Deletions in the Dystrophin Gene, Am. J. Hum. Genet, 1993, pp. 1007-1015, vol. 53.
Shiga, et al., Disruption of the Splicing Enhancer Sequence within Exon 27 of the Dystrophin Gene by a Nonsense Mutation Induces Partial Skipping of the Exon and is Responsible for Becker Muscular Dystrophy, J. Clin. Invest., Nov. 1997, pp. 2204-2210, vol. 100, No. 9.
Simoes-Wust, et al., bcl-xL Antisense Treatment Induces Apoptosis in Breast Carcinoma Cells, Int. J. Cancer, 2000, pp. 582-590, vol. 87.
Sterrenburg, et al., "Gene expression of profiling highlights defective myogenesis in DMD patients and a possible role for bone morphogenetic protein 4," Neurobiology of Disease 23(1):228-236 (2006).
Surono et al. Chimeric RNA/ethylene-Bridged Nucleic Acids Promote Dystrophin Expression in Myocytes of Duchenne Muscular Dystrophy by Inducing Skipping of the Nonsense Mutation-Encoding Exon Hum Gene Ther. vol. 15(8) pp. 749-757 (2004).
Surono et al. "Six Novel Transcripts that Remove a Huge Intron Ranging from 250 to 800 kb Are Produced by Alternative Splicing of the 5' Region of the Dystrophin Gene in Human Skeletal Muscle." BBRC 239 895-899 (1997).
Suter, et al., Double-target antisense U7 snRNAs promote efficient skipping of an aberrant exon in three human B-thalassemic mutations, Human Molecular Genetics, 1999, pp. 2415-2423, vol. 8, No. 13.
Suwanmanee et al. (2002) "Restoration of Human b-globin Gene Expression in Murine and Human IVS2-654 Thalassemic Erythroid Cells by Free Uptake of Antisense Oligonucleotides" Mol. Pharmacology 62(3):545-553.
Takashima et al. Oligonucleotides Against a Splicing Enhancer Sequence Led to Dystrophin Production in Muscle Cells From a Duchenne Muscular Dystrophy Patient Brain Dev 2001 (December); 23:788-90.
Takeshima, et al., Modulation of In Vitro Splicing of the Upstream Intron by Modifying an Intra-Exon Sequence Which is Deleted from the Dystrophin Gene in Dystrophin Kobe, J. Clin. Invest., Feb. 1995, pp. 515-520, vol. 95.
Tanaka, et al., Polypurine Sequences within a Downstream Exon Function as a Splicing Enhanced, Molecular and Cellular Biology, Feb. 1994, pp. 1347-1354, vol. 14, No. 2.
Thanh, et al., "Characterization of revertant muscle fibers in Duchenne muscular dystrophy, using exon-specific monoclonal antibodies against dystrophin." Am. J. Hum. Genet. 1995, vol. 56, pp. 725-731.
Third Party's Statement for Japan Appl. No. 2002-529499, dated Oct 29, 2010.
Tian H, Kole R, "Selection of novel exon recognition elements from a pool of random sequences." Mol Cell Biot 15(11):6291-8. (1995).
TREAT-NMD Neuromuscular Network, Jan. 11, 2008.

Tsuchida "Peptides, Proteins & Antisense: the role of myostatin and bone morphogenetic proteins in muscular disorders," Expert Opinion of Biologica Therapy 6(2):147-153 (2006).
Van Deutekom et al. Advances in Duchenne Muscular Dystrophy Gene Therapy 2003 Nat Rev Genet 4(10): 774-83.
Van Deutekom, et al., Antisense-induced exon skipping restores dystrophin expression in DMD patient derived muscle cells. Hum Mol Genet. Jul. 15, 2001:10(15:1547-54).
Van Deutekom, et al., Local Dystrophin Restoration with Antisense Oligonucleotide PRO051, N. England J. Med., Dec. 27, 2007, pp. 2677-2686.
Verreault, et al. "GENE silencing in the development of personalized cancer treatment: the targets, the agents and the delivery systems." Curr. Gene Therapy, 2006, vol. 6, pp. 505-553.
Watakabe, et al., The role of exon sequences in splice site selection, Genes & Development, 1993, pp. 407-418, vol. 7.
Wells et al. Enhanced in Vivo Delivery of Antisense Oligonucleotide to Restore Dystrophin Expression in Adult MDX Mouse Muscle FEBS Letters 2003 552: 145-149.
Wheway and Roberts. "The Dystrophin Lymphocyte promoter revisited: 4.5-megabase intron, or artefact?" Neuromuscular Disorders 13(2003) 17-20.
Wilton, et al., "Specific removal of the nonsense mutation from the mdx dystrophin protein mRNA using antisense oligonucleotides." Neuromuscular Disorders, 1999, vol. 9, pp. 330-338.
Wilton, et al., "Antisense oligonucleotides, exon skipping and the dystrophin gene transcript," Acta Myologica XXIV:222-229 (2005).
Arechavala-Gomeza, et al., "Comparative Analysis of Antisense Oligonucleotide Sequences for Targeted Skipping of Exon 51 During Dystrophin pre-mRNA Splicing in Human Muscle" Hum Gene Ther 2007 pp. 798-810 vol. 18 No. 9.
Austin, et al., "Expression and synthesis of alternatively spliced variants of Dp71 in adult human brain." Neuromuscular Disorders. 10(2000) 187-193.
Burnett, et al., "DNA sequence-specific polyamides alleviate transcription inhibition associated with long GAA-TTC repeats in Friedreich's ataxia," PNAS, 2006, pp. 11497-11502, vol. 103, No. 31.
Caplen, et al., "Rescue of polyglutamine-mediated cytotoxicity by double-stranded RNA-mediated RNA interference," Human molecular genetics, 2002, pp. 175-184, vol. 11, No. 2.
Fu, et al., "An Unstable Triplet Repeat in a Gene Related to Myotonic Muscular Dystrophy", Science, vol. 255, 1256-1258. 1992.
Furling, et al., "Viral vector producing antisense RNA restores myotonic dystrophy myoblast functions", Gene Therapy (2003) 10, 795-802.
Galderisi, et al., "Myotonic dystrophy: antisense oligonucleotide inhibition of DMPK gene expression in vitro." Biochem Biophys Res Commun 221:750-754 (1996).
Handa, et al., "The AUUCU repeats responsible for spinocerebellar ataxia type 10 form unusual RNA hairpins." Journal of Biological Chemistry 280(32):29340-29345 (2005).
Hasholt, et al., "Antisense downregulation of mutant huntingtin in a cell model," Journal of Gene Medicine, 2003, pp. 528-538, vol. 5, No. 6.
Hoffman, et al., "Somatic reversion/suppression of the mouse mdx phenotype in vivo." J. of the Neurological Sciences, 1990, 99: 9-25.
Langlois, et al., "Hammerhead ribozyme-mediated destruction of nuclear foci in myotonic dystrophy myoblasts," Molecular therapy, 2003, pp. 670-680, vol. 7, No. 5.
Liu, et al., "Specific inhibition of Huntington's disease gene expression by siRNAs in cultured cells", Proc. Japan Acad. 79, Ser. B (2003), 293-298.
Matsuo, et al., Exon Skipping during Splicing of Dystrophin mRNA Precursor due to an Intraexon Deletion in the Dystrophin Gene of Duchenne Muscular Dystrophe Kobe. J. Clin. Invest. 87, 2127-2131.
Vickers, et al., "Efficient reduction of target RNAs by small interfering RNA and RNase H-dependent antisense agents. A comparative analysis." J. Biol. Chem. 278(9):7108-7118.
Wilton, et al., "Antisense oligonucleotide-induced exon skipping across the human dystrophin gene transcript." Mol Ther. Jul. 2007:15(7)1288-96.

(56) References Cited

OTHER PUBLICATIONS

Yen, et al., "Sequence-specific cleavage of Huntingtin MRNA by catalytic DNA," *Annals of Neurology,* 1999, pp. 366-373, vol. 46, No. 3.
Chaubourt et al: "Muscular nitric oxide synthase (muNOS) and utrophin", Journal of Physiology, vol. 96(1-2), 2002, pp. 43-52, XP002469418.
Radley et al, "Duchenne muscular dystrophy: Focus on pharmaceutical and nutritional interventions", International. Jour. of Biochem. and Cell Biol., vol. 39(3), Oct. 2006, pp. 469-477, XP005831292.
Segalat et al., "Capon expression in skeletal muscle is regulated by position, repair, NOS activity, and dystrophy" Experimental Cell Research, vol. 302(2); Jan. 2005, pp. 170-179, XP004649912.
Anderson et al., "Correlated NOS-I and myf5 expression by satelite cells in mdx mouse muscle regeneration during NOS manipulation and deflazacort treatment", Neuromuscular Disorders, vol. 13(5); 2003, pp. 388-396, XP002469419.
Arruda V R: "The role of immunosuppression in gene and cell based treatments for Duchenne Muscular Dystrophy", Molecular Therapy, vol. 15(6), Jun. 2007, pp. 1040-1041 XP009096112.
Granchelli et al., "Pre-clinical screening of drugs using the mdx mouse" Neuromuscular Disorders, Pergamon Pres, vol. 10(4-5), Jun. 2000, pp. 235-239, XP002305261.
Rolland et al., "Overactivity of exercise-sensitive cation channels and their impaired modulation by IGF-1 in mdx native muscle fibers: beneficial effect of pentoxifylline", Neurobiology of Disease, vol. 24(3), Dec. 2006, pp. 466-474, XP024901469.
Zhou Guang-Qian et al., "Current understanding of dystrophin-related muscular dystrophy and therapeutic challenges ahead", Chinese Medical Journal, vol. 119(16), Aug. 2006, pp. 1381-1391, XP002542429.
International Search Report dated Feb. 9, 2009, corresponding to PCT/NL2008/050673.
Aartsma-Rus et al., "Comparative analysis of antisense oligonucleotide analogs for targeted DMD exon 46 skipping in muscle cells," Gene Therapy (2004), 11:1391-1398.
European Search Report Annex for EP 03077205 dated Nov. 19, 2003.
European Search Report for EP 03077205 dated Oct. 12, 2003.
Reuser et al. "Uptake and Stability of Human and Bovine Acid A-glucosidase in Cultured Fibroblasts and Skeletal Muscle Cells From Plycogenesis Type II Patients", *Exp. Cell Res.* (1984) 155, pp. 178-189.
Samoylova et al. "Elucidation of Muscle-Binding Peptides by Phase Display Screening" *Muscle Nerve* (1999), 22, pp. 460-466.
Rosen et al., "Combination Chemotherapy and Radiation Therapy in the Treatment of Metastatic Osteogenic Sarcoma," Cancer, vol. 35(3), pp. 622-630, Mar. 1975.
Wenk J. et al., "Quantitation of Mr 46000 and Mr 300000 mannose 6-phospate receptors in human cells and tissues.," Biochen Int., vol. 23(4), pp. 723-731, Mar. 1991 (Abstract).
Reitter, "Deflazacort vs. prednisone in Duchenne muscular dystrophy: trends of an ongoing study," Brain & Development, vol. 17 (suppl), pp. 39-43 (1995).
Bijvoet et al., "Recombinant human acid α-glucosidase: high level production in mouse milk, biochemical characteristics, correction of enzyme deficiency in GSDII KO mice," Human Molecular Genetics, vol. 7(11), pp. 1815-1824 (1998).
Martiniuk et al., "CorrBMection of glycogen storage disease type II by enzyme replacement with a recombinant Bhuman acid maltase produced by over-expression in a CHO-DHFR(neg) cell line.," Biochem Biophys Res Commun., vol. 276(3), pp. 917-923, Oct. 5, 2000 (Abstract).
Zhang et al., "Efficient expression of naked dna delivered intraarterially to limb muscles of nonhuman primates.," Hum Gene Ther., vol. 12(4), pp. 427-438, Mar. 1, 2001 (Abstract).
Brown MD et al., "Gene delivery with synthetic (non viral) carriers.," Int J Pharm., 229(1-2), pp. 1-21, Oct. 23, 2001 (Abstract).

Arap et al., "Steps toward mapping the human vasculature by phage display," Nature Publishing Group, Nature Medicine, vol. 8(2), pp. 121-127, Feb. 2002.
O'Shaughnessy et al., "Superior Survival With Capecitabine Plus Docetaxel Combination Therapy in Anthracycline-Pretreated Patients With Advanced Breast Cancer: Phase III Trial Results," Journal of Clinical Oncology, vol. 20, No. 12, pp. 2812-2823, Jun. 15, 2002.
Hassan AB, "Keys to the Hidden Treasures of the Mannose 6-Phosphate/Insulin-Like Growth Factor 2 Receptor," American Journal of Pathology, vol. 162(1), pp. 3-6, Jan. 2003.
Lu et al., "Non-viral gene delivery in skeletal muscle: a protein factory," Gene Therapy, vol. 10, pp. 131-142 (2003).
Ghosh et al., "Mannose 6-Phosphate Receptors: New Twists in the Tale," Nature Reviews Molecular Cell Biology, vol. 4, pp. 202-212, Mar. 2003.
Gollins et al., "High-efficiency plasmid gene transfer into dystrophic Muscle," Gene Therapy, vol. 10, pp. 504-512 (2003).
Weisbart RH et al., "Cell type specific targeted intracellular delivery into muscle of a monoclonal antibody that binds myosin IIb.," Mol Immunol., vol. 39(13), pp. 783-789, Mar. 2003 (Abstract).
Politano et al., "Gentamicin administration in Duchenne patients with premature stop codon. Preliminary results," Acta Myologica, vol. 22, pp. 15-21 (2003).
Garcia-Blanco et al., "Alternative splicing in disease and therapy," Nature Biotechnology, vol. 22(5), pp. 535-546, May 2004.
Lu et al., "Systemic delivery of antisense oligoribonucleotide restores dystrophin expression in body-wide skeletal muscles," PNAS, vol. 102(1), pp. 198-203, Jan. 4, 2005.
Duboc et al., "Effect of Perindopril on the Onset and Progression of Left Ventricular Dysfunction in Duchenne Muscular Dystrophy," Journal of the American College of Cardiology, vol. 45(6), pp. 855-857, Mar. 15, 2005.
Alter et al., "Systemic delivery of morpholino oligonucleotide restores dsytrophin expression bodywide and improves dystrophic pathology," Nature Medicine, vol. 12(2), pp. 175-177, Feb. 2006, Published Online on Jan. 29, 2006.
Takeshima et al., "Intravenous Infusion of an Antisense Oligonucleotide Results in Exon Skipping in Muscle Dystrophin mRNA of Duchenne Muscular Dystrophy," Pediatric Research, vol. 59(5), pp. 690-694 (2006).
El-Andaloussi et al., "Induction of splice correction by cell-penetrating peptide nucleic acids.," J Gene Med, vol. 8(10), pp. 1262-1273, Oct. 2006 (Abstract).
European Patent Office, European Patent Office Action regarding European Patent Application No. EP 05 076 770.6 dated Jan. 29, 2007, 5 pages.
Yin et al., "Effective Exon Skipping and Restoration of Dystrophin Expression by Peptide Nucleic Acid Antisense Oligonucleotides in mdx Mice," The Amerian Society of Gene Therapy, vol. 16, No. 1, pp. 38-45, Jan. 2008.
Aartsma-Rus et al. "Guidelines for Antisense Oligonucleotide Design and Insight into Splice-modulation Mechanisms." *Molecular Therapy 2009* pp. 548-553 (Published Online Sep. 23, 2008).
Buck et al., "Design Strategies and Performance of Custom DNA Sequencing Primers" *Biotechniques.* 27:528-536, 1999.
GenBank accession No. AZ993191.1, 2MO278E12F mouse 10kb plasmid UUGC2M library Mus muscu genomic clone UUGC2MO278E12F, genomic survey sequence, entry created and last updated on Apr. 27, 2001.
GenBank accession No. EW162121.1, rfat0126_k17.y1 fat Sus scrofa cDNA5-, mRNA sequence, entry created on Aug. 13, 2007, last updated on Mar. 3, 2011.
Ikezawa et al. "Dystrophin gene analysis on 130 patients with Duchenne Muscular dystrophy with a special reference to muscle mRNA analysis." *Brain & Develop.* 20:165-168, 1998.
International Preliminary Report on Patentability and Written Opinion for PCT/EP2007/054842, mailed on Nov. 21, 2008, 8 pages.
International Search Report for PCT/EP2007/054842, mailed on Aug. 21, 2007, 3 pages.
Kinali et al. 2009 Local Restoration of Dystrophin Expression With the Morpholino Oligomer AVI-4658 in Duchenne Muscular Dystro-

(56) References Cited

OTHER PUBLICATIONS phy: A Single-blind, Placebo-Controlled Dose-Escalation, Proof-of Concept Study. *Lancet Neurol.* vol. 8(10) pp. 918-928.
Van Vliet, et al., "Assessment of the feasibility of exon 45-55 multiexon skipping for duchenne muscular dystrophy." *BMC Medical Genetics,* Dec. 2008, vol. 9:105 (7 pages).
Varani et al. "The G.U. wobble base pair: A fundamental building block of RNA structure crucial to RNA function in diverse biological systems." *EMBO Reports* (2000), vol. 1:18-23.
Verhaart et al., "Prednisolone treatment does not interfere with 2'-O-methyl phosphorothioate antisense-mediated exon skipping in Duchenne muscular dystrophy." *Hum Gene Ther.* Mar. 2012;23(3):262-73. Epub Jan. 26, 2012.
EPO—Munich, Translation of Japanese Patent Application No. 2000-125448 (D64).
EPO—Munich, Translation of Japanese Patent Application No. 2000-256547(D66).
Beggs et al., "Detection of 98% of DMD/BMD gene deletions by polymerase chain reaction," Human Genetics, vol. 86, pp. 45-48 (1990).
Summerton et al., "Morpholino Antisense Oligomers: Design, Preparation, and Properties," Antisense & Nucleic Acid Drug Development, vol. 7, pp. 187-195 (1997).
Takeshima et al., "Basic research for treatment of Duchene muscular dystrophy using induction of exon skipping by means of antisense oligo DNA: effect of in vivo administration in mice," Park IP Translations, vol. 15, No. 2, 6 pages.
Takeshima et al., "Expression of Dystrophin Protein in Cultured Duchenne Muscular Dystrophy Cells by Exon Skipping Induced by Antisense Oligonucleotide" (Abstract); Abstract of the Japan Society of Human Genetics General Meeting Program, Nov. 17-19, 1999.
Kuhihara, T., et al., "Muscular Disorders," *Review/Advances in Neurological Therapeutics,* 5 pages, 2000.
Kuhihara, T., et al., "Muscular Disorders," *Review/Advances in Neurological Therapeutics,* 4 pages, 2000 (English Translation).
Onlo Nederlandsch Octrooibureau, Grounds of Appeal,—EP1619249, 16 pages, Aug. 23, 2013.
Onlo Nederlandsch Octrooibureau, List of all submitted documents—EP1619249, 4 pages, Aug. 23, 2013.
Onlo Nederlandsch Octrooibureau, Alignments of AON exon 53, EP1619249, 1 page, Jan. 8, 2013.
Onlo, "Comparative analysis of AONs for inducing the skipping of exon 45 and 53 from the dystrophin gene in human control muscle cells," EP1619249, 3 pages, Aug. 23, 2013.
Onlo, "Comparative Analysis of AONs for inducing the skipping of exon 53 from the dystrophin gene in human control muscle cells," EP1619249, 3 pages, Jan. 8, 2014.
Sarepta Therapeutics, Inc., "Sarepta Therapeutics and University of Western Australia Announce Exclusive Worldwide Licensing Agreement for Exon-Skipping Program in Duchenne Muscular Dystrophy," *News Release,* EP1619249, 3 pages, Apr. 11, 2013.
Squires, Kathleen E., "An Introduction to Nucleoside and Nucleotide Analogues," *Antiviral Therapy* 6 (Suppl. 3) pp. 1-14 (2001).
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Motion 3 (for judgment that Claims 11-12, 14-15, and 17-29 of U.S. Appl. No. 13/550,210 are barred under 35 U.S.C. §135(b)); 25 pages, filed Nov. 18, 2014 [Patent Interference No. 106,008].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Motion 2 (for Judgment Under 35 U.S.C. §112(b)), 32 pages, filed Nov. 18, 2014 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Motion 1 (for Judgment Under 35 U.S.C. §112(a)), 38 pages, filed Nov. 18, 2014 [Patent Interference No. 106,008 (RES)].
University of Western Australia, *University of Western Australia* (U.S. Pat. Nos. 8,455,636, 7,960,541, 7,807,816, 8,486,907) v. *Academisch Ziekenhuis Leiden* (U.S. Appl. Nos. 11/233,495, 13/550,210, 14/198,992), Declaration of Matthew J.A. Wood, M.D. ,D. Phil.—UVA Exhibit 2081, 184 pages, filed Sep. 19, 2014 [Patent Interference Nos. 106,007, 106,008, 106,113 (RES)].
University of Western Australia, *University of Western Australia* (U.S. Pat. Nos. 7,960,541, 7,807,816) v. *Academisch Ziekenhuis Leiden* (U.S. Appl. No. 13/550,210), University of Western Australia List of Proposed Motions, 6 pages, filed Sep. 10, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's List of Proposed Motions, 8 pages, filed Sep. 10, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 1 (for Judgment that UWA's Claims are Unpatentable Under 35 U.S.C. §§ 102 and 103) 69 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 2 (to Deny UWA the Benefit of AU2004903474, 24 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's Substantive Motion 3 (for Judgment of Unpatentability Based on Myriad), 20 pages, filed Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Declaration of Erik Sontheimer, Ph.D., 112 pages, filed Nov. 17, 2014 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia List of Proposed Motions, 7 pages, filed Sep. 10, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 1 (for Judgment Under 35 U.S.C. §112(a)), 40 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 2 (for Judgment Under 35 U.S.C. §112(b)), 34 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 3 (Requesting an Additional Interference Between UWA U.S. Pat. No. 8,455,636 and Academisch Ziekenhuis Leiden's U.S. Appl. No. 14/248,279), 36 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 1 (for Judgment that UWA Claims are Unpatentable Under 35 U.S.C. §§ 102 and 103) 69 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 3 (for Judgment of Unpatentability based on Myriad), 19 pages, filed Nov. 18, 2014 [Patent Interference No. 106,007 (RES)].

(56) References Cited

OTHER PUBLICATIONS

Academisch Ziekenhuis Leiden, *University of Western Australia* (U.S. Pat. No. 8,455,636) v. *Academisch Ziekenhuis Leiden* (U.S. Appl. No. 11/233,495), AZL Substantive Motion 2 (To Deny UWA the Benefit of AU 2004903474), 23 pages, filed Nov. 18, 2014 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's List of Proposed Motions, 6 pages, filed Sep. 10, 2014 [Patent Interference No. 106,007 (RES)].
University of Western Australia, *University of Western Australia* (Patent 8,486,907) v. *Academisch Ziekenhuis Leiden* (Application No. 14/198,992),University of Western Australia Motion 1 (to Maintain Interference Between UWA U.S. Pat. No. 8,486,907 and Academisch Ziekenhuis Leiden's U.S. Appl. No. 14/198,992), 45 pages, filed Nov. 18, 2014 [Patent Interference No. 106,013 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Responsive Motion 4 (to Add Two New Claims), 65 pages, filed Dec. 23, 2014 [Patent Interference No. 106,007 (RES)].
Academisch Ziekenhuis Leiden *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden Responsive Motion 4 (to Add Two New Claims), 57 pages, filed Dec. 23, 2014 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Second Declaration of Erik Sontheimer, Ph.D., 44 pages, filed Dec. 23, 2014 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List as of Feb. 17, 2015, 8 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), University of Western Australia Opposition 1 (Regarding Patentability Under 35 U.S. C. § 102/103), 38 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 2 (to Retain UWA's Benefit of AU 2004903474), 37 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 3 (Regarding Patentability Under 35 U.S. C. § 101), 22 pages, filed Feb. 17, 2015 [Patent Interference No. 106,007 (Res)].
University of Western Australia, *University of Western Australia* (U.S. Pat. No. 8,455,636) v. *Academisch Ziekenhuis Leiden* (U.S. Appl. No. 11/233,495), University of Western Australia Opposition 4 (to deny entry of AZL's Proposed New Claims 104 and 105), 36 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Feb. 17, 2015), 18 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 1 (35 U.S. C. § 112(a)), 93 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 2 (Indefiniteness), 31 pages, filed Feb. 17, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 3 (Standing Order 11203.1 and 37 C.F.R. § 41.202(a) and (e)), 20 pages, filed Feb. 17, 2015 [Patent Interference No. 106,007 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210) University of Western Australia Exhibit List as of Feb. 17, 2015, 8 pages, filed Feb. 17, 2015 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210) University of Western Australia Opposition 1 (Regarding Patentability Under 35 U.S.C. § 102/103), 39 pages, filed Feb. 17, 2015 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210) University of Western Australia Opposition 2 (to Retain UWA's Benefit of AU 2004903474), 31 pages, filed Feb. 17, 2015 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210) University of Western Australia Opposition 3 (Regarding Patentability Under 35 U.S.C. § 101), 22 pages, filed Feb. 17, 2015 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210) University of Western Australia Opposition 4 (to deny entry of AZL's Proposed New Claims 30 and 31), 36 pages, filed Feb. 17, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210) Academisch Ziekenhuis Leiden List of Exhibits (as of Feb. 17, 2015) 18 pages, filed Feb. 17, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210) Academisch Ziekenhuis Leiden Opposition 1 (35 U.S.C. § 112(a)), 83 pages, filed Feb. 17, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210) Academisch Ziekenhuis Leiden Opposition 2 (Indefiniteness), 32 pages, filed Feb. 17, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210) Academisch Ziekenhuis Leiden Opposition 3 (U.S.C. § 135(b)), 44 pages, filed Feb. 17, 2015 [Patent Interference No. 106,008 (RES)].
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden List of Exhibits (as of Feb. 17, 2015) 3 pages, filed Feb. 17, 2015 [Patent Interference No. 106,013 (RES)].
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden Opposition 1 (Standing Order 11203.1 and 37 C.F.R. § 41.202 (a) and (e)) 20 pages, filed Feb. 17, 2015 [Patent Interference No. 106,013 (RES)].
University of Western Australia, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. No. 7,960,541 and U.S. Pat. No. 7,807,816) v. *Academisch Ziekenhuis Leiden* (U.S. Appl. No.

(56) References Cited

OTHER PUBLICATIONS

13/550,210) [Patent Interference No. 106,008 (RES)], Second Declaration of Matthew J.A. Wood, M.D., D. Phil., 78 pages, filed Feb. 17, 2015.
Academisch Ziekenhuis Leiden, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. No. 7,960,541 and U.S. Pat. No. 7,807,816) v. *Academisch Ziekenhuis Leiden* (U.S. Appl. No. 13/550,210) [Patent Interference No. 106,008 (RES)], 3$^{rd}$ Declaration of Erik J. Sontheimer, Ph.D. 123 pages, filed Feb. 17, 2015 [Patent Interference Nos. 106,007 and 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495)[Patent Interference No. 106,007 (RES)] and *University of Western Australia* (U.S. Pat. No. 7,960,541 and U.S. Pat. No. 7,807,816) v. *Academisch Ziekenhuis Leiden* (U.S. Appl. No. 13/550,210) [Patent Interference No. 106,008 (RES)], Declaration of Judith Van Deutekom, 45 pages, filed Feb. 17, 2015 [Patent Interference Nos. 106,007 and 106,008 (RES)].
University of Western Australia, *University of Western Australia* (U.S. Pat. No. 8,455,636) v. *Academisch Ziekenhuis Leiden* (U.S. Appl. No. 11/233,495) University of Western Australia Objections (to Opposition Evidence) 15 pages, filed Feb. 24, 2015 [Patent Interference No. 106,007 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210) University of Western Australia Objections (to Opposition Evidence) 15 pages, filed Feb. 24, 2015 [Patent Interference No. 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 1 (for Judgment that UWA's Claims are Unpatentable Under 35 U.S.C. §§ 102 and 103) 17 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 2 (to Deny the Benefit of AU 2004903474) 11 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 3 (for Judgment of Unpatentability based on Myriad) 12 pages, filed Apr. 3, 2015 Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 4 (in Support of Responsive Motion 4 to Add Two New Claims) 17 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Apr. 3, 2015) 18 pages, filed Apr. 3, 2015 [Patent Interference No. 106,007 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden Reply 1 (for Judgment that UWA's Claims are Unpatentable Under 35 U.S.C. §§ 102 and 103) 17 pages, filed Apr. 3, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden Reply 2 (to Deny the Benefit of AU 2004903474) 12 pages, filed Apr. 3, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden Reply 3 (for Judgment of Unpatentability based on Myriad) 13 pages, filed Apr. 3, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden Reply 4 (in Support of Responsive Motion 4 to Add Two New Claims) 17 pages, filed Apr. 3, 2015 [Patent Interference No. 106,008 (RES)].
Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden List of Exhibits (as of Apr. 3, 2015) 18 pages, filed Apr. 3, 2015 [Patent Interference No. 106,008 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 1 (to AZL Opposition 28 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 2 (to AZL Opposition 22 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 3 (to Institute an Interference) 17 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 3, 2015 [Patent Interference No. 106,007 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Request for Oral Argument, 3 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495 University of Western Australia Request for Oral Argument, 4 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495 University of Western Australia Miscellaneous Motion 4 (to exclude evidence), 21 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495 University of Western Australia Exhibit List, 10 pages, filed Apr. 10, 2015 [Patent Interference No. 106,007 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Reply 1 (to AZL Opposition 1) 28 pages, filed Apr. 3, 2015 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Reply 2 (to AZL Opposition 2) 22 pages, filed Apr. 3, 2015 [Patent Interference No. 106,008 (RES)].
University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Reply 3 (for judgment under 35 U.S.C. §135(b)) 19 pages, filed Apr. 3, 2015 [Patent Interference No. 106,008 (RES)].
University of Western Australia, *University of Western Australia* (U.S. Pat. No. 7,960,541 and U.S. Pat. No. 7,807,816) v. *Academisch*

(56) References Cited

OTHER PUBLICATIONS

*Ziekenhuis Leiden* (U.S. Appl. No. 13/550,210), University of Western Australia Exhibit List, 10 pages, filed Apr. 3, 2015 [Patent Interference No. 106,008 (RES)].

Academisch Ziekenhuis Leiden, *University of Western Australia* (U.S. Pat. No. 7,960,541 and U.S. Pat. No. 7,807,816) v. *Academisch Ziekenhuis Leiden* (U.S. Appl. No. 13/550,210), Academisch Ziekenhuis Leiden Request for Oral Argument, 3 pages, filed Apr. 10, 2015 [Patent Interference No. 106,008 (RES)].

University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Request for Oral Argument, 4 pages, filed Apr. 10, 2015 [Patent Interference No. 106,008 (RES)].

University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Miscellaneous Motion 4 (to exclude evidence), 21 pages, filed Apr. 10, 2015 [Patent Interference No. 106,008 (RES)].

University of Western Australia, *University of Western Australia* (U.S. Pat. No. 7,960,541 and U.S. Pat. No. 7,807,816) v. *Academisch Ziekenhuis Leiden* (U.S. Appl. No. 13/550,210), University of Western Australia Exhibit List, 10 pages, filed Apr. 10, 2015 [Patent Interference No. 106,008 (RES)].

Aarstsma-Rus et al. "Theoretic Applicability of Antisense-Mediated Exon Skipping for Duchenne Muscular Dystrophy" Human Mutation 2009 pp. 293-299 vol. 30 No. 3.

Barany "The ligase chain reaction in a PCR world." PCR Methods Appl. Aug. 1991;1(1):5-16.

Denny et al., "Oligo-riboprobes. Tools for in situ hybridisation". Histochemistry (1988) 89:481-493.

Highfield "Science: Boffin log", The Daily Telegraph, http://www.telegraph.co.uk/science/science-news/3320286/Science-Boffin-log.html, (Hope for Muscular Dystrophy Drug) Jan. 1, 2008.

International Search Report for PCT/NL2009/050006 dated Jul. 31, 2009.

International Search Report for PCT/NL2009/050113 dated Jun. 30, 2010.

Ito, et al., "Purine-Rich Exon Sequences Are Not Necessarily Splicing Enhancer Sequence in the Dystrophin Gene." *Kobe J. Med. Sci.* 47, 193/202, Oct. 2001.

Smith et al., "Muscle-specific peptide #5", Mar. 23, 1999. From http://www.ebi.ac.uk/cgi-bin/epo/epofetch?AAW89659, downloaded Jul. 16, 2007. XP 002442550.

Van Ommen (2008) "The Therapeutic Potential of Antisense-Mediated Exon-Skipping" Curr Opin Mol. Ther vol. 10(2) pp. 140-149.

Wang et al. "Adeno-associated virus vector carrying human minidystrophin genes effectively ameliorates muscular dystrophy in mdx mouse model", 05 Dec. 2000, P.N.A.S. 97(25):13714-13719.

* cited by examiner

Fig. 2B
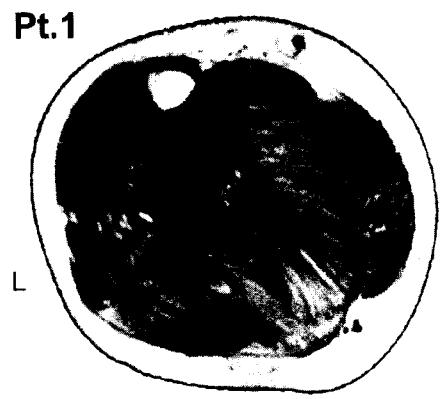
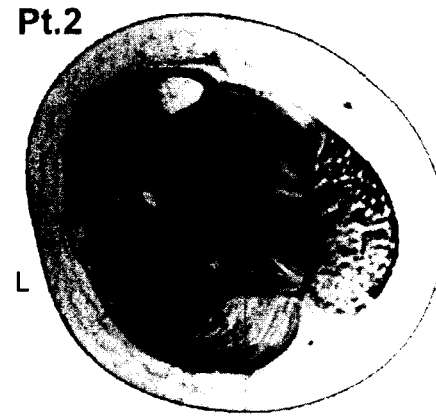
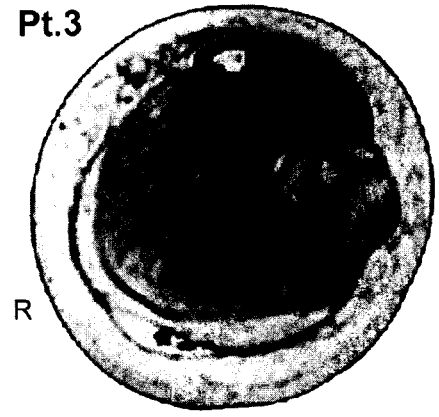
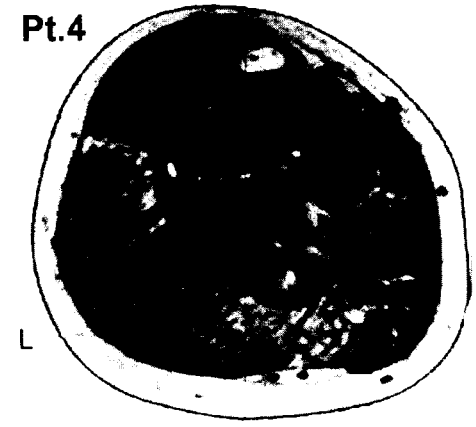

Fig. 2E
Pt.1
Δ50
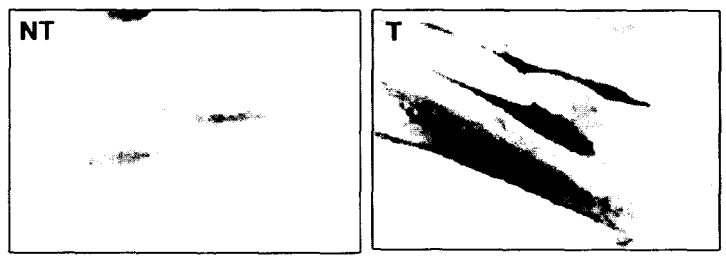
Pt.2
Δ48-50
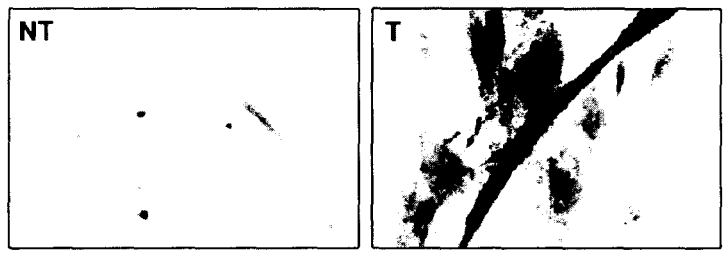
Pt.3
Δ49-50
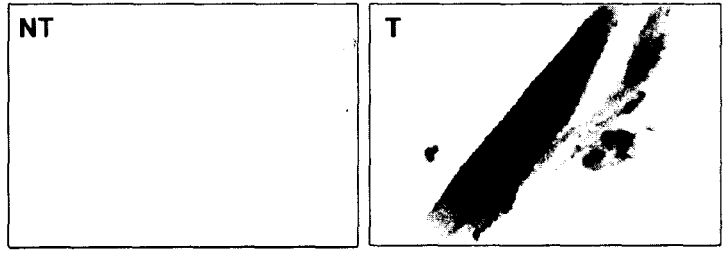
Pt.4
Δ52
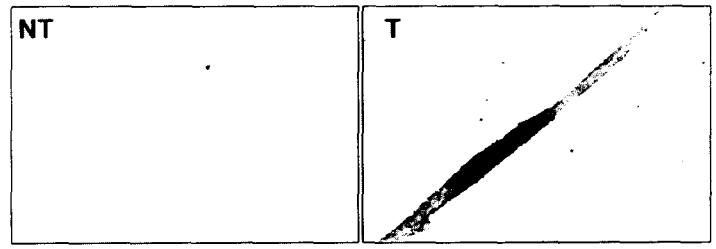

Figure 7A

SEQ ID NO 1:
MLWWEEVEDCYEREDVQKKTFTKWVNAQFSKFGKQHIENLFSDLQDGRRLLDLLEGLTG
QKLPKEKGSTRVHALNNVNKALRVLQNNNVDLVNIGSTDIVDGNHKLTLGLIWNIILHWQ
VKNVMKNIMAGLQQTNSEKILLSWVRQSTRNYPQVNVINFTTSWSDGLALNALIHSHRPDL
FDWNSVVCQQSATQRLEHAFNIARYQLGIEKLLDPEDVDTTYPDKKSILMYITSLFQVLPQQ
VSIEAIQEVEMLPRPPKVTKEEHFQLHHQMHYSQQITVSLAQGYERTSSPKPRFKSYAYTQ
AAYVTTSDPTRSPFPSQHLEAPEDKSFGSSLMESEVNLDRYQTALEEVLSWLLSAEDTLQA
QGEISNDVEVVKDQFHTHEGYMMDLTAHQGRVGNILQLGSKLIGTGKLSEDEETEVQEQM
NLLNSRWECLRVASMEKQSNLHRVLMDLQNQKLKELNDWLTKTEERTRKMEEEPLGPDL
EDLKRQVQQHKVLQEDLEQEQVRVNSLTHMVVVVDESSGDHATAALEEQLKVLGDRWAN
ICRWTEDRWVLLQDILLKWQRLTEEQCLFSAWLSEKEDAVNKIHTTGFKDQNEMLSSLQK
LAVLKADLEKKKQSMGKLYSLKQDLLSTLKNKSVTQKTEAWLDNFARCWDNLVQKLEKS
TAQISQAVTTTQPSLTQTTVMETVTTVTTREQILVKHAQEELPPPPPQKKRQITVDSEIRKRL
DVDITELHSWITRSEAVLQSPEFAIFRKEGNFSDLKEKVNAIEREKAEKFRKLQDASRSAQA
LVEQMVNEGVNADSIKQASEQLNSRWIEFCQLLSERLNWLEYQNNIIAFYNQLQQLEQMT
TTAENWLKIQPTTPSEPTAIKSQLKICKDEVNRLSGLQPQIERLKIQSIALKEKGQGPMFLDA
DFVAFTNHFKQVFSDVQAREKELQTIFDTLPPMRYQETMSAIRTWVQQSETKLSIPQLSVT
DYEIMEQRLGELQALQSSLQEQQSGLYYLSTTVKEMSKKAPSEISRKYQSEFEEIEGRWKK
LSSQLVEHCQKLEEQMNKLRKIQNHIQTLKKWMAEVDVFLKEEWPALGDSEILKKQLKQC
RLLVSDIQTIQPSLNSVNEGGQKIKNEAEPEFASRLETELKELNTQWDHMCQQVYARKEAL
KGGLEKTVSLQKDLSEMHEWMTQAEEEYLERDFEYKTPDELQKAVEEMKRAKEEAQQKE
AKVKLLTESVNSVIAQAPPVAQEALKKELETTTNYQWLCTRLNGKCKTLEEVWACWHEL
LSYLEKANKWLNEVEFKLKTTENIPGGAEEISEVLDSLENLMRHSEDNPNQIRILAQTLTD
GGVMDELINEELETFNSRWRELHEEAVRRQKLLEQSIQSAQETEKSLHLIQESLTFIDKQLA
AYIADKVDAAQMPQEAQKIQSDLTSHEISLEEMKKHNQGKEAAQRVLSQIDVAQKKLQDV
SMKFRLFQKPANFEQRLQESKMILDEVKMHLPALETKSVEQEVVQSQLNHCVNLYKSLSE
VKSEVEMVIKTGRQIVQKKQTENPKELDERVTALKLHYNELGAKVTERKQQLEKCLKLSR
KMRKEMNVLTEWLAATDMELTKRSAVEGMPSNLDSEVAWGKATQKEIEKQKVHLKSITE
VGEALKTVLGKKETLVEDKLSLLNSNWIAVTSRAEEWLNLLLEYQKHMETFDQNVDHITK
WIIQADTLLDESEKKKPQQKEDVLKRLKAELNDIRPKVDSTRDQAANLMANRGDHCRKLV
EPQISELNHRFAAISHRIKTGKASIPLKELEQFNSDIQKLLEPLEAEIQQGVNLKEEDFNKD
MNEDNEGTVKELLQRGDNLQQRITDERKREEIKIKQQLLQTKHNALKDLRSQRRKKALEIS
HQWYQYKRQADDLLKCLDDIEKKLASLPEPRDERKIKEIDRELQKKKEELNAVRRQAEGL
SEDGAAMAVEPTQIQLSKRWREIESKFAQFRRLNFAQIHTVREETMMVMTEDMPLEISYVP
STYLTEITHVSQALLEVEQLLNAPDLCAKDFEDLFKQEESLKNIKDSLQQSSGRIDIIHSKKT
AALQSATPVERVKLQEALSQLDFWEKVNKMYKDRQGRFDRSVEKWRRFHYDIKIFNQW
LTEAEQFLRKTQIPENWEHAKYKWYLKELQDGIGQRQTVVRTLNATGEEIIQQSSKTDASIL
QEKLGSLNLRWQEVCKQLSDRKKRLEEQKNILSEFQRDLNEFVLWLEEADNIASIPLEPGK
EQQLKEKLEQVKLLVEELPLRQGILKQLNETGGPVLVSAPISPEEQDKLENKLKQTNLQWI
KVSRALPEKQGEIEAQIKDLGQLEKKLEDLEEQLNHLLLWLSPIRNQLEIYNQPNQEGPFD
VQETEIAVQAKQPDVEEILSKGQHLYKEKPATQPVKRKLEDLSSEWKAVNRLLQELRAKQP
DLAPGLTTIGASPTQTVTLVTQPVVTKETAISKLEMPSSLMLEVPALADFNRAWTELTDWLS
LLDQVIKSQRVMVGDLEDINEMIIKQKATMQDLEQRRPQLEELITAAQNLKNKTSNQEART
IITDRIERIQNQWDEVQEHLQNRRQQLNEMLKDSTQWLEAKEEAEQVLGQARAKLESWKE
GPYTVDAIQKKITETKQLAKDLRQWQTNVDVANDLALKLLRDYSADDTRKVHMITENINAS
WRSIHKRVSEREAALEETHRLLQQFPLDLEKFLAWLTEAETTANVLQDATRKERLLEDSKG
VKELMKQWQDLQGEIEAHTDVYHNLDENSQKILRSLEGSDDAVLLQRRLDNMNFKWSEL
RKKSLNIRSHLEASSDQWKRLHLSLQELLVWLQLKDDELSRQAPIGGDFPAVQKQNDVHR
AFKRELKTKEPVIMSTLETVRIFLTEQPLEGLEKLYQEPRELPPEERAQNVTRLLRKQAEEV
NTEWEKLNLHSADWQRKIDETLERLQELQEATDELDLKLRQAEVIKGSWQPVGDLLIDSL

Figure 7B

QDHLEKVKALRGEIAPLKENVSHVNDLARQLTTLGIQLSPYNLSTLEDLNTRWKLLQVAVE
DRVRQLHEAHRDFGPASQHFLSTSVQGPWERAISPNKVPYYINHETQTTCWDHPKMTELY
QSLADLNNVRFSAYRTAMKLRRLQKALCLDLLSLSAACDALDQHNLKQNDQPMDILQIINC
LTTIYDRLEQEHNNLVNVPLCVDMCLNWLLNVYDTGRTGRIRVLSFKTGIISLCKAHLEDK
YRYLFKQVASSTGFCDQRRLGLLLHDSIQIPRQLGEVASFGGSNIEPSVRSCFQFANNKPEIE
AALFLDWMRLEPQSMVWLPVLHRVAAAETAKHQAKCNICKECPIIGFRYRSLKHFNYDICQ
SCFFSGRVAKGHKMHYPMVEYCTPTTSGEDVRDFAKVLKNKFRTKRYFAKHPRMGYLPV
QTVLEGDNMETPVTLINFWPVDSAPASSPQLSHDDTHSRIEHYASRLAEMENSNGSYLNDS
ISPNESIDDEHLLIQHYCQSLNQDSPLSQPRSPAQILISLESEERGELERILADLEEENRNLQ
AEYDRLKQQHEHKGLSPLPSPPEMMPTSPQSPRDAELIAEAKLLRQHKGRLEARMQILED
HNKQLESQLHRLRQLLEQPQAEAKVNGTTVSSPSTSLQRSDSSQPMLLRVVGSQTSDSMGE
EDLLSPPQDTSTGLEEVMEQLNNSFPSSRGRNTPGKPMREDTM

Figure 8

Human IGF-1 Isoform 4 amino acid sequence

SEQ ID NO 2:
MGKISSLPTQLFKCCFCDFLKVKMHTMSSSHLFYLALCLLTFTSSATAGPETLCGAELVDAL
QFVCGDRGFYFNKPTGYGSSSRRAPQTGIVDECCFRSCDLRRLEMYCAPLKPAKSARSVRA
QRHTDMPKTQKEVHLKNASRGSAGNKNYRM

Figure 9A

DMD Gene Exon 43

| SEQ ID NO 3 | CGACC UGAGC UUUGU UGUAG |
|---|---|
| SEQ ID NO 4 | CGACC UGAGC UUUGU UGUAG ACUAU |
| SEQ ID NO 5 | CCUGA GCUUU GUUGU AGACU AUC |
| SEQ ID NO 6 | CGUUG CACUU UGCAA UGCUG CUG |
| SEQ ID NO 7 | CUGUA GCUUC ACCCU UUCC |
| SEQ ID NO 8 | GAGAG AGCUU CCUGU AGCUU CACC |
| SEQ ID NO 9 | GUCCU UGUAC AUUUU GUUAA CUUUU UC |
| SEQ ID NO 263 | GGA GAG AGC UUC CUG UAG CU |
| SEQ ID NO 264 | UCA CCC UUU CCA CAG GCG UUG CA |
| SEQ ID NO 265 | UGCACUUUGCAAUGCUGCUGUCUUCUUG CUAU |

Figure 9B

| | | | |
|---|---|---|---|
| SEQ ID NO 10 | UCAGCUUCUGUUAGCCACUG | SEQ ID NO 35 | AGCUUCUGUUAGCCACUGAUUAAA |
| SEQ ID NO 11 | UUCAGCUUCUGUUAGCCACU | SEQ ID NO 36 | CAGCUUCUGUUAGCCACUGAUUAAA |
| SEQ ID NO 12 | UUCAGCUUCUGUUAGCCACUG | SEQ ID NO 37 | AGCUUCUGUUAGCCACUGAUUAAA |
| SEQ ID NO 13 | UCAGCUUCUGUUAGCCACUGA | SEQ ID NO 38 | AGCUUCUGUUAGCCACUGAU |
| SEQ ID NO 14 | UUCAGCUUCUGUUAGCCACUGA | SEQ ID NO 39 | GCUUCUGUUAGCCACUGAUU |
| SEQ ID NO 15 | UCAGCUUCUGUUAGCCACUGA | SEQ ID NO 40 | AGCUUCUGUUAGCCACUGAUU |
| SEQ ID NO 16 | UUCAGCUUCUGUUAGCCACUGA | SEQ ID NO 41 | GCUUCUGUUAGCCACUGAUUA |
| SEQ ID NO 17 | UCAGCUUCUGUUAGCCACUGAU | SEQ ID NO 42 | AGCUUCUGUUAGCCACUGAUUA |
| SEQ ID NO 18 | UUCAGCUUCUGUUAGCCACUGAU | SEQ ID NO 43 | GCUUCUGUUAGCCACUGAUUAA |
| SEQ ID NO 19 | UCAGCUUCUGUUAGCCACUGAUU | SEQ ID NO 44 | AGCUUCUGUUAGCCACUGAUUAA |
| SEQ ID NO 20 | UUCAGCUUCUGUUAGCCACUGAUU | SEQ ID NO 45 | GCUUCUGUUAGCCACUGAUUAAA |
| SEQ ID NO 21 | UCAGCUUCUGUUAGCCACUGAUUA | SEQ ID NO 46 | AGCUUCUGUUAGCCACUGAUUAAA |
| SEQ ID NO 22 | UUCAGCUUCUGUUAGCCACUGAUA | SEQ ID NO 47 | GCUUCUGUUAGCCACUGAUUAAA |
| SEQ ID NO 23 | UCAGCUUCUGUUAGCCACUGAUUAA | SEQ ID NO 48 | CCAUUUGUAUUUAGCAUGUUCCC |
| SEQ ID NO 24 | UUCAGCUUCUGUUAGCCACUGAUUAA | SEQ ID NO 49 | AGAUACCAUUUGUAUUUAGC |
| SEQ ID NO 25 | UCAGCUUCUGUUAGCCACUGAUUAAA | SEQ ID NO 50 | GCCAUUUCUCAACAGAUCU |
| SEQ ID NO 26 | UUCAGCUUCUGUUAGCCACUGAUUAAA | SEQ ID NO 51 | GCCAUUUCUCAACAGAUCUGUCA |

Figure 9C

| SEQ ID NO 27 | CAGCUUCUGUUAGCCACUG | SEQ ID NO 52 | AUUCUCAGGAAUUUGUGUCUUUC |
|---|---|---|---|
| SEQ ID NO 28 | CAGCUUCUGUUAGCCACUGAU | SEQ ID NO 53 | UCUCAGGAAUUUGUGUCUUUC |
| SEQ ID NO 29 | AGCUUCUGUUAGCCACUGAUU | SEQ ID NO 54 | GUUCAGCUUCUGUUAGCC |
| SEQ ID NO 30 | CAGCUUCUGUUAGCCACUGAUU | SEQ ID NO 55 | CUGAUUAAAUAUCUUUAUAU C |
| SEQ ID NO 31 | AGCUUCUGUUAGCCACUGAUUA | SEQ ID NO 56 | GCCGCCAUUUCUCAACAG |
| SEQ ID NO 32 | CAGCUUCUGUUAGCCACUGAUUA | SEQ ID NO 57 | GUAUUUAGCAUGUUCCCA |
| SEQ ID NO 33 | AGCUUCUGUUAGCCACUGAUUAA | SEQ ID NO 58 | CAGGAAUUUGUGUCUUUC |
| SEQ ID NO 34 | CAGCUUCUGUUAGCCACUGAUUAA | SEQ ID NO 267 | UUU GUG UCU UUC UGA GAA AC |
| SEQ ID NO 266 | UCAUAAUGAAAACGCCGCCAUUUCUCAACAGAUCU | SEQ ID NO 268 | UUUAGCAUGUUCCCAAUUCUCAGGAAUUUG |

Figure 9D

DMD Gene Exon 45

| SEQ ID NO | Sequence | SEQ ID NO | Sequence |
|---|---|---|---|
| SEQ ID NO 59 | UUUGCCGCUGCCCAAUGCCAUCCUG | SEQ ID NO 89 | GUUGCAUUCAAUGUUCUGACAACAG |
| SEQ ID NO 60 | AUUCAAUGUUCUGACAACAGUUUGC | SEQ ID NO 90 | UUGCAUUCAAUGUUCUGACAACAGU |
| SEQ ID NO 61 | CCAGUUGCAUUCAAUGUUCUGACAA | SEQ ID NO 91 | UGCAUUCAAUGUUCUGACAACAGUU |
| SEQ ID NO 62 | CAGUUGCAUUCAAUGUUCUGAC | SEQ ID NO 92 | GCAUUCAAUGUUCUGACAACAGUUU |
| SEQ ID NO 63 | AGUUGCAUUCAAUGUUCUGA | SEQ ID NO 93 | CAUUCAAUGUUCUGACAACAGUUUG |
| SEQ ID NO 64 | GAUUGCUGAAUUAUUUCUUCC | SEQ ID NO 94 | AUUCAAUGUUCUGACAACAGUUUGC |
| SEQ ID NO 65 | GAUUGCUGAAUUAUUUCUUCCCCAG | SEQ ID NO 95 | UCAAUGUUCUGACAACAGUUUGCCG |
| SEQ ID NO 66 | AUUGCUGAAUUAUUUCUUCCCCAGU | SEQ ID NO 96 | CAAUGUUCUGACAACAGUUUGCCGC |
| SEQ ID NO 67 | UUGCUGAAUUAUUUCUUCCCCAGUU | SEQ ID NO 97 | AAUGUUCUGACAACAGUUUGCCGCU |
| SEQ ID NO 68 | UGCUGAAUUAUUUCUUCCCCAGUUG | SEQ ID NO 98 | AUGUUCUGACAACAGUUUGCCGCUG |
| SEQ ID NO 69 | GCUGAAUUAUUUCUUCCCCAGUUGC | SEQ ID NO 99 | UGUUCUGACAACAGUUUGCCGCUGC |
| SEQ ID NO 70 | CUGAAUUAUUUCUUCCCCAGUUGCA | SEQ ID NO 100 | GUUCUGACAACAGUUUGCCGCUGCC |
| SEQ ID NO 71 | UGAAUUAUUUCUUCCCCAGUUGCAU | SEQ ID NO 101 | UUCUGACAACAGUUUGCCGCUGCCC |
| SEQ ID NO 72 | GAAUUAUUUCUUCCCCAGUUGCAUU | SEQ ID NO 102 | UCUGACAACAGUUUGCCGCUGCCCA |
| SEQ ID NO 73 | AAUUAUUUCUUCCCCAGUUGCAUUC | SEQ ID NO 103 | CUGACAACAGUUUGCCGCUGCCCAA |
| SEQ ID NO 74 | AUUAUUUCUUCCCCAGUUGCAUUCA | SEQ ID NO 104 | UGACAACAGUUUGCCGCUGCCCAAU |
| SEQ ID NO 75 | UUAUUUCUUCCCCAGUUGCAUUCAA | SEQ ID NO 105 | GACAACAGUUUGCCGCUGCCCAAUG |
| SEQ ID NO 76 | UAUUUCUUCCCCAGUUGCAUUCAAU | SEQ ID NO 106 | ACAACAGUUUGCCGCUGCCCAAUGC |
| SEQ ID NO 77 | AUUUCUUCCCCAGUUGCAUUCAAUG | SEQ ID NO 107 | CAACAGUUUGCCGCUGCCCAAUGCC |

Figure 9E

| SEQ ID NO 78 | UUUCUUCCCCAGUUGCAUUCAAUGU | SEQ ID NO 108 | AACAGUUUGCCGCUGCCCAAUGCCA |
|---|---|---|---|
| SEQ ID NO 79 | UUCUUCCCCAGUUGCAUUCAAUGUU | SEQ ID NO 109 | ACAGUUUGCCGCUGCCCAAUGCCAU |
| SEQ ID NO 80 | UCUUCCCCAGUUGCAUUCAAUGUUC | SEQ ID NO 110 | CAGUUUGCCGCUGCCCAAUGCCAUC |
| SEQ ID NO 81 | CUUCCCCAGUUGCAUUCAAUGUUCU | SEQ ID NO 111 | AGUUUGCCGCUGCCCAAUGCCAUCC |
| SEQ ID NO 82 | UUCCCCAGUUGCAUUCAAUGUUCUG | SEQ ID NO 112 | GUUUGCCGCUGCCCAAUGCCAUCCU |
| SEQ ID NO 83 | UCCCCAGUUGCAUUCAAUGUUCUGA | SEQ ID NO 113 | UUUGCCGCUGCCCAAUGCCAUCCUG |
| SEQ ID NO 84 | CCCCAGUUGCAUUCAAUGUUCUGAC | SEQ ID NO 114 | UUGCCGCUGCCCAAUGCCAUCCUGG |
| SEQ ID NO 85 | CCCAGUUGCAUUCAAUGUUCUGACA | SEQ ID NO 115 | UGCCGCUGCCCAAUGCCAUCCUGGA |
| SEQ ID NO 86 | CCAGUUGCAUUCAAUGUUCUGACAA | SEQ ID NO 116 | GCCGCUGCCCAAUGCCAUCCUGGAG |
| SEQ ID NO 87 | CAGUUGCAUUCAAUGUUCUGACAAC | SEQ ID NO 117 | CCGCUGCCCAAUGCCAUCCUGGAGU |
| SEQ ID NO 88 | AGUUGCAUUCAAUGUUCUGACAACA | SEQ ID NO 118 | CGCUGCCCAAUGCCAUCCUGGAGUU |
| SEQ ID NO 269 | UCC UGU AGA AUA CUG GCA UC | SEQ ID NO 272 | UGU UUU UGA GGA UUG CUG AA |
| SEQ ID NO 270 | UGC AGA CCU CCU GCC ACC GCA GAU UCA | SEQ ID NO 273 | UGUUCUGACAACAGUUUGCCGCUGCCCAAUGCCAUCCUGG |
| SEQ ID NO 271 | UUGCAGACCUCCUGCCACCGCAGAUUCAGGCUUC | | |

Figure 9F

DMD Gene Exon 46

| SEQ ID NO 119 | GCUUUUCUUUUAGUUGCUGCUCUUU | SEQ ID NO 147 | AGGUUCAAGUGGGAUACUAGCAAUG |
|---|---|---|---|
| SEQ ID NO 120 | CUUUUCUUUUAGUUGCUGCUCUUUU | SEQ ID NO 148 | GGUUCAAGUGGGAUACUAGCAAUGU |
| SEQ ID NO 121 | UUUUCUUUUAGUUGCUGCUCUUUUC | SEQ ID NO 149 | GUUCAAGUGGGAUACUAGCAAUGUU |
| SEQ ID NO 122 | UUUCUUUUAGUUGCUGCUCUUUUCC | SEQ ID NO 150 | UUCAAGUGGGAUACUAGCAAUGUUA |
| SEQ ID NO 123 | UUCUUUUAGUUGCUGCUCUUUUCCA | SEQ ID NO 151 | UCAAGUGGGAUACUAGCAAUGUUAU |
| SEQ ID NO 124 | UCUUUUAGUUGCUGCUCUUUUCCAG | SEQ ID NO 152 | CAAGUGGGAUACUAGCAAUGUUAUC |
| SEQ ID NO 125 | CUUUUAGUUGCUGCUCUUUUCCAGG | SEQ ID NO 153 | AAGUGGGAUACUAGCAAUGUUAUCU |
| SEQ ID NO 126 | UUUUAGUUGCUGCUCUUUUCCAGGU | SEQ ID NO 154 | AGUGGGAUACUAGCAAUGUUAUCUG |
| SEQ ID NO 127 | UUUAGUUGCUGCUCUUUUCCAGGUU | SEQ ID NO 155 | GUGGGAUACUAGCAAUGUUAUCUGC |
| SEQ ID NO 128 | UUAGUUGCUGCUCUUUUCCAGGUUC | SEQ ID NO 156 | UGGGAUACUAGCAAUGUUAUCUGCU |
| SEQ ID NO 129 | UAGUUGCUGCUCUUUUCCAGGUUCA | SEQ ID NO 157 | GGGAUACUAGCAAUGUUAUCUGCUU |
| SEQ ID NO 130 | AGUUGCUGCUCUUUUCCAGGUUCAA | SEQ ID NO 158 | GGAUACUAGCAAUGUUAUCUGCUUC |
| SEQ ID NO 131 | GUUGCUGCUCUUUUCCAGGUUCAAG | SEQ ID NO 159 | GAUACUAGCAAUGUUAUCUGCUUCC |
| SEQ ID NO 132 | UUGCUGCUCUUUUCCAGGUUCAAGU | SEQ ID NO 160 | AUACUAGCAAUGUUAUCUGCUUCCU |
| SEQ ID NO 133 | UGCUGCUCUUUUCCAGGUUCAAGUG | SEQ ID NO 161 | UACUAGCAAUGUUAUCUGCUUCCUC |
| SEQ ID NO 134 | GCUGCUCUUUUCCAGGUUCAAGUGG | SEQ ID NO 162 | ACUAGCAAUGUUAUCUGCUUCCUCC |
| SEQ ID NO 135 | CUGCUCUUUUCCAGGUUCAAGUGGG | SEQ ID NO 163 | CUAGCAAUGUUAUCUGCUUCCUCCA |
| SEQ ID NO 136 | UGCUCUUUUCCAGGUUCAAGUGGGA | SEQ ID NO 164 | UAGCAAUGUUAUCUGCUUCCUCCAA |

Figure 9G

| SEQ ID NO 137 | GCUCUUUUCCAGGUUCAAGUGGGAC | SEQ ID NO 165 | AGCAAUGUUAUCUGCUUCCUCCAAC |
|---|---|---|---|
| SEQ ID NO 138 | CUCUUUUCCAGGUUCAAGUGGGAUA | SEQ ID NO 166 | GCAAUGUUAUCUGCUUCCUCCAACC |
| SEQ ID NO 139 | UCUUUUCCAGGUUCAAGUGGGAUAC | SEQ ID NO 167 | CAAUGUUAUCUGCUUCCUCCAACCA |
| SEQ ID NO 140 | CUUUUCCAGGUUCAAGUGGGAUACU | SEQ ID NO 168 | AAUGUUAUCUGCUUCCUCCAACCAU |
| SEQ ID NO 141 | UUUUCCAGGUUCAAGUGGGAUACUA | SEQ ID NO 169 | AUGUUAUCUGCUUCCUCCAACCAUA |
| SEQ ID NO 142 | UUUCCAGGUUCAAGUGGGAUACUAG | SEQ ID NO 170 | UGUUAUCUGCUUCCUCCAACCAUAA |
| SEQ ID NO 143 | UUCCAGGUUCAAGUGGGAUACUAGC | SEQ ID NO 171 | GUUAUCUGCUUCCUCCAACCAUAAA |
| SEQ ID NO 144 | UCCAGGUUCAAGUGGGAUACUAGCA | SEQ ID NO 172 | GCUGCUCUUUUCCAGGUUC |
| SEQ ID NO 145 | CCAGGUUCAAGUGGGAUACUAGCAA | SEQ ID NO 173 | UCUUUUCCAGGUUCAAGUGG |
| SEQ ID NO 146 | CAGGUUCAAGUGGGAUACUAGCAAU | SEQ ID NO 174 | AGGUUCAAGUGGGAUACUA |
| SEQ ID NO 274 | CUCUUUUCCAGGUUCAAGUGGGAUACUAGC | SEQ ID NO 276 | UAUUCUUUUGUUCUUCUAGCCUGGAGAAAG |
| SEQ ID NO 275 | CAAGCUUUUCUUUUAGUUGCUGCUCUUUUCC | SEQ ID NO 277 | CUGCUUCCUCCAACCAUAAAACAAAUUC |

Figure 9H

DMD Gene Exon 50

| SEQ ID NO 175 | CUCAGCUCUUGAAGUAAACG |
|---|---|
| SEQ ID NO 176 | CCUCAGCUCUUGAAGUAAAC |
| SEQ ID NO 177 | CCUCAGCUCUUGAAGUAAACG |
| SEQ ID NO 178 | AUAGUGGUCAGUCCAGGAGCU |
| SEQ ID NO 179 | CAGUC CAGGA GCUAG GUCAGG |
| SEQ ID NO 180 | UAGUGGUCAGUCCAGGAGCUAGGUC |
| SEQ ID NO 278 | CCACUCAGAGCUCAGAUCUUCUAACUUCC |
| SEQ ID NO 279 | CUUCCACUCAGAGCUCAGAUCUUCUAA |
| SEQ ID NO 280 | CAGUCCAGGAGCUAGGUCAGGCUGCUUUGC |
| SEQ ID NO 281 | UCUUGAAGUAAACGGUUUACCGCCUUCCACUCAGAGC |

Figure 9I

DMD Gene Exon 51

| SEQ ID NO 181 | AGAGCAGGUACCUCCAACAUCAAGG | SEQ ID NO 203 | UCAAGGAAGAUGGCAUUUCUAGUUU |
|---|---|---|---|
| SEQ ID NO 182 | GAGCAGGUACCUCCAACAUCAAGGA | SEQ ID NO 204 | UCAAGGAAGAUGGCAUUUCU |
| SEQ ID NO 183 | AGCAGGUACCUCCAACAUCAAGGAA | SEQ ID NO 205 | CAAGGAAGAUGGCAUUUCUAGUUUG |
| SEQ ID NO 184 | GCAGGUACCUCCAACAUCAAGGAAG | SEQ ID NO 206 | AAGGAAGAUGGCAUUUCUAGUUUGG |
| SEQ ID NO 185 | CAGGUACCUCCAACAUCAAGGAAGA | SEQ ID NO 207 | AGGAAGAUGGCAUUUCUAGUUUGGA |
| SEQ ID NO 186 | AGGUACCUCCAACAUCAAGGAAGAU | SEQ ID NO 208 | GGAAGAUGGCAUUUCUAGUUUGGAG |
| SEQ ID NO 187 | GGUACCUCCAACAUCAAGGAAGAUG | SEQ ID NO 209 | GAAGAUGGCAUUUCUAGUUUGGAGA |
| SEQ ID NO 188 | GUACCUCCAACAUCAAGGAAGAUGG | SEQ ID NO 210 | AAGAUGGCAUUUCUAGUUUGGAGAU |
| SEQ ID NO 189 | UACCUCCAACAUCAAGGAAGAUGGC | SEQ ID NO 211 | AGAUGGCAUUUCUAGUUUGGAGAUG |
| SEQ ID NO 190 | ACCUCCAACAUCAAGGAAGAUGGCA | SEQ ID NO 212 | GAUGGCAUUUCUAGUUUGGAGAUGG |
| SEQ ID NO 191 | CCUCCAACAUCAAGGAAGAUGGCAU | SEQ ID NO 213 | AUGGCAUUUCUAGUUUGGAGAUGGC |
| SEQ ID NO 192 | CUCCAACAUCAAGGAAGAUGGCAUU | SEQ ID NO 214 | UGGCAUUUCUAGUUUGGAGAUGGCA |
| SEQ ID NO 193 | CUCCAACAUCAAGGAAGAUGGCAUUUCUAG | SEQ ID NO 215 | GGCAUUUCUAGUUUGGAGAUGGCAG |
| SEQ ID NO 194 | UCCAACAUCAAGGAAGAUGGCAUUU | SEQ ID NO 216 | GCAUUUCUAGUUUGGAGAUGGCAGU |
| SEQ ID NO 195 | CCAACAUCAAGGAAGAUGGCAUUUC | SEQ ID NO 217 | CAUUUCUAGUUUGGAGAUGGCAGUU |
| SEQ ID NO 196 | CAACAUCAAGGAAGAUGGCAUUUCU | SEQ ID NO 218 | AUUUCUAGUUUGGAGAUGGCAGUUU |
| SEQ ID NO 197 | AACAUCAAGGAAGAUGGCAUUUCUA | SEQ ID NO 219 | UUUCUAGUUUGGAGAUGGCAGUUUC |
| SEQ ID NO 198 | ACAUCAAGGAAGAUGGCAUUUCUAG | SEQ ID NO 220 | UUCUAGUUUGGAGAUGGCAGUUUCC |

Figure 9J

| SEQ ID NO 199 | ACAUCAAGGAAGAUGGCAUUUCUAGUUUGG | | |
|---|---|---|---|
| SEQ ID NO 200 | ACAUCAAGGAAGAUGGCAUUUCUAG | | |
| SEQ ID NO 201 | CAUCAAGGAAGAUGGCAUUUCUAGU | | |
| SEQ ID NO 202 | AUCAAGGAAGAUGGCAUUUCUAGUU | | |

Figure 9K

DMD Gene Exon 52

| | | | |
|---|---|---|---|
| SEQ ID NO 221 | CCUCUUGAUUGCUGGUCUUGUUUUU | SEQ ID NO 250 | UUUUGGGCAGCGGUAAUGAGUUCUU |
| SEQ ID NO 222 | CUCUUGAUUGCUGGUCUUGUUUUUC | SEQ ID NO 251 | UUUGGGCAGCGGUAAUGAGUUCUUC |
| SEQ ID NO 223 | UCUUGAUUGCUGGUCUUGUUUUUCA | SEQ ID NO 252 | UUGGGCAGCGGUAAUGAGUUCUUCC |
| SEQ ID NO 224 | CUUGAUUGCUGGUCUUGUUUUUCAA | SEQ ID NO 253 | UGGGCAGCGGUAAUGAGUUCUUCCA |
| SEQ ID NO 225 | UUGAUUGCUGGUCUUGUUUUUCAAA | SEQ ID NO 254 | GGGCAGCGGUAAUGAGUUCUUCCAA |
| SEQ ID NO 226 | UGAUUGCUGGUCUUGUUUUUCAAAU | SEQ ID NO 255 | GGCAGCGGUAAUGAGUUCUUCCAAC |
| SEQ ID NO 227 | GAUUGCUGGUCUUGUUUUUCAAAUU | SEQ ID NO 256 | GCAGCGGUAAUGAGUUCUUCCAACU |
| SEQ ID NO 228 | AUUGCUGGUCUUGUUUUUCAAAUUU | SEQ ID NO 257 | CAGCGGUAAUGAGUUCUUCCAACUG |
| SEQ ID NO 229 | UUGCUGGUCUUGUUUUUCAAAUUUU | SEQ ID NO 258 | AGCGGUAAUGAGUUCUUCCAACUGG |
| SEQ ID NO 230 | UGCUGGUCUUGUUUUUCAAAUUUUG | SEQ ID NO 259 | GCGGUAAUGAGUUCUUCCAACUGGG |
| SEQ ID NO 231 | GCUGGUCUUGUUUUUCAAAUUUUGG | SEQ ID NO 260 | CGGUAAUGAGUUCUUCCAACUGGGG |
| SEQ ID NO 232 | CUGGUCUUGUUUUUCAAAUUUUGGG | SEQ ID NO 261 | GGUAAUGAGUUCUUCCAACUGGGGA |
| SEQ ID NO 233 | UGGUCUUGUUUUUCAAAUUUUGGGC | SEQ ID NO 262 | GUAAUGAGUUCUUCCAACUGGGGAC |
| SEQ ID NO 234 | GGUCUUGUUUUUCAAAUUUUGGGCA | SEQ ID NO 263 | UAAUGAGUUCUUCCAACUGGGGACG |
| SEQ ID NO 235 | GUCUUGUUUUUCAAAUUUUGGGCAG | SEQ ID NO 264 | AAUGAGUUCUUCCAACUGGGGACGC |
| SEQ ID NO 236 | UCUUGUUUUUCAAAUUUUGGGCAGC | SEQ ID NO 265 | AUGAGUUCUUCCAACUGGGGACGCC |
| SEQ ID NO 237 | CUUGUUUUUCAAAUUUUGGGCAGCG | SEQ ID NO 266 | UGAGUUCUUCCAACUGGGGACGCCU |
| SEQ ID NO 238 | UUGUUUUUCAAAUUUUGGGCAGCGG | SEQ ID NO 267 | GAGUUCUUCCAACUGGGGACGCCUC |

Figure 9L

| SEQ ID NO 239 | UGUUUUUCAAAUUUUGGGCAGCGGU | SEQ ID NO 268 | AGUUCUUCCAACUGGGGACGCCUCU |
|---|---|---|---|
| SEQ ID NO 240 | GUUUUUCAAAUUUUGGGCAGCGGUA | SEQ ID NO 269 | GUUCUUCCAACUGGGGACGCCUCUG |
| SEQ ID NO 241 | UUUUUCAAAUUUUGGGCAGCGGUAA | SEQ ID NO 270 | UUCUUCCAACUGGGGACGCCUCUGU |
| SEQ ID NO 242 | UUUUCAAAUUUUGGGCAGCGGUAAU | SEQ ID NO 271 | UCUUCCAACUGGGGACGCCUCUGUU |
| SEQ ID NO 243 | UUUCAAAUUUUGGGCAGCGGUAAUG | SEQ ID NO 272 | CUUCCAACUGGGGACGCCUCUGUUC |
| SEQ ID NO 244 | UUCAAAUUUUGGGCAGCGGUAAUGA | SEQ ID NO 273 | UUCCAACUGGGGACGCCUCUGUUCC |
| SEQ ID NO 245 | UCAAAUUUUGGGCAGCGGUAAUGAG | SEQ ID NO 274 | GAUUG CUGGU CUUGU UUUUC |
| SEQ ID NO 246 | CAAAUUUUGGGCAGCGGUAAUGAGU | SEQ ID NO 275 | CCUCU UGAUU GCUGG UCUUG |
| SEQ ID NO 247 | AAAUUUUGGGCAGCGGUAAUGAGUU | SEQ ID NO 276 | GGUAA UGAGU UCUUC CAACU GG |
| SEQ ID NO 248 | AAUUUUGGGCAGCGGUAAUGAGUUC | SEQ ID NO 277 | ACUGG GGACG CCUCU GUUCC |
| SEQ ID NO 249 | AUUUUGGGCAGCGGUAAUGAGUUCU | SEQ ID NO 283 | ACUGGGGACGCCUCUGUUCCA |
| SEQ ID NO 282 | UCCAACUGGGGACGCCUCUGUUCC AAAUCC | SEQ ID NO 284 | CCGUAAUGAUUGUUCUAGCC |

Figure 9M

DMD Gene Exon 53

| SEQ ID NO 250 | CCAUUGUGUUGAAUCCUUUAACAUU |
|---|---|
| SEQ ID NO 251 | CCAUUGUGUUGAAUCCUUUAAC |
| SEQ ID NO 252 | AUUGUGUUGAAUCCUUUAAC |
| SEQ ID NO 253 | CCUGUCCUAAGACCUGCUCA |
| SEQ ID NO 254 | CUUUUGGAUUGCAUCUACUGUAUAG |
| SEQ ID NO 255 | CAUUCAACUGUUGCCUCCGGUUCUG |
| SEQ ID NO 256 | CUGUUGCCUCCGGUUCUGAAGGUG |
| SEQ ID NO 257 | CAUUCAACUGUUGCCUCCGGUUCUGAAGGUG |
| SEQ ID NO 258 | CUGAAGGUGUUCUUGUACUUCAUCC |
| SEQ ID NO 259 | UGUAUAGGGACCCUCCUUCCAUGACUC |
| SEQ ID NO 260 | AUCCCACUGAUUCUGAAUUC |
| SEQ ID NO 261 | UUGGCUCUGGCCUGUCCUAAGA |
| SEQ ID NO 262 | AAGACCUGCUCAGCUUCUUCCUUAGCUUCCAGCCA |

MEANS AND METHODS FOR COUNTERACTING MUSCLE DISORDERS

This application is a continuation application of and claims priority to PCT/NL2008/050673 filed Oct. 27, 2008, EPO Application No. 07119351.0 filed Oct. 26, 2007, and U.S. Provisional Application No. 61/000,670 filed Oct. 26, 2007, the contents of which are hereby incorporated in their entirety by this reference.

The invention relates to the fields of molecular biology and medicine. A muscle disorder is a disease that usually has a significant impact on the life of an individual. A muscle disorder can either have a genetic cause or a non-genetic cause. An important group of muscle diseases with a genetic cause are Becker Muscular Dystrophy (BMD) and Duchenne Muscular Dystrophy (DMD). These disorders are caused by defects in a gene for a muscle protein.

Becker Muscular Dystrophy and Duchenne Muscular Dystrophy are genetic muscular dystrophies with a relatively high incidence. In both Duchenne and Becker muscular dystrophy the muscle protein dystrophin is affected. In Duchenne dystrophin is absent, whereas in Becker some dystrophin is present but its production is most often not sufficient and/or the dystrophin present is abnormally formed. Both diseases are associated with recessive X-linked inheritance. DMD results from a frameshift mutation in the DMD gene. The frameshift in the DMD gene results in the production of a truncated non-functional dystrophin protein, resulting in progressive muscle wasting and weakness. BMD occurs as a mutation does not cause a frame-shift in the DMD gene. As in BMD some dystrophin is present in contrast to DMD where dystrophin is absent, BMD has less severe symptoms then DMD. The onset of DMD is earlier than BMD. DMD usually manifests itself in early childhood, BMD in the teens or in early adulthood. The progression of BMD is slower and less predictable than DMD. Patients with BMD can survive into mid to late adulthood. Patients with DMD rarely survive beyond their thirties.

Dystrophin plays an important structural role in the muscle fiber, connecting the extracellular matrix and the cytoskeleton. The N-terminal region binds actin, whereas the C-terminal end is part of the dystrophin glycoprotein complex (DGC), which spans the sarcolemma. In the absence of dystrophin, mechanical stress leads to sarcolemmal ruptures, causing an uncontrolled influx of calcium into the muscle fiber interior, thereby triggering calcium-activated proteases and fiber necrosis.

For most genetic muscular dystrophies no clinically applicable and effective therapies are currently available. Exon skipping techniques are nowadays explored in order to combat genetic muscular dystrophies. Promising results have recently been reported by us and others on a genetic therapy aimed at restoring the reading frame of the dystrophin pre-mRNA in cells from the mdx mouse and DMD patients[1-11]. By the targeted skipping of a specific exon, a DMD phenotype (lacking dystrophin) is converted into a milder BMD phenotype (partly to largely functional dystrophin). The skipping of an exon is preferably induced by the binding of antisense oligoribonucleotides (AONs) targeting either one or both of the splice sites, or exon-internal sequences. Since an exon will only be included in the mRNA when both the splice sites are recognised by the spliceosome complex, splice sites are obvious targets for AONs. Alternatively, or additionally, one or more AONs are used which are specific for at least part of one or more exonic sequences. Using exon-internal AONs specific for an exon 46 sequence, we were previously able to modulate the splicing pattern in cultured myotubes from two different DMD patients with an exon 45 deletion[11]. Following AON treatment, exon 46 was skipped, which resulted in a restored reading frame and the induction of dystrophin synthesis in at least 75% of the cells. We have recently shown that exon skipping can also efficiently be induced in human control and patient muscle cells for 39 different DMD exons using exon-internal AONs[1,2,11-15].

Hence, exon skipping techniques applied on the dystrophin gene result in the generation of at least partially functional—albeit shorter—dystrophin protein in DMD patients. Since DMD is caused by a dysfunctional dystrophin protein, it would be expected that the symptoms of DMD are sufficiently alleviated once a DMD patient has been provided with functional dystrophin protein. However, the present invention provides the insight that, even though exon skipping techniques are capable of inducing dystrophin synthesis, DMD symptom(s) is/are still further alleviated by administering to a DMD patient an adjunct compound for reducing inflammation, preferably for reducing muscle tissue inflammation, and/or an adjunct compound for improving muscle fiber function, integrity and/or survival. According to the present invention, even when a dystrophin protein deficiency has been restored in a DMD patient, the presence of tissue inflammation and damaged muscle cells still continues to contribute to the symptoms of DMD. Hence, even though the cause of DMD—i.e. a dysfunctional dystrophin protein—is alleviated, treatment of DMD is still further improved by additionally using an adjunct therapy according to the present invention. Furthermore, the present invention provides the insight that a reduction of inflammation does not result in significant reduction of AON uptake by muscle cells. This is surprising because, in general, inflammation enhances the trafficking of cells, blood and other compounds. As a result, AON uptake/delivery is also enhanced during inflammation. Hence, before the present invention it would be expected that an adjunct therapy counteracting inflammation involves the risk of negatively influencing AON therapy. This, however, appears not to be the case.

The present invention therefore provides a method for alleviating one or more symptom(s) of Duchenne Muscular Dystrophy or Becker Muscular Dystrophy in an individual, the method comprising:

administering to said individual a compound for providing said individual with a (at least partially) functional dystrophin protein, and administering to said individual an adjunct compound for reducing inflammation, preferably for reducing muscle tissue inflammation, and/or an adjunct compound for improving muscle fiber function, integrity and/or survival.

In another preferred embodiment the method for alleviating one or more symptom(s) of Duchenne Muscular Dystrophy or Becker Muscular Dystrophy in an individual comprises administering to said individual an adjunct compound for reducing inflammation, preferably for reducing muscle tissue inflammation, and/or an adjunct compound for improving muscle fiber function, integrity and/or survival.

It has surprisingly been found that the skipping frequency of a dystrophin exon from a pre-mRNA comprising said exon, when using an oligonucleotide directed toward the exon or to one or both splice sites of said exon, is enhanced if cells expressing said pre-mRNA are also provided with an adjunct compound for reducing inflammation, preferably for reducing muscle tissue inflammation, and/or an adjunct compound for improving muscle fiber function, integrity and/or survival. The enhanced skipping frequency also increases the level of functional dystrophin protein produced in a muscle cell of a DMD or BMD individual.

The present invention further provides a method for enhancing skipping of an exon from a dystrophin pre-mRNA in cells expressing said pre-mRNA, said method comprising
contacting said pre-mRNA in said cells with an oligonucleotide for skipping said exon and,
contacting said cells with an adjunct compound for reducing inflammation, preferably for reducing muscle tissue inflammation, and/or an adjunct compound for improving muscle fiber function, integrity and/or survival.

As Duchenne and Becker muscular dystrophy have a pronounced phenotype in muscle cells, it is preferred that said cells are muscle cells. Preferably said cells comprise a gene encoding a mutant dystrophin protein. Preferably said cells are cells of an individual suffering from DMD or BMD.

The present invention further provides a method for enhancing skipping of an exon from a dystrophin pre-mRNA in cells expressing said pre-mRNA in an individual suffering from Duchenne Muscular Dystrophy or Becker Muscular Dystrophy, the method comprising:
administering to said individual a compound for providing said individual with a (at least partially) functional dystrophin protein, and
administering to said individual an adjunct compound for reducing inflammation, preferably for reducing muscle tissue inflammation, and/or an adjunct compound for improving muscle fiber function, integrity and/or survival An individual is provided with a functional dystrophin protein in various ways. In one embodiment an exon skipping technique is applied. However, alternative methods are available, such as for instance stop codon suppression by gentamycin or PTC124[16,17] (also known as 3-(5-(2-fluorophenyl)-1,2,4-oxadiazol-3-yl)benzoic acid), and/or adeno-associated virus (AAV)-mediated gene delivery of a functional mini- or micro-dystrophin gene[18-20]. PTC124™ is a registered trademark of PTC Therapeutics, Inc. South Plainfield, N.J.

As defined herein, a functional dystrophin is preferably a wild type dystrophin corresponding to a protein having the amino acid sequence as identified in SEQ ID NO: 1. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO:1. In other words, a functional dystrophin is a dystrophin which exhibits at least to some extent an activity of a wild type dystrophin "At least to some extent" preferably means at least 30%, 40%, 50%, 60%, 70%, 80%, 90%, 95% or 100% of a corresponding activity of a wild type functional dystrophin. In this context, an activity of a functional dystrophin is preferably binding to actin and to the dystrophin-associated glycoprotein complex (DGC)[56]. Binding of dystrophin to actin and to the DGC complex may be visualized by either co-immunoprecipitation using total protein extracts or immunofluorescence analysis of cross-sections, from a biopsy of a muscle suspected to be dystrophic, as known to the skilled person.

Individuals suffering from Duchenne muscular dystrophy typically have a mutation in the gene encoding dystrophin that prevent synthesis of the complete protein, i.e of a premature stop prevents the synthesis of the C-terminus. In Becker muscular dystrophy the dystrophin gene also comprises a mutation compared tot the wild type but the mutation does typically not include a premature stop and the C-terminus is typically synthesized. As a result a functional dystrophin protein is synthesized that has at least the same activity in kind as the wild type protein, not although not necessarily the same amount of activity. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin[56]. Exon—skipping for the treatment of DMD is typically directed to overcome a premature stop in the pre-mRNA by skipping an exon in the rod-domain shaped domain to correct the reading frame and allow synthesis of remainder of the dystrophin protein including the C-terminus, albeit that the protein is somewhat smaller as a result of a smaller rod domain. In a preferred embodiment, an individual having DMD and being treated by a method as defined herein will be provided a dystrophin which exhibits at least to some extent an activity of a wild type dystrophin. More preferably, if said individual is a Duchennes patient or is suspected to be a Duchennes patient, a functional dystrophin is a dystrophin of an individual having BMD: typically said dystrophin is able to interact with both actin and the DGC, but its central rod shaped domain may be shorter than the one of a wild type dystrophin (Aartsma-Rus et al (2006, ref 56). The central rod domain of wild type dystrophin comprises 24 spectrin-like repeats[56]. For example, a central rod shaped domain of a dystrophin as provided herein may comprise 5 to 23, 10 to 22 or 12 to 18 spectrin-like repeats as long as it can bind to actin and to DGC.

Alleviating one or more symptom(s) of Duchenne Muscular Dystrophy or Becker Muscular Dystrophy in an individual in a method of the invention may be assessed by any of the following assays: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (2008, ref 58) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using a method of the invention. Detectable improvement or prolongation is preferably a statistically significant improvement or prolongation as described in Hodgetts et al (2006, ref 57). Alternatively, the alleviation of one or more symptom(s) of Duchenne Muscular Dystrophy or Becker Muscular Dystrophy may be assessed by measuring an improvement of a muscle fiber function, integrity and/or survival as later defined herein.

An adjunct compound for reducing inflammation comprises any therapy which is capable of at least in part reducing inflammation, preferably inflammation caused by damaged muscle cells. Said adjunct compound is most preferably capable of reducing muscle tissue inflammation. Inflammation is preferably assessed by detecting an increase in the number of infiltrating immune cells such as neutrophils and/or mast cells and/or dendritic cells and/or lymphocytes in muscle tissue suspected to be dystrophic. This assessment is preferably carried out in cross-sections of a biopsy[57] of muscle tissue suspected to be dystrophic after having specifically stained immune cells as identified above. The quantification is preferably carried out under the microscope. Reducing inflammation is therefore preferably assessed by detecting a decrease in the number of immune cells in a cross-section of muscle tissue suspected to be dystrophic. Detecting a decrease preferably means that the number of at least one sort of immune cells as identified above is decreased of at least 1%, 2%, 3%, 5%, 7%, 10%, 12%, 15%, 17%, 20%, 30%, 40%, 50%, 60%, 70%, 80%, 90% or more compared to the number of a corresponding immune cell in a same individual before treatment. Most preferably, no infiltrating immune cells are detected in cross-sections of said biopsy.

An adjunct compound for improving muscle fiber function, integrity and/or survival comprises any therapy which is capable of measurably enhancing muscle fiber function, integrity and/or survival as compared to an otherwise similar situation wherein said adjunct compound is not present. The improvement of muscle fiber function, integrity and/or survival may be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in 57. A detectable decrease in creatine kinase may mean a decrease of 5%, 10%, 20%, 30%, 40%, 50%, 60%, 70%, 80%, 90% or more compared to the concentration of creatine kinase in a same individual before treatment.

A detectable decrease of necrosis of muscle fibers is preferably assessed in a muscle biopsy, more preferably as described in 57 using biopsy cross-sections. A detectable decrease of necrosis may be a decrease of 5%, 10%, 20%, 30%, 40%, 50%, 60%, 70%, 80%, 90% or more of the area wherein necrosis has been identified using biopsy cross-sections. The decrease is measured by comparison to the necrosis as assessed in a same individual before treatment.

A detectable increase of the homogeneity of the diameter of a muscle fiber is preferably assessed in a muscle biopsy cross-section, more preferably as described in 57.

A treatment in a method according to the invention is about at least one week, about at least one month, about at least several months, about at least one year, about at least 2, 3, 4, 5, 6 years or more.

In one embodiment an adjunct compound for increasing turnover of damaged muscle cells is used. An adjunct compound for increasing turnover of damaged muscle cells comprises any therapy which is capable of at least in part inducing and/or increasing turnover of damaged muscle cells. Damaged muscle cells are muscle cells which have significantly less clinically measurable functionality than a healthy, intact muscle cell. In the absence of dystrophin, mechanical stress leads to sarcolemmal ruptures, causing an uncontrolled influx of calcium into the muscle fiber interior, thereby triggering calcium-activated proteases and fiber necrosis, resulting in damaged muscle cells. Increasing turnover of damaged muscle cells means that damaged muscle cells are more quickly broken down and/or removed as compared to a situation wherein turnover of damaged muscle cells is not increased. Turnover of damaged muscle cells is preferably assessed in a muscle biopsy, more preferably as described in 57 using a cross-section of a biopsy. A detectable increase of turnover may be an increase of 5%, 10%, 20%, 30%, 40%, 50%, 60%, 70%, 80%, 90% or more of the area wherein turnover has been identified using a biopsy cross-section. The increase is measured by comparison to the turnover as assessed in a same individual before treatment.

Without wishing to be bound to theory, it is believed that increasing turnover of muscle cells is preferred because this reduces inflammatory responses.

According to the present invention, a combination of a therapy for providing an individual with a functional dystrophin protein, together with an adjunct therapy for reducing inflammation, preferably for reducing muscle tissue inflammation in an individual, is particularly suitable for use as a medicament. Such combination is even better capable of alleviating one or more symptom(s) of Duchenne Muscular Dystrophy or Becker Muscular Dystrophy as compared to a sole therapy for providing an individual with a functional dystrophin protein. This embodiment also enhances the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

Further provided is therefore a combination of a compound for providing an individual with a functional dystrophin protein, and an adjunct compound for reducing inflammation, preferably for reducing muscle tissue inflammation in said individual, for use as a medicament. Since said combination is particularly suitable for counteracting DMD, the invention also provides a use of a compound for providing an individual with a functional dystrophin protein, and an adjunct compound for reducing inflammation, preferably for reducing muscle tissue inflammation in said individual, for the preparation of a medicament for alleviating one or more symptom(s) of Duchenne Muscular Dystrophy. In one embodiment, said combination is used in order to alleviate one or more symptom(s) of a severe form of BMD wherein a very short dystrophin protein is formed which is not sufficiently functional.

Preferred adjunct compound for reducing inflammation include a steroid, a TNF☐ inhibitor, a source of mIGF-1 and/or an antioxidant. However, any other compound able to reduce inflammation as defined herein is also encompassed within the present invention. Each of these compounds is later on extensively presented. Each of the compounds extensively presented may be used separately or in combination with each other and/or in combination with one or more of the adjunct compounds used for improving muscle fiber function, integrity and/or survival.

Furthermore, a combination of a therapy for providing an individual with a functional dystrophin protein, together with an adjunct therapy for improving muscle fiber function, integrity and/or survival in an individual is particularly suitable for use as a medicament. Such combination is even better capable of alleviating one or more symptom(s) of Duchenne Muscular Dystrophy as compared to a sole therapy for providing an individual with a functional dystrophin protein.

Further provided is therefore a combination of a compound for providing an individual with a functional dystrophin protein, and an adjunct compound for improving muscle fiber function, integrity and/or survival in said individual, for use as a medicament. This combination is also particularly suitable for counteracting DMD. A use of a compound for providing an individual with a functional dystrophin protein, and an adjunct compound for improving muscle fiber function, integrity and/or survival in said individual, for the preparation of a medicament for alleviating one or more symptom(s) of Duchenne Muscular Dystrophy is therefore also provided. In one embodiment, said combination is used in order to alleviate one or more symptom(s) of a severe form of BMD wherein a very short dystrophin protein is formed which is not sufficiently functional.

Preferred adjunct compounds for improving muscle fiber function, integrity and/or survival include a ion channel inhibitor, a protease inhibitor, L-arginine and/or an angiotensin II type I receptor blocker. However, any other compound able to improving muscle fiber function, integrity and/or survival as defined herein is also encompassed within the present invention. Each of these compounds is later on extensively presented. Each of the compounds extensively presented may be used separately or in combination with each other and/or in combination with one or more of the adjunct compounds used for reducing inflammation.

In one embodiment a pharmaceutical preparation is made which comprises at least one of the above mentioned combinations comprising a compound for providing an individual with a functional dystrophin protein together with an adjunct compound according to the invention. Further provided is therefore a pharmaceutical preparation comprising:

a compound for providing an individual with a functional dystrophin protein, and an adjunct compound for reducing inflammation, preferably for reducing muscle tissue inflammation in said individual, and/or an adjunct compound for improving muscle fiber function, integrity and/or survival in said individual, and a pharmaceutically acceptable carrier, adjuvant, diluent and/or excipient. Examples of suitable carriers and adjuvants are well known in the art and for instance comprise a saline solution. Dose ranges of compounds used in a pharmaceutical preparation according to the invention are designed on the basis of rising dose studies in clinical trials for which rigorous protocol requirements exist.

In a particularly preferred embodiment, a compound for providing an individual with a functional dystrophin protein is combined with a steroid. As shown in the Examples, such combination results in significant alleviation of DMD symptoms. One preferred embodiment of the present invention therefore provides a method for alleviating one or more symptom(s) of Duchenne Muscular Dystrophy in an individual, the method comprising administering to said individual a steroid and a compound for providing said individual with a functional dystrophin protein. A combination of a steroid and a compound for providing an individual with a functional dystrophin protein for use as a medicament is also provided, as well as a use of a steroid and a compound for providing an individual with a functional dystrophin protein for the preparation of a medicament for alleviating one or more symptom(s) of DMD. This embodiment also enhances the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

In one embodiment, said combination is used in order to alleviate one or more symptom(s) of a severe form of BMD wherein a very short dystrophin protein is formed which is not sufficiently functional.

A steroid is a terpenoid lipid characterized by a carbon skeleton with four fused rings, generally arranged in a 6-6-6-5 fashion. Steroids vary by the functional groups attached to these rings and the oxidation state of the rings. Steroids include hormones and drugs which are usually used to relieve swelling and inflammation, such as for instance prednisone, dexamethasone and vitamin D.

According to the present invention, supplemental effects of adjunct steroid therapy in DMD patients include reduction of tissue inflammation, suppression of cytotoxic cells, and improved calcium homeostasis. Most positive results are obtained in younger boys. Preferably the steroid is a corticosteroid (glucocorticosteroid). Preferably, prednisone steroids (such as prednisone, prednizolone or deflazacort) are used in a method according to the invention[21]. Dose ranges of (glucocortico)steroids to be used in the therapeutic applications as described herein are designed on the basis of rising dose studies in clinical trials for which rigorous protocol requirements exist. The usual doses are about 0.5-1.0 mg/kg/day, preferably about 0.75 mg/kg/day for prednisone and prednisolone, and about 0.4-1.4 mg/kg/day, preferably about 0.9 mg/kg/day for deflazacort.

In one embodiment, a steroid is administered to said individual prior to administering a compound for providing an individual with a functional dystrophin protein. In this embodiment, it is preferred that said steroid is administered at least one day, more preferred at least one week, more preferred at least two weeks, more preferred at least three weeks prior to administering a compound for providing said individual with a functional dystrophin protein.

In another preferred embodiment, a compound for providing an individual with a functional dystrophin protein is combined with a tumour necrosis factor-alpha (TNFα) inhibitor. Tumour necrosis factor-alpha (TNFα) is a pro-inflammatory cytokine that stimulates the inflammatory response. Pharmacological blockade of TNFα activity with the neutralising antibody infliximab (Remicade) is highly effective clinically at reducing symptoms of inflammatory diseases. In mdx mice, both infliximab and etanercept delay and reduce the necrosis of dystrophic muscle[24,25], with additional physiological benefits on muscle strength, chloride channel function and reduced CK levels being demonstrated in chronically treated exercised adult mdx mice[26]. Such highly specific anti-inflammatory drugs designed for use in other clinical conditions, are attractive alternatives to the use of steroids for DMD. In one embodiment, the use of a TNFα inhibitor is limited to periods of intensive muscle growth in boys when muscle damage and deterioration are especially pronounced.

One aspect of the present invention thus provides a method for alleviating one or more symptom(s) of Duchenne Muscular Dystrophy in an individual, the method comprising administering to said individual a TNFα inhibitor and a compound for providing said individual with a functional dystrophin protein. A combination of a TNFα inhibitor and a compound for providing an individual with a functional dystrophin protein for use as a medicament is also provided, as well as a use of a TNFα inhibitor and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. A preferred TNFα inhibitor is a dimeric fusion protein consisting of the extracellular ligand-binding domain of the human p75 receptor of TNFα linked to the Fc portion of human IgG1. A more preferred TNFα inhibitor is ethanercept (Amgen, America)[26]. The usual doses of ethanercept is about 0.2 mg/kg, preferably about 0.5 mg/kg twice a week. The administration is preferably subcutaneous.

In another preferred embodiment, a compound for providing an individual with a functional dystrophin protein is combined with a source of mIGF-1. As defined herein, a source of IGF-1 preferably encompasses mIGF-1 itself, a compound able of enhancing mIGF-1 expression and/or activity. Enhancing is herein synonymous with increasing. Expression of mIGF-1 is synonymous with amount of mIGF-1. mIGF-1 promotes regeneration of muscles through increase in satellite cell activity, and reduces inflammation and fibrosis[27]. Local injury of muscle results in increased mIGF-1 expression. In transgenic mice with extra IGF-1 genes, muscle hypertrophy and enlarged muscle fibers are observed[27]. Similarly, transgenic mdx mice show reduced muscle fiber degeneration[28]. Upregulation of the mIGF-1 gene and/or administration of extra amounts of mIGF-1 protein or a functional equivalent thereof (especially the mIGF-1 Ea isoform [as described in 27, human homolog IGF-1 isoform 4: SEQ ID NO: 2]) thus promotes the effect of other, preferably genetic, therapies for DMD, including antisense-induced exon skipping. The additional mIGF-1 levels in the above mentioned transgenic mice do not induce cardiac problems nor promote cancer, and have no pathological side effects. One aspect of the present invention thus provides a method for alleviating one or more symptom(s) of Duchenne Muscular Dystrophy in an individual, the method comprising administering to said individual a compound for providing said individual with a functional dystrophin protein, and providing said individual with a source of mIGF-1, preferably mIGF-1 itself, a compound able of increasing mIGF-1 expression and/or activity. As stated before, the amount of mIGF-1 is for instance increased by enhancing expression of the mIGF-1 gene and/ or by administration of mIGF-1 protein and/or a functional equivalent thereof (especially the mIGF-1 Ea isoform [as described in 27, human homolog IGF-1 isoform 4: SEQ ID NO: 2]). A combination of mIGF-1, or a compound capable of enhancing mIGF-1 expression or an mIGF-1 activity, and a compound for providing an individual with a functional dystrophin protein for use as a medicament is also provided, as well as a use of mIGF-1, or a compound capable of enhancing mIGF-1 expression or mIGF-1 activity, and a compound for providing an individual with a functional dystrophin protein for the preparation of a medicament for alleviating one or more symptom(s) of DMD. In one embodiment, such combination is used in order to alleviate one or more symptom(s) of a severe form of BMD wherein a very short dystrophin protein is formed which is not sufficiently functional.

Within the context of the invention, an increased amount or activity of mIGF-1 may be reached by increasing the gene expression level of an IGF-1 gene, by increasing the amount of a corresponding IGF-1 protein and/or by increasing an activity of an IGF1-protein. A preferred mIGF-1 protein has been earlier defined herein. An increase of an activity of said protein is herein understood to mean any detectable change in a biological activity exerted by said protein or in the steady state level of said protein as compared to said activity or steady-state in a individual who has not been treated. Increased amount or activity of mIGF-1 is preferably assessed by detection of increased expression of muscle hypertrophy biomarker GATA-2 (as described in 27).

Gene expression level is preferably assessed using classical molecular biology techniques such as (real time) PCR, arrays or Northern analysis. A steady state level of a protein is determined directly by quantifying the amount of a protein. Quantifying a protein amount may be carried out by any known technique such as Western blotting or immunoassay using an antibody raised against a protein. The skilled person will understand that alternatively or in combination with the quantification of a gene expression level and/or a corresponding protein, the quantification of a substrate of a corresponding protein or of any compound known to be associated with a function or activity of a corresponding protein or the quantification of said function or activity of a corresponding protein using a specific assay may be used to assess the alteration of an activity or steady state level of a protein.

In a method of the invention, an activity or steady-state level of a said protein may be altered at the level of the protein itself, e.g. by providing a protein to a cell from an exogenous source.

Preferably, an increase or an upregulation of the expression level of a said gene means an increase of at least 5% of the expression level of said gene using arrays. More preferably, an increase of the expression level of said gene means an increase of at least 10%, even more preferably at least 20%, at least 30%, at least 40%, at least 50%, at least 70%, at least 90%, at least 150% or more. In another preferred embodiment, an increase of the expression level of said protein means an increase of at least 5% of the expression level of said protein using western blotting and/or using ELISA or a suitable assay. More preferably, an increase of the expression level of a protein means an increase of at least 10%, even more preferably at least 20%, at least 30%, at least 40%, at least 50%, at least 70%, at least 90%, at least 150% or more.

In another preferred embodiment, an increase of a polypeptide activity means an increase of at least 5% of a polypeptide activity using a suitable assay. More preferably, an increase of a polypeptide activity means an increase of at least 10%, even more preferably at least 20%, at least 30%, at least 40%, at least 50%, at least 70%, at least 90%, at least 150% or more. The increase is preferably assessed by comparison to corresponding activity in the individual before treatment.

A preferred way of providing a source of mIGF1 is to introduce a transgene encoding mIGF1, preferably an mIGF-1 Ea isoform (as described in 27, human homolog IGF-1 isoform 4: SEQ ID NO: 2), more preferably in an AAV vector as later defined herein. Such source of mIGF1 is specifically expressed in muscle tissue as described in mice in 27.

In another preferred embodiment, a compound for providing an individual with a functional dystrophin protein is combined with an antioxidant. Oxidative stress is an important factor in the progression of DMD and promotes chronic inflammation and fibrosis[29]. The most prevalent products of oxidative stress, the peroxidized lipids, are increased by an average of 35% in Duchenne boys. Increased levels of the enzymes superoxide dismutase and catalase reduce the excessive amount of free radicals causing these effects. In fact, a dietary supplement Protandim® (LifeVantage) was clinically tested and found to increase levels of superoxide dismutase (up to 30%) and catalase (up to 54%), which indeed significantly inhibited the peroxidation of lipids in 29 healthy persons[30]. Such effective management of oxidative stress thus preserves muscle quality and so promotes the positive effect of DMD therapy. Idebenone is another potent antioxidant with a chemical structure derived from natural coenzyme Q10. It protects mitochondria where adenosine triphosphate, ATP, is generated by oxidative phosphorylation. The absence of dystrophin in DMD negatively affects this process in the heart, and probably also in skeletal muscle. Idebenone was recently applied in clinical trials in the US and Europe demonstrating efficacy on neurological aspects of Friedreich's Ataxia[31]. A phase-IIa double-blind, placebo-controlled randomized clinical trial with Idebenone has recently been started in Belgium, including 21 Duchenne boys at 8 to 16 years of age. The primary objective of this study is to determine the effect of Idebenone on heart muscle function. In addition several different tests will be performed to detect the possible functional benefit on muscle strength in the patients. When effective, Idebenone is a preferred adjunct compound for use in a method according to the present invention in order to enhance the therapeutic effect of DMD therapy, especially in the heart. One aspect of the present invention thus provides a method for alleviating one or more symptom(s) of Duchenne Muscular Dystrophy in an individual, the method comprising administering to said individual an antioxidant and a compound for providing said individual with a functional dystrophin protein. A combination of an antioxidant and a compound for providing an individual with a functional dystrophin protein for use as a medicament is also provided, as well as a use of an antioxidant and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the antioxidant, the skilled person will know which quantities are preferably used. An antioxidant may include bacoside, silymarin, curcumin, a polyphenol, preferably epigallocatechin-3-gallate (EGCG). Preferably, an antioxidant is a mixture of antioxidants as the dietary supplement Protandim® (LifeVantage). A daily capsule of 675 mg of Protandim® comprises 150 mg of B. monniera (45% bacosides), 225 mg of S. marianum (70-80% silymarin), 150 mg of W. somnifera powder, 75 mg green tea (98% polyphenols wherein 45% EGCG) and 75 mg turmeric (95% curcumin).

In another preferred embodiment, a compound for providing an individual with a functional dystrophin protein is combined with an ion channel inhibitor. The presence of damaged muscle membranes in DMD disturbs the passage of calcium ions into the myofibers, and the consequently disrupted calcium homeostasis activates many enzymes, e.g. proteases, that cause additional damage and muscle necrosis. Ion channels that directly contribute to the pathological accumulation of calcium in dystrophic muscle are potential targets for adjunct compounds to treat DMD. There is evidence that some drugs, such as pentoxifylline, block exercise-sensitive calcium channels[32] and antibiotics that block stretch activated channels reduce myofibre necrosis in mdx mice and CK levels in DMD boys[33]. One embodiment thus provides a method for alleviating one or more symptom(s) of Duchenne Muscular Dystrophy in an individual, the method comprising administering to said individual an ion channel inhibitor and a compound for providing said individual with a functional dystrophin protein. A combination of an ion channel inhibitor and a compound for providing an individual with a functional dystrophin protein for use as a medicament is also provided, as well as a use of an ion channel inhibitor and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional.

Preferably, ion channel inhibitors of the class of xanthines are used. More preferably, said xanthines are derivatives of methylxanthines, and most preferably, said methylxanthine derivates are chosen from the group consisting of pentoxifylline, furafylline, lisofylline, propentofylline, pentifylline, theophylline, torbafylline, albifylline, enprofylline and derivatives thereof. Most preferred is the use of pentoxifylline. Ion channel inhibitors of the class of xanthines enhance the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

Depending on the identity of the ion channel inhibitor, the skilled person will know which quantities are preferably used. Suitable dosages of pentoxifylline are between about 1 mg/kg/day to about 100 mg/kg/day, preferred dosages are between about 10 mg/kg/day to 50 mg/kg/day. Typical dosages used in humans are 20 mg/kg/day.

In one embodiment, an ion channel inhibitor is administered to said individual prior to administering a compound for providing an individual with a functional dystrophin protein. In this embodiment, it is preferred that said ion channel inhibitor is administered at least one day, more preferred at least one week, more preferred at least two weeks, more preferred at least three weeks prior to administering a compound for providing said individual with a functional dystrophin protein.

In another preferred embodiment, a compound for providing an individual with a functional dystrophin protein is combined with a protease inhibitor. Calpains are calcium activated proteases that are increased in dystrophic muscle and account for myofiber degeneration. Calpain inhibitors such as calpastatin, leupeptin[34], calpeptin, calpain inhibitor III, or PD150606 are therefore applied to reduce the degeneration process. A new compound, BN 82270 (Ipsen) that has dual action as both a calpain inhibitor and an antioxidant increased muscle strength, decreased serum CK and reduced fibrosis of the mdx diaphragm, indicating a therapeutic effect with this new compound[35]. Another compound of Leupeptin/Carnitine (Myodur) has recently been proposed for clinical trials in DMD patients.

MG132 is another proteasomal inhibitor that has shown to reduce muscle membrane damage, and to ameliorate the histopathological signs of muscular dystrophy[36]. MG-132 (CBZ-leucyl-leucyl-leucinal) is a cell-permeable, proteasomal inhibitor (Ki=4 nM) which inhibits NFkappaB activation by preventing IkappaB degradation (IC50=3 $\square$M). In addition, it is a peptide aldehyde that inhibits ubiquitin-mediated proteolysis by binding to and inactivating 20S and 26S proteasomes. MG-132 has shown to inhibit the proteasomal degradation of dystrophin-associated proteins in the dystrophic mdx mouse model[36]. This compound is thus also suitable for use as an adjunct pharmacological compound for DMD. Further provided is therefore a method for alleviating one or more symptom(s) of Duchenne Muscular Dystrophy in an individual, the method comprising administering to said individual a protease inhibitor and a compound for providing said individual with a functional dystrophin protein. A combination of a protease inhibitor and a compound for providing an individual with a functional dystrophin protein for use as a medicament is also provided, as well as a use of a protease inhibitor and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the protease inhibitor, the skilled person will know which quantities are preferably used.

In another preferred embodiment, a compound for providing an individual with a functional dystrophin protein is combined with L-arginine. Dystrophin-deficiency is associated with the loss of the DGC-complex at the fiber membranes, including neuronal nitric oxide synthase (nNOS). Expression of a nNOS transgene in mdx mice greatly reduced muscle membrane damage. Similarly, administration of L-arginine (the substrate for nitric oxide synthase) increased NO production and upregulated utrophin expression in mdx mice. Six weeks of L-arginine treatment improved muscle pathology and decreased serum CK in mdx mice[37]. The use of L-arginine as an adjunct therapy in combination with a compound for providing said individual with a functional dystrophin protein has not been disclosed.

Further provided is therefore a method for alleviating one or more symptom(s) of Duchenne Muscular Dystrophy in an individual, the method comprising administering to said individual L-arginine and a compound for providing said individual with a functional dystrophin protein. A combination of L-arginine and a compound for providing an individual with a functional dystrophin protein for use as a medicament is also provided, as well as a use of L-arginine and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional.

In another preferred embodiment, a compound for providing an individual with a functional dystrophin protein is combined with angiotensin II type 1 receptor blocker Losartan which normalizes muscle architecture, repair and function, as shown in the dystrophin-deficient mdx mouse model[23]. One aspect of the present invention thus provides a method for alleviating one or more symptom(s) of Duchenne Muscular Dystrophy in an individual, the method comprising administering to said individual angiotensin II type 1 receptor blocker Losartan, and a compound for providing said individual with a functional dystrophin protein. A combination of angiotensin II type 1 receptor blocker Losartan and a compound for providing an individual with a functional dystrophin protein for use as a medicament is also provided, as well as a use of angiotensin II type 1 receptor blocker Losartan and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the angiotensin II type 1 receptor blocker, the skilled person will know which quantities are preferably used.

In another preferred embodiment, a compound for providing an individual with a functional dystrophin protein is combined with an angiotensin-converting enzyme (ACE) inhibitor, preferably perindopril. ACE inhibitors are capable of lowering blood pressure. Early initiation of treatment with perindopril is associated with a lower mortality in DMD patients[22]. One aspect of the present invention thus provides a method for alleviating one or more symptom(s) of Duchenne Muscular Dystrophy in an individual, the method comprising administering to said individual an ACE inhibitor, preferably perindopril, and a compound for providing said individual with a functional dystrophin protein. A combination of an ACE inhibitor, preferably perindopril, and a compound for providing an individual with a functional dystrophin protein for use as a medicament is also provided, as well as a use of an ACE inhibitor, preferably perindopril, and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. The usual doses of an ACE inhibitor, preferably perindopril are about 2 to 4 mg/day[22].

In a more preferred embodiment, an ACE inhibitor is combined with at least one of the previously identified adjunct compounds.

In another preferred embodiment, a compound for providing an individual with a functional dystrophin protein is combined with a compound which is capable of enhancing exon skipping and/or inhibiting spliceosome assembly and/or splicing. Small chemical compounds, such as for instance specific indole derivatives, have been shown to selectively inhibit spliceosome assembly and splicing[38], for instance by interfering with the binding of serine- and arginine-rich (SR) proteins to their cognate splicing enhancers (ISEs or ESEs) and/or by interfering with the binding of splicing repressors to silencer sequences (ESSs or ISSs). These compounds are therefore suitable for applying as adjunct compounds that enhance exon skipping.

Further provided is therefore a method for alleviating one or more symptom(s) of Duchenne Muscular Dystrophy in an individual, the method comprising administering to said individual a compound for enhancing exon skipping and/or inhibiting spliceosome assembly and/or splicing, and a compound for providing said individual with a functional dystrophin protein. A combination of a compound for enhancing exon skipping and/or inhibiting spliceosome assembly and/or splicing and a compound for providing an individual with a functional dystrophin protein for use as a medicament is also provided, as well as a use of a compound for enhancing exon skipping and/or inhibiting spliceosome assembly and/or splicing and a compound for providing an individual with a functional dystrophin protein for the preparation of a medicament for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the compound which is capable of enhancing exon skipping and/or inhibiting spliceosome assembly and/or splicing, the skilled person will know which quantities are preferably used. In a more preferred embodiment, a compound for enhancing exon skipping and/or inhibiting spliceosome assembly and/or splicing is combined with a ACE inhibitor and/or with any adjunct compounds as identified earlier herein.

A pharmaceutical preparation comprising a compound for providing an individual with a functional dystrophin protein, any of the above mentioned adjunct compounds, and a pharmaceutically acceptable carrier, filler, preservative, adjuvant, solubilizer, diluent and/or excipient is also provided. Such pharmaceutically acceptable carrier, filler, preservative, adjuvant, solubilizer, diluent and/or excipient may for instance be found in Remington: The Science and Practice of Pharmacy, 20th Edition. Baltimore, Md.: Lippincott Williams & Wilkins, 2000.

The invention thus provides a method, combination, use or pharmaceutical preparation according to the invention, wherein said adjunct compound comprises a steroid, an ACE inhibitor (preferably perindopril), angiotensin II type 1 receptor blocker Losartan, a tumour necrosis factor-alpha (TNFα) inhibitor, a source of mIGF-1, preferably mIGF-1, a compound for enhancing mIGF-1 expression, a compound for enhancing mIGF-1 activity, an antioxidant, an ion channel inhibitor, a protease inhibitor, L-arginine and/or a compound for enhancing exon skipping and/or inhibiting spliceosome assembly and/or splicing.

As described herein before, an individual is provided with a functional dystrophin protein in various ways, for instance by stop codon suppression by gentamycin or PTC124[16,17], or by adeno-associated virus (AAV)-mediated gene delivery of a functional mini- or micro-dystrophin gene[18-20].

Preferably, however, said compound for providing said individual with a functional dystrophin protein comprises an oligonucleotide, or a functional equivalent thereof, for at least in part decreasing the production of an aberrant dystrophin protein in said individual. Decreasing the production of an aberrant dystrophin mRNA, or aberrant dystrophin protein, preferably means that 90%, 80%, 70%, 60%, 50%, 40%, 30%, 20%, 10%, 5% or less of the initial amount of aberrant dystrophin mRNA, or aberrant dystrophin protein, is still detectable by RT PCR (mRNA) or immunofluorescence or western blot analysis (protein). An aberrant dystrophin mRNA or protein is also referred to herein as a non-functional dystrophin mRNA or protein. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein. Said oligonucleotide preferably comprises an antisense oligoribonucleotide. In a preferred embodiment an exon skipping technique is applied. Exon skipping interferes with the natural splicing processes occurring within a eukaryotic cell. In higher eukaryotes the genetic information for proteins in the DNA of the cell is encoded in exons which are separated from each other by intronic sequences. These introns are in some cases very long. The transcription machinery of eukaryotes generates a pre-mRNA which contains both exons and introns, while the splicing machinery, often already during the production of the pre-mRNA, generates the actual coding region for the protein by splicing together the exons present in the pre-mRNA.

Exon-skipping results in mature mRNA that lacks at least one skipped exon. Thus, when said exon codes for amino acids, exon skipping leads to the expression of an altered product. Technology for exon-skipping is currently directed towards the use of antisense oligonucleotides (AONs). Much of this work is done in the mdx mouse model for Duchenne muscular dystrophy. The mdx mouse, which carries a nonsense mutation in exon 23 of the dystrophin gene, has been used as an animal model of DMD. Despite the mdx mutation, which should preclude the synthesis of a functional dystrophin protein, rare, naturally occurring dystrophin positive fibers have been observed in mdx muscle tissue. These dystrophin-positive fibers are thought to have arisen from an apparently naturally occurring exon-skipping mechanism, either due to somatic mutations or through alternative splicing. AONs directed to, respectively, the 3' and/or 5' splice sites of introns 22 and 23 in dystrophin pre-mRNA, have been shown to interfere with factors normally involved in removal of intron 23 so that also exon 23 was removed from the mRNA[3,5,6,39,40].

By the targeted skipping of a specific exon, a DMD phenotype is converted into a milder BMD phenotype. The skipping of an exon is preferably induced by the binding of AONs targeting either one or both of the splice sites, or exon-internal sequences. An oligonucleotide directed toward an exon internal sequence typically exhibits no overlap with non-exon sequences. It preferably does not overlap with the splice sites at least not insofar as these are present in the intron. An oligonucleotide directed toward an exon internal sequence preferably does not contain a sequence complementary to an adjacent intron. Further provided is thus a method, combination, use or pharmaceutical preparation according to the invention, wherein said compound for providing said individual with a functional dystrophin protein comprises an oligonucleotide, or a functional equivalent thereof, for inhibiting inclusion of an exon of a dystrophin pre-mRNA into mRNA produced from splicing of said pre-mRNA. An exon skipping technique is preferably applied such that the absence of an exon from mRNA produced from dystrophin pre-mRNA generates a coding region for a functional—albeit shorter—dystrophin protein. In this context, inhibiting inclusion of an exon preferably means that the detection of the original, aberrant dystrophin mRNA is decreased of at least about 10% as assessed by RT-PCR or that a corresponding aberrant dystrophin protein is decreased of at least about 10% as assessed by immunofluorescence or western blot analysis. The decrease is preferably of at least 20%, 30%, 40%, 50%, 60%, 70%, 80%, 90% or 100%.

Once a DMD patient is provided with a functional dystrophin protein, the cause of DMD is taken away. Hence, it would then be expected that the symptoms of DMD are sufficiently alleviated. However, as already described before, the present invention provides the insight that, even though exon skipping techniques are capable of providing a functional dystrophin protein, a symptom of DMD is still further alleviated by administering to a DMD patient an adjunct compound for reducing inflammation, preferably for reducing muscle tissue inflammation, and/or an adjunct compound for improving muscle fiber function, integrity and/or survival. Moreover, the present invention provides the insight that an adjunct therapy counteracting inflammation does not negatively influence AON therapy. The present invention further provides the insight that the skipping frequency of a dystrophin exon from a pre-mRNA comprising said exon is enhanced, when using an oligonucleotide directed toward the exon or to one or both splice sites of said exon. The enhanced skipping frequency also increases the level of functional dystrophin protein produced in a muscle cell of a DMD or BMD individual.

Since an exon of a dystrophin pre-mRNA will only be included into the resulting mRNA when both the splice sites are recognised by the spliceosome complex, splice sites are obvious targets for AONs. One embodiment therefore provides a method, combination, use or pharmaceutical preparation according to the invention, wherein said compound for providing said individual with a functional dystrophin protein comprises an oligonucleotide, or a functional equivalent thereof, comprising a sequence which is complementary to a non-exon region of a dystrophin pre mRNA. In one embodiment an AON is used which is solely complementary to a non-exon region of a dystrophin pre mRNA. This is however not necessary: it is also possible to use an AON which comprises an intron-specific sequence as well as exon-specific sequence. Such AON comprises a sequence which is complementary to a non-exon region of a dystrophin pre mRNA, as well as a sequence which is complementary to an exon region of a dystrophin pre mRNA. Of course, an AON is not necessarily complementary to the entire sequence of a dystrophin exon or intron. AONs which are complementary to a part of such exon or intron are preferred. An AON is preferably complementary to at least part of a dystrohin exon and/or intron, said part having at least 13 nucleotides.

Splicing of a dystrophin pre-mRNA occurs via two sequential transesterification reactions. First, the 2'OH of a specific branch-point nucleotide within the intron that is defined during spliceosome assembly performs a nucleophilic attack on the first nucleotide of the intron at the 5' splice site forming the lariat intermediate. Second, the 3'OH of the released 5' exon then performs a nucleophilic attack at the last nucleotide of the intron at the 3' splice site thus joining the exons and releasing the intron lariat. The branch point and splice sites of an intron are thus involved in a splicing event. Hence, an oligonucleotide comprising a sequence which is complementary to such branch point and/or splice site is preferably used for exon skipping. Further provided is therefore a method, combination, use or pharmaceutical preparation according to the invention, wherein said compound for providing said individual with a functional dystrophin protein comprises an oligonucleotide, or a functional equivalent thereof, comprising a sequence which is complementary to a splice site and/or branch point of a dystrophin pre mRNA.

Since splice sites contain consensus sequences, the use of an oligonucleotide or a functional equivalent thereof (herein also called an AON) comprising a sequence which is complementary of a splice site involves the risk of promiscuous hybridization. Hybridization of AONs to other splice sites than the sites of the exon to be skipped could easily interfere with the accuracy of the splicing process. To overcome these and other potential problems related to the use of AONs which are complementary to an intron sequence, one preferred embodiment provides a method, combination, use or pharmaceutical preparation according to the invention, wherein said compound for providing said individual with a functional dystrophin protein comprises an oligonucleotide, or a functional equivalent thereof, comprising a sequence which is complementary to a dystrophin pre-mRNA exon. Preferably, said AON is capable of specifically inhibiting an exon inclusion signal of at least one exon in said dystrophin pre-mRNA. Interfering with an exon inclusion signal (EIS) has the advantage that such elements are located within the exon. By providing an AON for the interior of the exon to be skipped, it is possible to interfere with the exon inclusion signal thereby effectively masking the exon from the splicing apparatus. The failure of the splicing apparatus to recognize the exon to be skipped thus leads to exclusion of the exon from the final mRNA. This embodiment does not interfere directly with the enzymatic process of the splicing machinery (the joining of the exons). It is thought that this allows the method to be more specific and/or reliable. It is thought that an EIS is a particular structure of an exon that allows splice acceptor and donor to assume a particular spatial conformation. In this concept it is the particular spatial conformation that enables the splicing machinery to recognize the exon. However, the invention is certainly not limited to this model. It has been found that agents capable of binding to an exon are capable of inhibiting an EIS. An AON may specifically contact said exon at any point and still be able to specifically inhibit said EIS.

Using exon-internal AONs specific for an exon 46 sequence, we were previously able to modulate the splicing pattern in cultured myotubes from two different DMD patients with an exon 45 deletion[11]. Following AON treatment, exon 46 was skipped, which resulted in a restored reading frame and the induction of dystrophin synthesis in at least 75% of the cells. We have recently shown that exon skipping can also efficiently be induced in human control and series of patients with different mutations, including deletions, duplications and point mutations, for 39 different DMD exons using exon-internal AONs[1,2,11-15].

Within the context of the invention, a functional equivalent of an oligonucleotide preferably means an oligonucleotide as defined herein wherein one or more nucleotides have been substituted and wherein an activity of said functional equivalent is retained to at least some extent. Preferably, an activity of said functional equivalent is providing a functional dystrophin protein. Said activity of said functional equivalent is therefore preferably assessed by quantifying the amount of a functional dystrophin protein. A functional dystrophin is herein preferably defined as being a dystrophin able to bind actin and members of the DGC protein complex. The assessment of said activity of an oligonucleotide is preferably done by RT-PCR or by immunofluorescence or Western blot analyses. Said activity is preferably retained to at least some extent when it represents at least 50%, or at least 60%, or at least 70% or at least 80% or at least 90% or at least 95% or more of corresponding activity of said oligonucleotide the functional equivalent derives from. Throughout this application, when the word oligonucleotide is used it may be replaced by a functional equivalent thereof as defined herein.

Hence, the use of an oligonucleotide, or a functional equivalent thereof, comprising or consisting of a sequence which is complementary to a dystrophin pre-mRNA exon provides good anti-DMD results. In one preferred embodiment an oligonucleotide, or a functional equivalent thereof, is used which comprises or consists of a sequence which is complementary to at least part of dystrophin pre-mRNA exon 2, 8, 9, 17, 19, 29, 40-46, 48-53, 55 or 59, said part having at least 13 nucleotides. However, said part may also have at least 14, 15, 16, 17, 18, 19, 20, 21, 22, 23, 24, 25, 26, 27, 28, 29, 30 nucleotides.

Most preferably an AON is used which comprises or consists of a sequence which is complementary to at least part of dystrophin pre-mRNA exon 51, 44, 45, 53, 46, 43, 2, 8, 50 and/or 52, said part having at least 13 nucleotides. However, said part may also have at least 14, 15, 16, 17, 18, 19, 20, 21, 22, 23, 24, 25, 26, 27, 28, 29, 30 nucleotides. Most preferred oligonucleotides are identified by each of the following sequences SEQ ID NO: 3 to SEQ ID NO: 284. Accordingly, a most preferred oligonucleotide as used herein is represented by a sequence from SEQ ID NO:3 to SEQ ID NO:284. A most preferred oligonucleotide as used herein is selected from the group consisting of SEQ ID NO:3 to NO:284.

Said exons are listed in decreasing order of patient population applicability. Hence, the use of an AON comprising a sequence which is complementary to at least part of dystrophin pre-mRNA exon 51 is suitable for use in a larger part of the DMD patient population as compared to an AON comprising a sequence which is complementary to dystrophin pre-mRNA exon 44, et cetera.

In a preferred embodiment, an oligonucleotide of the invention which comprises a sequence that is complementary to part of dystrophin pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% or more. In a most preferred embodiment, the oligonucleotide of the invention consists of a sequence that is complementary to part of dystrophin pre-mRNA as defined herein. For example, an oligonucleotide may comprise a sequence that is complementary to part of dystrophin pre-mRNA as defined herein and additional flanking sequences. In a more preferred embodiment, the length of said complementary part of said oligonucleotide is of at least 13, 14, 15, 16, 17, 18, 19, 20, 21, 22, 23, 24, 25, 26, 27, 28, 29, 30 nucleotides. Preferably, additional flanking sequences are used to modify the binding of a protein to the oligonucleotide, or to modify a thermodynamic property of the oligonucleotide, more preferably to modify target RNA binding affinity.

One preferred embodiment provides a method, combination, use or pharmaceutical preparation according to the invention, wherein said compound for providing said individual with a functional dystrophin protein comprises an oligonucleotide, or a functional equivalent thereof, which comprises:

a sequence which is complementary to a region of a dystrophin pre-mRNA exon that is hybridized to another part of a dystrophin pre-mRNA exon (closed structure), and a sequence which is complementary to a region of a dystrophin pre-mRNA exon that is not hybridized in said dystrophin pre-mRNA (open structure).

For this embodiment, reference is made to our WO 2004/083432 patent application. RNA molecules exhibit strong secondary structures, mostly due to base pairing of complementary or partly complementary stretches within the same RNA. It has long since been thought that structures in the RNA play a role in the function of the RNA. Without being bound by theory, it is believed that the secondary structure of the RNA of an exon plays a role in structuring the splicing process. Through its structure, an exon is recognized as a part that needs to be included in the mRNA. Herein this signalling function is referred to as an exon inclusion signal. A complementary oligonucleotide of this embodiment is capable of interfering with the structure of the exon and thereby capable of interfering with the exon inclusion signal of the exon. It has been found that many complementary oligonucleotides indeed comprise this capacity, some more efficient than others. Oligonucleotides of this preferred embodiment, i.e. those with the said overlap directed towards open and closed structures in the native exon RNA, are a selection from all possible oligonucleotides. The selection encompasses oligonucleotides that can efficiently interfere with an exon inclusion signal. Without being bound by theory it is thought that the overlap with an open structure improves the invasion efficiency of the oligonucleotide (i.e. increases the efficiency with which the oligonucleotide can enter the structure), whereas the overlap with the closed structure subsequently increases the efficiency of interfering with the secondary structure of the RNA of the exon, and thereby interfere with the exon inclusion signal. It is found that the length of the partial complementarity to both the closed and the open structure is not extremely restricted. We have observed high efficiencies with oligonucleotides with variable lengths of complementarity in either structure. The term complementarity is used herein to refer to a stretch of nucleic acids that can hybridise to another stretch of nucleic acids under physiological conditions. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may to some extent be allowed, if under the circumstances in the cell, the stretch of nucleotides is capable of hybridising to the complementary part. In a preferred embodiment a complementary part (either to said open or to said closed structure) comprises at least 3, and more preferably at least 4 consecutive nucleotides. The complementary regions are preferably designed such that, when combined, they are specific for the exon in the pre-mRNA. Such specificity may be created with various lengths of complementary regions as this depends on the actual sequences in other (pre-)mRNA in the system. The risk that also one or more other pre-mRNA will be able to hybridise to the oligonucleotide decreases with increasing size of the oligonucleotide. It is clear that oligonucleotides comprising mismatches in the region of complementarity but that retain the capacity to hybridise to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought that higher hybridisation strengths, (i.e. increasing number of interactions with the opposing strand) are favourable in increasing the efficiency of the process of interfering with the splicing machinery of the system. Preferably, the complementarity is between 90 and 100%. In general this allows for approximately 1 or 2 mismatch(es) in an oligonucleotide of around 20 nucleotides The secondary structure is best analysed in the context of the pre-mRNA wherein the exon resides. Such structure may be analysed in the actual RNA. However, it is currently possible to predict the secondary structure of an RNA molecule (at lowest energy costs) quite well using structure-modelling programs. A non-limiting example of a suitable program is RNA mfold version 3.1 server[41]. A person skilled in the art will be able to predict, with suitable reproducibility, a likely structure of the exon, given the nucleotide sequence. Best predictions are obtained when providing such modelling programs with both the exon and flanking intron sequences. It is typically not necessary to model the structure of the entire pre-mRNA.

The open and closed structure to which the oligonucleotide is directed, are preferably adjacent to one another. It is thought that in this way the annealing of the oligonucleotide to the open structure induces opening of the closed structure whereupon annealing progresses into this closed structure. Through this action the previously closed structure assumes a different conformation. The different conformation results in the disruption of the exon inclusion signal. However, when potential (cryptic) splice acceptor and/or donor sequences are present within the targeted exon, occasionally a new exon inclusion signal is generated defining a different (neo) exon, i.e. with a different 5' end, a different 3' end, or both. This type of activity is within the scope of the present invention as the targeted exon is excluded from the mRNA. The presence of a new exon, containing part of the targeted exon, in the mRNA does not alter the fact that the targeted exon, as such, is excluded. The inclusion of a neo-exon can be seen as a side effect which occurs only occasionally. There are two possibilities when exon skipping is used to restore (part of) an open reading frame of dystrophin that is disrupted as a result of a mutation. One is that the neo-exon is functional in the restoration of the reading frame, whereas in the other case the reading frame is not restored. When selecting oligonucleotides for restoring dystrophin reading frames by means of exon-skipping it is of course clear that under these conditions only those oligonucleotides are selected that indeed result in exon-skipping that restores the dystrophin open reading frame, with or without a neo-exon.

Further provided is a method, combination, use or pharmaceutical preparation according to the invention, wherein said compound for providing said individual with a functional dystrophin protein comprises an oligonucleotide, or a functional equivalent thereof, which comprises a sequence that is complementary to a binding site for a serine-arginine (SR) protein in RNA of an exon of a dystrophin pre-mRNA. In our WO 2006/112705 patent application we have disclosed the presence of a correlation between the effectivity of an exon-internal antisense oligonucleotide (AON) in inducing exon skipping and the presence of a (for example by ESEfinder) predicted SR binding site in the target pre-mRNA site of said AON. Therefore, in one embodiment an oligonucleotide is generated comprising determining a (putative) binding site for an SR (Ser-Arg) protein in RNA of a dystrophin exon and producing an oligonucleotide that is complementary to said RNA and that at least partly overlaps said (putative) binding site. The term "at least partly overlaps" is defined herein as to comprise an overlap of only a single nucleotide of an SR binding site as well as multiple nucleotides of said binding site as well as a complete overlap of said binding site. This embodiment preferably further comprises determining from a secondary structure of said RNA, a region that is hybridised to another part of said RNA (closed structure) and a region that is not hybridised in said structure (open structure), and subsequently generating an oligonucleotide that at least partly overlaps said (putative) binding site and that overlaps at least part of said closed structure and overlaps at least part of said open structure. In this way we increase the chance of obtaining an oligonucleotide that is capable of interfering with the exon inclusion from the pre-mRNA into mRNA. It is possible that a first selected SR-binding region does not have the requested open-closed structure in which case another (second) SR protein binding site is selected which is then subsequently tested for the presence of an open-closed structure. This process is continued until a sequence is identified which contains an SR protein binding site as well as a(n) (partly overlapping) open-closed structure. This sequence is then used to design an oligonucleotide which is complementary to said sequence.

Such a method for generating an oligonucleotide is also performed by reversing the described order, i.e. first generating an oligonucleotide comprising determining, from a secondary structure of RNA from a dystrophin exon, a region that assumes a structure that is hybridised to another part of said RNA (closed structure) and a region that is not hybridised in said structure (open structure), and subsequently generating an oligonucleotide, of which at least a part of said oligonucleotide is complementary to said closed structure and of which at least another part of said oligonucleotide is complementary to said open structure. This is then followed by determining whether an SR protein binding site at least overlaps with said open/closed structure. In this way the method of WO 2004/083432 is improved. In yet another embodiment the selections are performed simultaneously.

Without wishing to be bound by any theory it is currently thought that use of an oligonucleotide directed to an SR protein binding site results in (at least partly) impairing the binding of an SR protein to the binding site of an SR protein which results in disrupted or impaired splicing.

Preferably, an open/closed structure and an SR protein binding site partly overlap and even more preferred an open/closed structure completely overlaps an SR protein binding site or an SR protein binding site completely overlaps an open/closed structure. This allows for an improved disruption of exon inclusion.

Besides consensus splice sites sequences, many (if not all) exons contain splicing regulatory sequences such as exonic splicing enhancer (ESE) sequences to facilitate the recognition of genuine splice sites by the spliceosome[42,43]. A subgroup of splicing factors, called the SR proteins, can bind to these ESEs and recruit other splicing factors, such as U1 and U2AF to (weakly defined) splice sites. The binding sites of the four most abundant SR proteins (SF2/ASF, SC35, SRp40 and SRp55) have been analyzed in detail and these results are implemented in ESEfinder, a web source that predicts potential binding sites for these SR proteins[42,43]. There is a correlation between the effectiveness of an AON and the presence/absence of an SF2/ASF, SC35 and SRp40 binding site. In a preferred embodiment, the invention thus provides a method, combination, use or pharmaceutical preparation as described above, wherein said SR protein is SF2/ASF or SC35 or SRp40.

In one embodiment a DMD patient is provided with a functional dystrophin protein by using an oligonucleotide, or a functional equivalent thereof, which is capable of specifically binding a regulatory RNA sequence which is required for the correct splicing of a dystrophin exon in a transcript. Several cis-acting RNA sequences are required for the correct splicing of exons in a transcript. In particular, supplementary elements such as intronic or exonic splicing enhancers (ISEs and ESEs) or silencers (ISSs and ESEs) are identified to regulate specific and efficient splicing of constitutive and alternative exons. Using sequence-specific antisense oligonucleotides (AONs) that bind to the elements, their regulatory function is disturbed so that the exon is skipped, as shown for DMD. Hence, in one preferred embodiment an oligonucleotide or functional equivalent thereof is used which is complementary to an intronic splicing enhancer (ISE), an exonic splicing enhancer (ESE), an intronic splicing silencer (ISS) and/or an exonic splicing silencer (ESS). As already described herein before, a dystrophin exon is in one preferred embodiment skipped by an agent capable of specifically inhibiting an exon inclusion signal of said exon, so that said exon is not recognized by the splicing machinery as a part that needs to be included in the mRNA. As a result, a mRNA without said exon is formed.

An AON used in a method of the invention is preferably complementary to a consecutive part of between 13 and 50 nucleotides of dystrophin exon RNA or dystrophin intron RNA. In one embodiment an AON used in a method of the invention is complementary to a consecutive part of between 16 and 50 nucleotides of a dystrophin exon RNA or dystrophin intron RNA. Preferably, said AON is complementary to a consecutive part of between 15 and 25 nucleotides of said exon RNA. More preferably, an AON is used which comprises a sequence which is complementary to a consecutive part of between 20 and 25 nucleotides of a dystrophin exon RNA or a dystrophin intron RNA.

Different types of nucleic acid may be used to generate the oligonucleotide. Preferably, said oligonucleotide comprises RNA, as RNA/RNA hybrids are very stable. Since one of the aims of the exon skipping technique is to direct splicing in subjects it is preferred that the oligonucleotide RNA comprises a modification providing the RNA with an additional property, for instance resistance to endonucleases and RNaseH, additional hybridisation strength, increased stability (for instance in a bodily fluid), increased or decreased flexibility, reduced toxicity, increased intracellular transport, tissue-specificity, etc. Preferably said modification comprises a 2'-O-methyl-phosphorothioate oligoribonucleotide modification. Preferably said modification comprises a 2'-O-methyl-phosphorothioate oligodeoxyribonucleotide modification. One embodiment thus provides a method, combination, use or pharmaceutical preparation according to the invention, wherein an oligonucleotide is used which comprises RNA which contains a modification, preferably a 2'-O-methyl modified ribose (RNA) or deoxyribose (DNA) modification.

In one embodiment the invention provides a hybrid oligonucleotide comprising an oligonucleotide comprising a 2'-O-methyl-phosphorothioate oligo(deoxy)ribonucleotide modification and locked nucleic acid. This particular combination comprises better sequence specificity compared to an equivalent consisting of locked nucleic acid, and comprises improved effectivity when compared with an oligonucleotide consisting of 2'-O-methyl-phosphorothioate oligo(deoxy)ribonucleotide modification.

With the advent of nucleic acid mimicking technology it has become possible to generate molecules that have a similar, preferably the same hybridisation characteristics in kind not necessarily in amount as nucleic acid itself. Such functional equivalents are of course also suitable for use in a method of the invention. Preferred examples of functional equivalents of an oligonucleotide are peptide nucleic acid and/or locked nucleic acid. Most preferably, a morpholino phosphorodiamidate is used. Suitable but non-limiting examples of equivalents of oligonucleotides of the invention can be found in[44-50]. Hybrids between one or more of the equivalents among each other and/or together with nucleic acid are of course also suitable. In a preferred embodiment locked nucleic acid is used as a functional equivalent of an oligonucleotide, as locked nucleic acid displays a higher target affinity and reduced toxicity and therefore shows a higher efficiency of exon skipping.

In one embodiment an oligonucleotide, or a functional equivalent thereof, which is capable of inhibiting inclusion of a dystrophin exon into dystrophin mRNA is combined with at least one other oligonucleotide, or functional equivalent thereof, that is capable of inhibiting inclusion of another dystrophin exon into dystrophin mRNA. This way, inclusion of two or more exons of a dystrophin pre-mRNA in mRNA produced from this pre-mRNA is prevented. This embodiment is further referred to as double- or multi-exon skipping[2, 15]. In most cases double-exon skipping results in the exclusion of only the two targeted exons from the dystrophin pre-mRNA. However, in other cases it was found that the targeted exons and the entire region in between said exons in said pre-mRNA were not present in the produced mRNA even when other exons (intervening exons) were present in such region. This multi-skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other.

Further provided is therefore a method, combination, use or pharmaceutical preparation according to the invention, wherein a nucleotide sequence is used which comprises at least 8, preferably between 16 to 80, consecutive nucleotides that are complementary to a first exon of a dystrophin pre-mRNA and wherein a nucleotide sequence is used which comprises at least 8, preferably between 16 to 80, consecutive nucleotides that are complementary to a second exon of said dystrophin pre-mRNA.

In one preferred embodiment said first and said second exon are separated in said dystrophin pre-mRNA by at least one exon to which said oligonucleotide is not complementary.

It is possible to specifically promote the skipping of also the intervening exons by providing a linkage between the two complementary oligonucleotides. Hence, in one embodiment stretches of nucleotides complementary to at least two dystrophin exons are separated by a linking moiety. The at least two stretches of nucleotides are thus linked in this embodiment so as to form a single molecule. Further provided is therefore a method, combination, use or pharmaceutical preparation according to the invention wherein said oligonucleotide, or functional equivalent thereof, for providing said individual with a functional dystrophin protein is complementary to at least two exons in a dystrophin pre-mRNA, said oligonucleotide or functional equivalent comprising at least two parts wherein a first part comprises an oligonucleotide having at least 8, preferably between 16 to 80, consecutive nucleotides that are complementary to a first of said at least two exons and wherein a second part comprises an oligonucleotide having at least 8, preferably between 16 to 80, consecutive nucleotides that are complementary to a second exon in said dystrophin pre-mRNA. The linkage may be through any means but is preferably accomplished through a nucleotide linkage. In the latter case the number of nucleotides that do not contain an overlap between one or the other complementary exon can be zero, but is preferably between 4 to 40 nucleotides. The linking moiety can be any type of moiety capable of linking oligonucleotides. Preferably, said linking moiety comprises at least 4 uracil nucleotides. Currently, many different compounds are available that mimic hybridisation characteristics of oligonucleotides. Such a compound, called herein a functional equivalent of an oligonucleotide, is also suitable for the present invention if such equivalent comprises similar hybridisation characteristics in kind not necessarily in amount. Suitable functional equivalents are mentioned earlier in this description. As mentioned, oligonucleotides of the invention do not have to consist of only oligonucleotides that contribute to hybridisation to the targeted exon. There may be additional material and/or nucleotides added.

The DMD gene is a large gene, with many different exons. Considering that the gene is located on the X-chromosome, it is mostly boys that are affected, although girls can also be affected by the disease, as they may receive a bad copy of the gene from both parents, or are suffering from a particularly biased inactivation of the functional allele due to a particularly biased X chromosome inactivation in their muscle cells. The protein is encoded by a plurality of exons (79) over a range of at least 2.6 Mb. Defects may occur in any part of the DMD gene. Skipping of a particular exon or particular exons can, very often, result in a restructured mRNA that encodes a shorter than normal but at least partially functional dystrophin protein. A practical problem in the development of a medicament based on exon-skipping technology is the plurality of mutations that may result in a deficiency in functional dystrophin protein in the cell. Despite the fact that already multiple different mutations can be corrected for by the skipping of a single exon, this plurality of mutations, requires the generation of a large number of different pharmaceuticals as for different mutations different exons need to be skipped. An advantage of a compound capable of inducing skipping of two or more exons, is that more than one exon can be skipped with a single pharmaceutical. This property is not only practically very useful in that only a limited number of pharmaceuticals need to be generated for treating many different DMD or particular, severe BMD mutations. Another option now open to the person skilled in the art is to select particularly functional restructured dystrophin proteins and produce compounds capable of generating these preferred dystrophin proteins. Such preferred end results are further referred to as mild phenotype dystrophins.

Each compound, an oligonucleotide and/or an adjunct compound as defined herein for use according to the invention may be suitable for direct administration to a cell, tissue and/or an organ in vivo of individuals affected by or at risk of developing DMD or BMD, and may be administered directly in vivo, ex vivo or in vitro.

Alternatively, suitable means for providing cells with an oligonucleotide or equivalent thereof are present in the art. An oligonucleotide or functional equivalent thereof may for example be provided to a cell in the form of an expression vector wherein the expression vector encodes a transcript comprising said oligonucleotide. The expression vector is preferably introduced into the cell via a gene delivery vehicle. A preferred delivery vehicle is a viral vector such as an adeno-associated virus vector (AAV), or a retroviral vector such as a lentivirus vector[4,51,52] and the like. Also plasmids, artificial chromosomes, plasmids suitable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably in the form of a fusion transcript with an U1 or U7 transcript[4,51,52]. Such fusions may be generated as described[53,54]. The oligonucleotide may be delivered as is. However, the oligonucleotide may also be encoded by the viral vector. Typically this is in the form of an RNA transcript that comprises the sequence of the oligonucleotide in a part of the transcript.

Improvements in means for providing cells with an oligonucleotide or equivalent thereof, are anticipated considering the progress that has already thus far been achieved. Such future improvements may of course be incorporated to achieve the mentioned effect on restructuring of mRNA using a method of the invention. The oligonucleotide or equivalent thereof can be delivered as is to the cells. When administering the oligonucleotide or equivalent thereof to an individual, it is preferred that the oligonucleotide is dissolved in a solution that is compatible with the delivery method. For intravenous, subcutaneous, intramuscular, intrathecal and/or intraventricular administration it is preferred that the solution is a physiological salt solution. Particularly preferred for a method of the invention is the use of an excipient that will aid in delivery of a compound as defined herein, preferably an oligonucleotide and optionally together with an adjunct compound to a cell and into a cell, preferably a muscle cell. Preferred are excipients capable of forming complexes, vesicles and/or liposomes that deliver such a compound as defined herein, preferably an oligonucleotide and optionally together with an adjunct compound complexed or trapped in a vesicle or liposome through a cell membrane. Many of these excipients are known in the art. Suitable excipients comprise polyethylenimine (PEI), or similar cationic polymers, including polypropyleneimine or polyethylenimine copolymers (PECs) and derivatives, ExGen 500, synthetic amphiphils (SAINT-18), Lipofectin™, DOTAP and/or viral capsid proteins that are capable of self assembly into particles that can deliver such compounds, preferably an oligonucleotide and optionally together with an adjunct compound as defined herein to a cell, preferably a muscle cell. Such excipients have been shown to efficiently deliver (oligonucleotide such as antisense) nucleic acids to a wide variety of cultured cells, including muscle cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver a compound as defined herein, preferably an oligonucleotide and optionally together with an adjunct compound across cell membranes into cells.

In addition to these common nanoparticle materials, the cationic peptide protamine offers an alternative approach to formulate a compound as defined herein, preferably an oligonucleotide and optionally together with an adjunct compound as colloids. This colloidal nanoparticle system can form so called proticles, which can be prepared by a simple self-assembly process to package and mediate intracellular release of a compound as defined herein, preferably an oligonucleotide and optionally together with an adjunct compound. The skilled person may select and adapt any of the above or other commercially available alternative excipients and delivery systems to package and deliver a compound as defined herein, preferably an oligonucleotide and optionally together with an adjunct compound for use in the current invention to deliver said compound for the treatment of Duchenne Muscular Dystrophy or Becker Muscular Dystrophy in humans.

In addition, a compound as defined herein, preferably an oligonucleotide and optionally together with an adjunct compound could be covalently or non-covalently linked to a targeting ligand specifically designed to facilitate the uptake in to the cell, cytoplasm and/or its nucleus. Such ligand could comprise (i) a compound (including but not limited to peptide (-like) structures) recognising cell, tissue or organ specific elements facilitating cellular uptake and/or (ii) a chemical compound able to facilitate the uptake in to cells and/or the intracellular release of an a compound as defined herein, preferably an oligonucleotide and optionally together with an adjunct compound from vesicles, e.g. endosomes or lysosomes.

Therefore, in a preferred embodiment, a compound as defined herein, preferably an oligonucleotide and optionally together with an adjunct compound are formulated in a medicament which is provided with at least an excipient and/or a targeting ligand for delivery and/or a delivery device of said compound to a cell and/or enhancing its intracellular delivery. Accordingly, the invention also encompasses a pharmaceutically acceptable composition comprising a compound as defined herein, preferably an oligonucleotide and optionally together with an adjunct compound and further comprising at least one excipient and/or a targeting ligand for delivery and/or a delivery device of said compound to a cell and/or enhancing its intracellular delivery.

It is to be understood that an oligonucleotide and an adjunct compound may not be formulated in one single composition or preparation. Depending on their identity, the skilled person will know which type of formulation is the most appropriate for each compound.

In a preferred embodiment the invention provides a kit of parts comprising a compound for providing an individual with a functional dystrophin protein and an adjunct compound for reducing inflammation, preferably for reducing muscle tissue inflammation, and/or an adjunct compound for improving muscle fiber function, integrity and/or survival.

In a preferred embodiment, a concentration of an oligonucleotide as defined herein, which is ranged between about 0.1 nM and about 1 µM is used. More preferably, the concentration used is ranged between about 0.3 to about 400 nM, even more preferably between about 1 to about 200 nM. If several oligonucleotides are used, this concentration may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, a compound preferably an oligonucleotide and an adjunct compound to be used in the invention to prevent, treat DMD or BMD are synthetically produced and administered directly to a cell, a tissue, an organ and/or patients in formulated form in a pharmaceutically acceptable composition or preparation. The delivery of a pharmaceutical composition to the subject is preferably carried out by one or more parenteral injections, e.g. intravenous and/or subcutaneous and/or intramuscular and/or intrathecal and/or intraventricular administrations, preferably injections, at one or at multiple sites in the human body.

Besides exon skipping, it is also possible to provide a DMD patient with a functional dystrophin protein with a therapy based on read-through of stopcodons. Compounds capable of suppressing stopcodons are particularly suitable for a subgroup of DMD patients which is affected by nonsense mutations (~7%) resulting in the formation of a stop codon within their dystrophin gene. In one embodiment said compound capable of suppressing stopcodons comprises the antibiotic gentamicin. In a recent study in mdx mice, gentamicin treatment induced novel dystrophin expression up to 20% of normal level, albeit with variability among animals. Human trials with gentamicin have however been inconclusive[55]. PTC124 belongs to a new class of small molecules that mimics at lower concentrations the readthrough activity of gentamicin. Administration of PTC124 resulted in the production of full-length and functionally active dystrophin both in vitro and in mdx mice[16]. Phase I/II trials with PTC124 are currently ongoing, not only for application in DMD but also for cystic fibrosis[16,17]. The references 16 and 17 also describe preferred dosages of the PCT124 compound for use in the present invention. Further provided is therefore a method, combination, use or pharmaceutical preparation according to the invention, wherein said compound for providing said individual with a functional dystrophin protein comprises a compound for suppressing stop codons. Said compound for suppressing stop codons preferably comprises gentamicin, PTC124 or a functional equivalent thereof. Most preferably, said compound comprises PTC124.

In one embodiment an individual is provided with a functional dystrophin protein using a vector, preferably a viral vector, comprising a micro-mini-dystrophin gene. Most preferably, a recombinant adeno-associated viral (rAAV) vector is used. AAV is a single-stranded DNA parvovirus that is non-pathogenic and shows a helper-dependent life cycle. In contrast to other viruses (adenovirus, retrovirus, and herpes simplex virus), rAAV vectors have demonstrated to be very efficient in transducing mature skeletal muscle. Application of rAAV in classical DMD "gene addition" studies has been hindered by its restricted packaging limits (<5 kb). Therefore, rAAV is preferably applied for the efficient delivery of a much smaller micro- or mini-dystrophin gene. Administration of such micro- or mini-dystrophin gene results in the presence of a at least partially functional dystrophin protein. Reference is made to[18-20].

A compound for providing an individual with a functional dystrophin protein and at least one adjunct compound according to the invention can be administered to an individual in any order. In one embodiment, said compound for providing an individual with a functional dystrophin protein and said at least one adjunct compound are administered simultaneously (meaning that said compounds are administered within 10 hours, preferably within one hour). This is however not necessary. In one embodiment at least one adjunct compound is administered to an individual in need thereof before administration of a compound for providing an individual with a functional dystrophin protein. Further provided is therefore a method according to the invention, comprising:

administering to an individual in need thereof an adjunct compound for reducing inflammation, preferably for reducing muscle tissue inflammation, and/or administering to said individual an adjunct compound for improving muscle fiber function, integrity and/or survival, and, subsequently, administering to said individual a compound for providing said individual with a functional dystrophin protein.

In yet another embodiment, said compound for providing an individual with a functional dystrophin protein is administered before administration of said at least one adjunct compound.

Further provided is a method for at least in part increasing the production of a functional dystrophin protein in a cell, said cell comprising pre-mRNA of a dystrophin gene encoding aberrant dystrophin protein, the method comprising:

providing said cell with a compound for inhibiting inclusion of an exon into mRNA produced from splicing of said dystrophin pre-mRNA, and providing said cell with an adjunct compound for reducing inflammation, preferably for reducing muscle tissue inflammation, and/or providing said cell with an adjunct compound for improving muscle fiber function, integrity and/or survival, the method further comprising allowing translation of mRNA produced from splicing of said pre-mRNA. In one embodiment said method is performed in vitro, for instance using a cell culture.

In this context, increasing the production of a functional dystrophin protein has been earlier defined herein.

Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety.

The invention is further explained in the following examples. These examples do not limit the scope of the invention, but merely serve to clarify the invention.

In a patient with Duchenne's muscular dystrophy who has a deletion of exon 50, an out-of-frame transcript is generated in which exon 49 is spliced to exon 51 (A). As a result, a stop codon is generated in exon 51, which prematurely aborts dystrophin synthesis. The sequence-specific binding of the exon-internal antisense oligonucleotide PRO051 interferes with the correct inclusion of exon 51 during splicing so that the exon is actually skipped (B). This restores the open reading frame of the transcript and allows the synthesis of a dystrophin similar to that in patients with Becker's muscular dystrophy (BMD).

FIGS. 2A-2E. Prescreening Studies of the Four Patients.

Magnetic resonance images of the lower legs of the four patients (the left leg of Patient 3 and right legs of the other three patients) show the adequate condition of the tibialis anterior muscle (less than 50% fat infiltration and fibrosis) (A). The diagnosis of Duchenne's muscular dystrophy in these patients was confirmed by diaminobenzidine tetrahydrochloride staining of cross sections of biopsy specimens obtained previously from the quadriceps muscle (B). No dystrophin expression was observed, with the exception of one dystrophin-positive, or revertant, fiber in Patient 2 (arrow). Reverse-transcriptase-polymerase chain-reaction (RT-PCR) analysis of the transcript region flanking the patients' mutations and exon 51 confirmed both the individual mutations in nontreated myotubes (NT) and the positive response to PRO051 (i.e., exon 51 skipping) in treated myotubes (T) on the RNA level (C). The efficiencies of exon skipping were 49% for Patient 1, 84% for Patient 2, 58% for Patient 3, and 90% for Patient 4. A cryptic splice site within exon 51 is sometimes activated by PRO051 in cell culture, resulting in an extra aberrant splicing product, as seen in the treated sample from Patient 4. Lane M shows a 100-bp size marker, and lane C RNA from healthy control muscle. Sequence analysis of the RT-PCR fragments from treated and untreated myotubes identified the precise skipping of exon 51 for each patient (D). The new in-frame transcripts led to substantial dystrophin synthesis, as detected by immunofluorescence analysis of treated myotubes with the use of monoclonal antibody NCL-DYS2 (E).

No dystrophin was detected before treatment.

Figure 3:
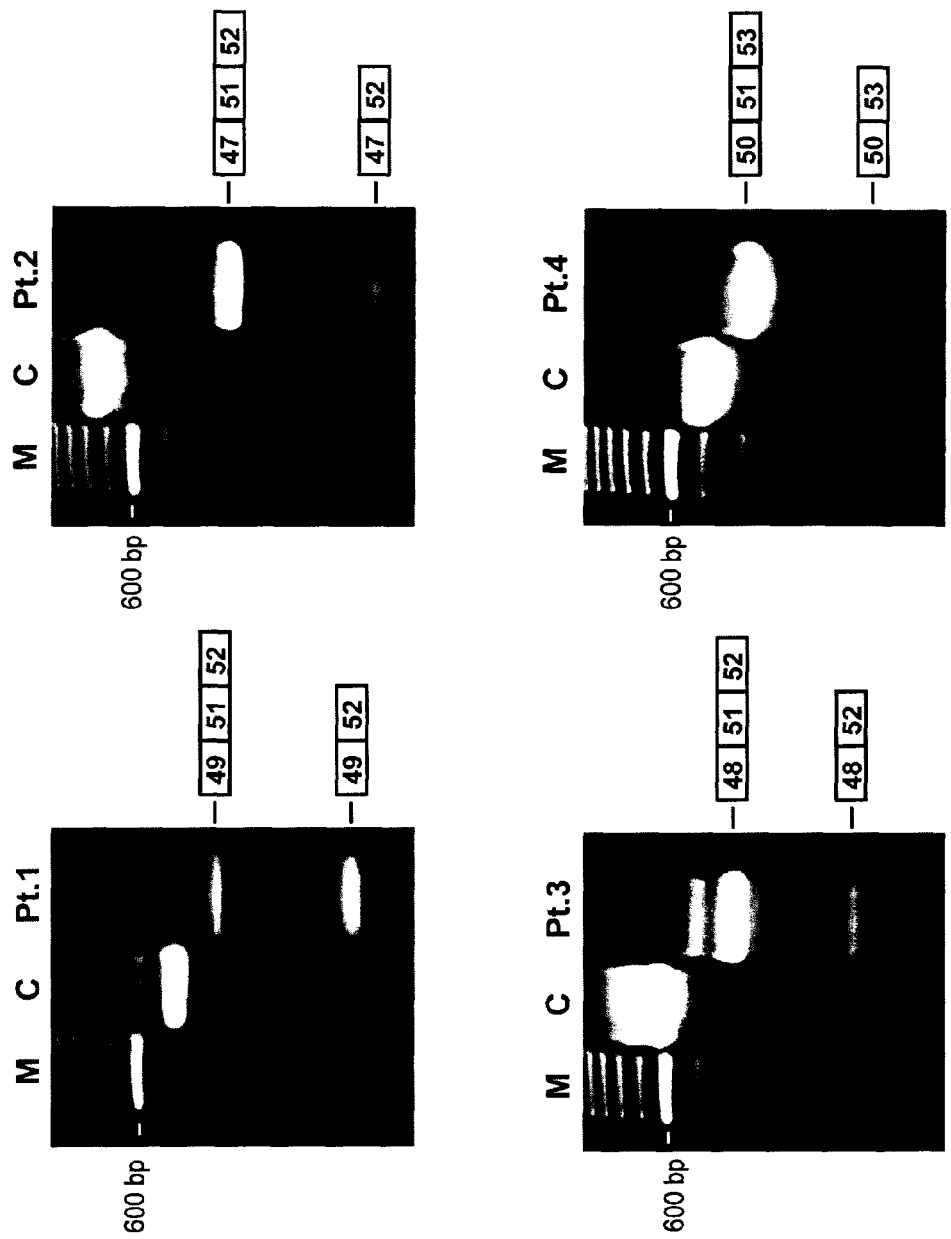

FIG. 3. RT-PCR Analysis of RNA Isolated from Serial Sections of Biopsy Specimens from the Patients.

After treatment with PRO051, reverse-transcriptase-polymerase-chain-reaction (RT-PCR) analysis shows novel, shorter transcript fragments for each patient. Both the size and sequence of these fragments confirm the precise skipping of exon 51. No additional splice variants were observed. At 28 days, still significant in-frame RNA transcripts were detected, suggesting prolonged persistence of PRO051 in muscle. Owing to the small amount of section material, high-sensitivity PCR conditions were used; this process precluded the accurate quantification of skipping efficiencies and the meaningful correlation between levels of RNA and protein. M denotes size marker, and C control.

Figure 4A:
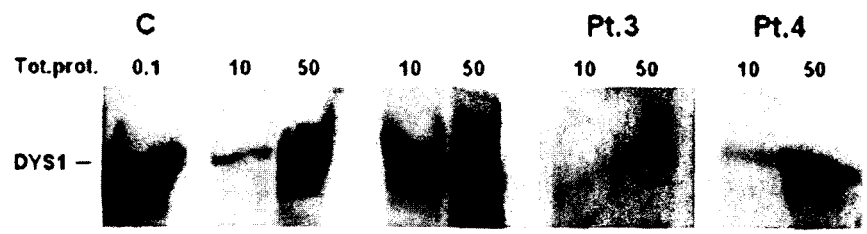
Figure 4B:
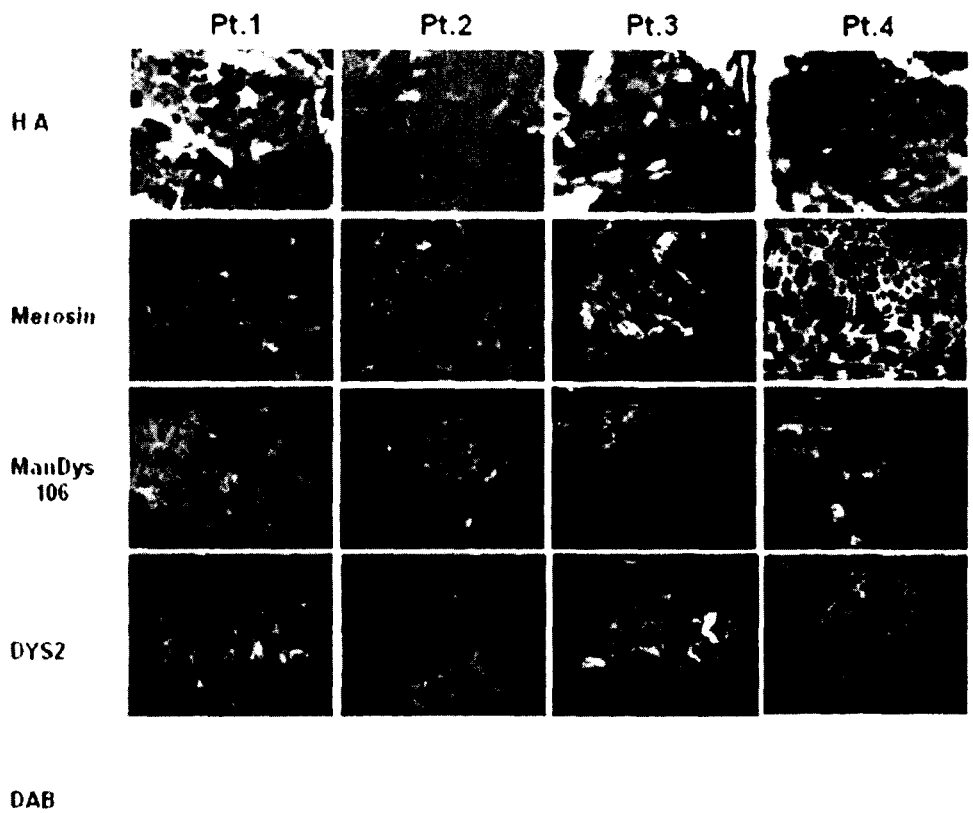

FIGS. 4A-4B. Dystrophin-Restoring Effect of a Single Intramuscular Dose of PRO051. Immuno fluorescence analysis with the use of the dystrophin antibody MANDYS106 clearly shows dystrophin expression at the membranes of the majority of fibers throughout the biopsy specimen obtained from each patient (B). Western blot analysis of total protein extracts isolated from the patients' biopsy specimens with the use of NCL-DYS1 antibody show restored dystrophin expression in all patients (A).

Figure 5:
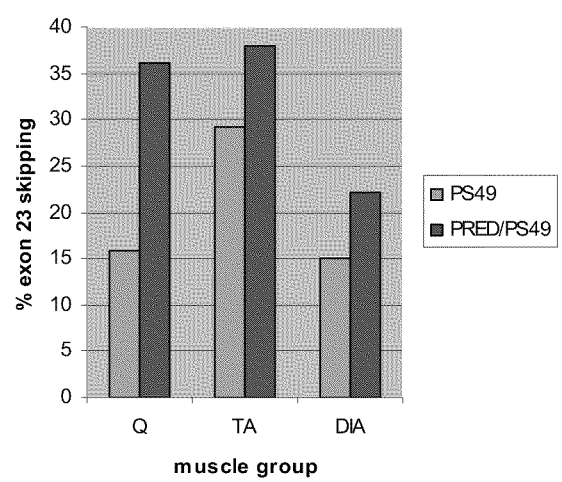

FIG. 5. Exon 23 skipping levels on RNA level in different muscle groups (Q: quadriceps muscle; TA: tibialis anterior muscle; DIA: diaphragm muscle) in mdx mice (two mice per group) treated with PS49 alone (group 3) or with PS49 and prednisolone (group 4).

Figure 6A:
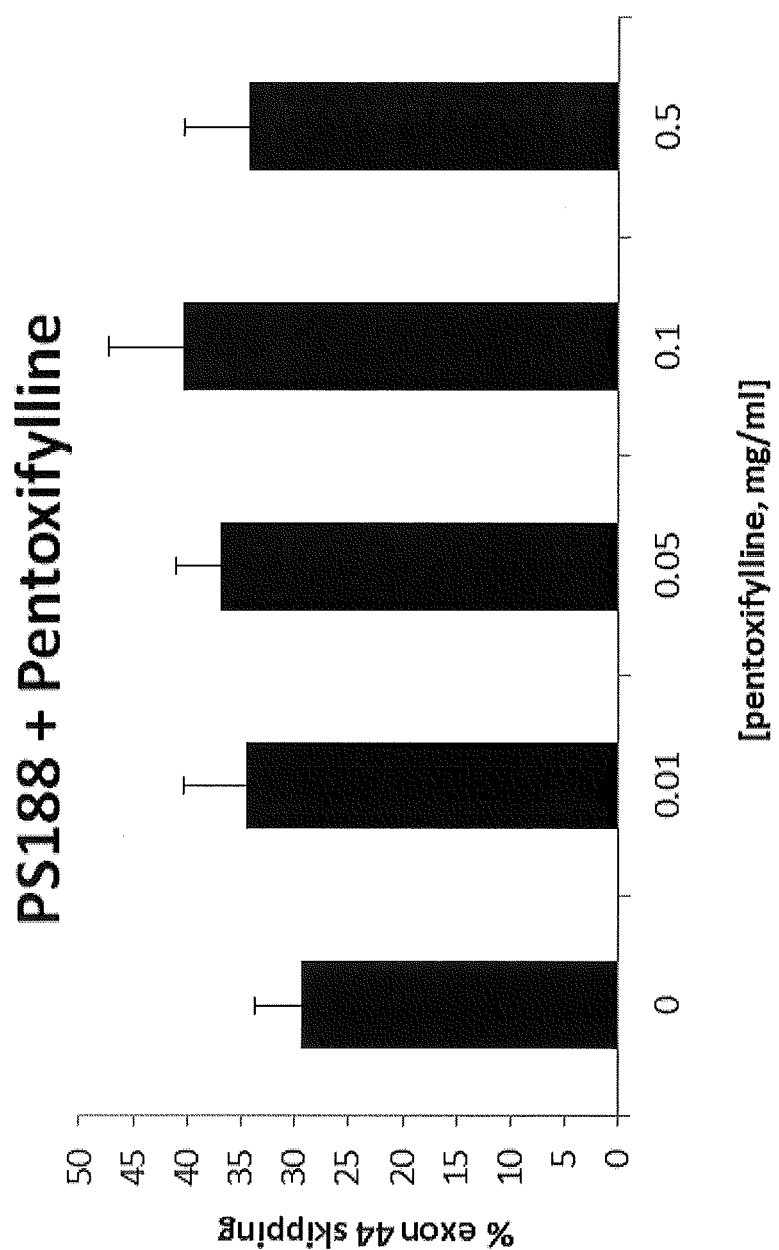
Figure 6B:
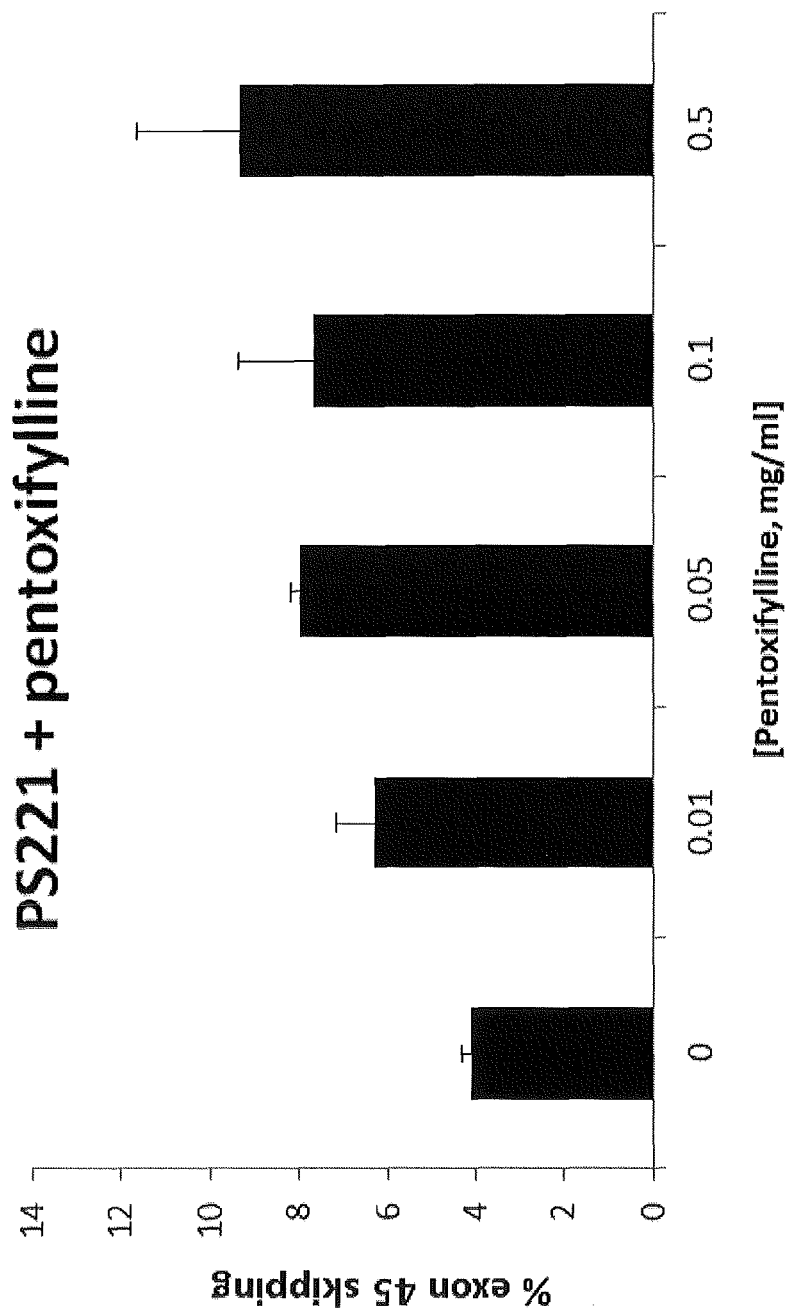
Figure 6C:
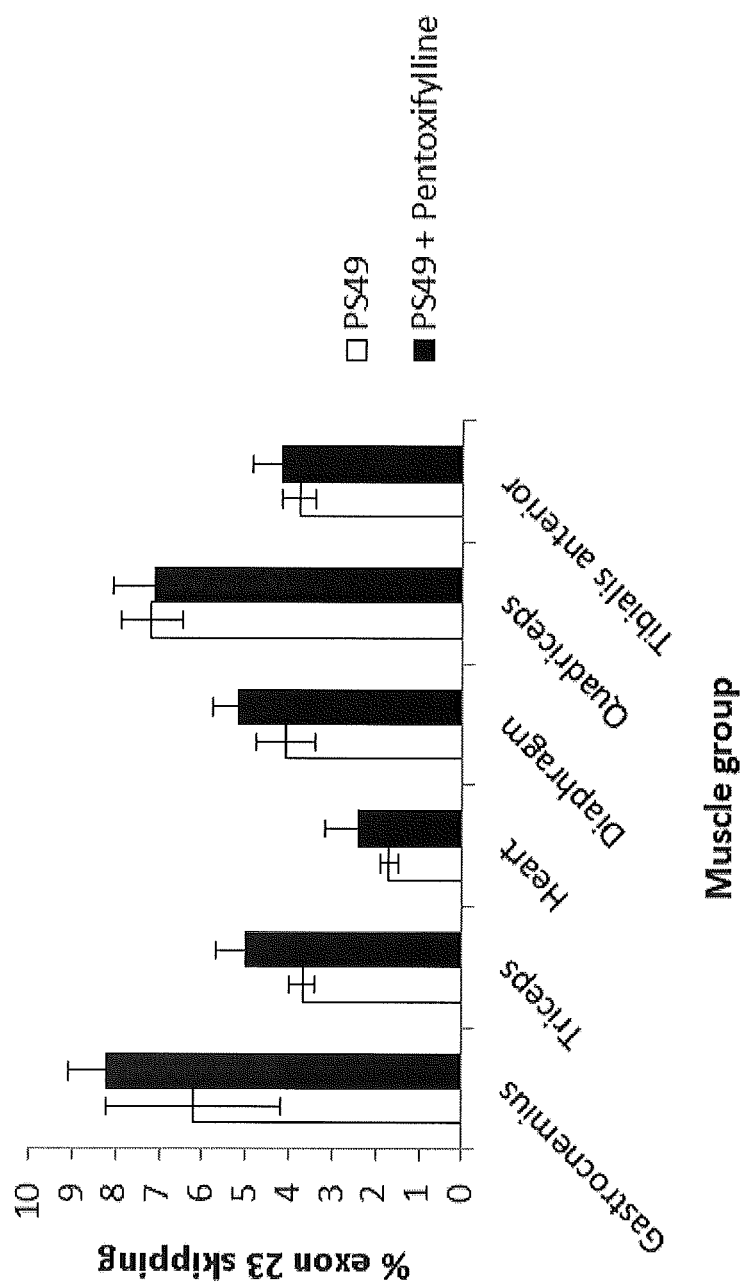

FIGS. 6A-6B. In muscle cells, DMD gene exon 44 (A) or exon 45 (B) skipping levels are enhanced with increasing concentrations of pentoxyfilline (from 0 to 0.5 mg/ml). FIG. 6C Exon 23 skipping levels on RNA level in different muscle groups (Q: quadriceps muscle; TA: tibialis anterior muscle; Tri: triceps muscle; HRT: heart muscle) in mdx mice (two mice per group) treated with PS49 alone (group 3) or with PS49 and pentoxyfilline (group 4).

FIGS. 7A-7B. Dystrophin (DMD) gene amino acid sequence

FIG. 8. Human IGF-1 Isoform 4 amino acid sequence.

FIGS. 9A-9M. Various oligonucleotides directed against the indicated exons of the dystrophin 20 (DMD)

EXAMPLES

Example 1

In a recent clinical study the local safety, tolerability, and dystrophin-restoring effect of antisense compound PRO051 was assessed. The clinical study was recently published. The content of the publication is reproduced herein under example 1A. In brief, PRO051 is a synthetic, modified RNA molecule with sequence 5'-UCA AGG AAG AUG GCA UUU CU-3', and designed to specifically induce exon 51 skipping[59]. It carries full-length 2'-O-methyl substituted ribose moieties and phosphorothioate internucleotide linkages. Four DMD patients with different specific DMD gene deletions correctable by exon 51 skipping were included. At day 0, a series of safety parameters was assessed. The patient's leg (i.e. tibialis anterior muscle) was fixed with a tailor-made plastic mould and its position was carefully recorded. A topical anesthetic (EMLA) was used to numb the skin Four injections of PRO051 were given along a line of 1.5 cm between two small skin tattoos, using a 2.5 cm electromyographic needle (MyoJect Disposable Hypodermic Needle Electrode, TECA Accessories) to ensure intramuscular delivery. Each injection volume was 200 μl, containing 200 μg PRO051, dispersed in equal portions at angles of approximately 30 degrees. At day 28, the same series of safety parameters was assessed again. The leg was positioned using the patient's own mould, and a semi-open muscle biopsy was taken between the tattoos under local anesthesia using a forceps with two sharp-edged jaws (Blakesley Conchotoma, DK Instruments). The biopsy was snap-frozen in liquid nitrogen-cooled 2-methylbutane. Patients were treated sequentially. At the time of study, two patients (nr. 1 and 2) were also on corticosteroids (prednisone or deflazacort), one had just stopped steroid treatment (nr. 4) and one patient never used steroids (nr. 3) (see Table 1). This latter patient was also the one who lost ambulance at the youngest age when compared to the other three patients. The biopsy was analysed, for detection of specific exon skipping on RNA level (RT-PCR analysis, not shown) and novel expression of dystrophin on protein level (immunofluorescence and western blot analyses, summarized in Table 1). Assessment of the series of safety parameters (routine plasma and urine parameters for renal and liver function, electrolyte levels, blood cell counts, hemoglobin, aPTT, AP50 and CH50 values) before and after treatment, indicated that the PRO051 compound was locally safe and well tolerated. For immunofluorescence analysis, acetone-fixed cross-sections of the biopsy were incubated for 90 minutes with monoclonal antibodies against the central rod domain (MANDYS106, Dr. G. Morris, UK, 1:60), the C-terminal domain (NCL-DYS2, Novocastra Laboratories Ltd., 1:30) or, as reference, laminin-α2 (Chemicon International, Inc, 1:150), followed by Alexa Fluor 488 goat anti-mouse IgG (H+L) (Molecular Probes, Inc, 1:250) antibody for one hour. Sections were mounted with Vectashield Mounting Medium (Vector Laboratories Inc.). For quantitative image analysis the ImageJ software (W. Rasband, NIH, USA; http://rsb.info.nih.gov/ij) was used as described[60,61]. Entire cross-sections were subdivided into series of 6-10 adjacent images, depending on section size. To ensure reliable measurements, staining of the sections and recording of all images was performed in one session, using fixed exposure settings, and avoiding pixel saturation. The lower intensity threshold was set at Duchenne muscular dystrophy background, and positive fluorescence was quantified for each section (area percentage), both for dystrophin and laminin-α2. Western blot analysis was performed as described[1], using pooled homogenates from sets of four serial 50 µm sections throughout the biopsy. For the patients 30 and 60 µg total protein was applied and for the control sample 3 µg. The blot was incubated overnight with dystrophin monoclonal antibody NCL-DYS1 (Novocastra Laboratories, 1:125), followed by goat anti-mouse IgG-HRP (Santa Cruz Biotechnology, 1:10.000) for one hour Immuno-reactive bands were visualized using the ECL Plus Western Blotting Detection System (GE Healthcare) and Hyperfilm ECL (Amersham, Biosciences). Signal intensities were measured using ImageJ. Novel dystrophin protein expression at the sarcolemma was detected in the majority of muscle fibers in the treated area in all four patients. The fibers in each section were manually counted after staining for laminin-α2, a basal lamina protein unaffected by dystrophin deficiency. The individual numbers varied, consistent with the biopsy size and the quality of the patients' muscles. In the largest sections, patient 2 had 726 fibers, of which 620 were dystrophin-positive, while patient 3 had 120 fibers, of which 117 were dystrophin-positive. The dystrophin intensities were typically lower than those in a healthy muscle biopsy. Western blot analysis confirmed the presence of dystrophin in varying amounts. The dystrophin signals were scanned and correlated to the control (per µg total protein). The amounts varied from 3% in patient 3 with the most dystrophic muscle, to 12% in patient 2 with the best preserved muscle. Since such comparison based on total protein does not correct for the varying amounts of fibrotic and adipose tissue in Duchenne muscular dystrophy patients, we also quantified the dystrophin fluorescence signal relative to that of the similarly-located laminin-α2 in each section, by ImageJ analysis. When this dystrophin/laminin-α2 ratio was set at 100% for the control section, the two patients that were co-treated with corticosteroids showed the highest percentages of dystrophin, 32% in patient 1 and 35% in patient 2 (Table 1). The lowest percentage of dystrophin was detected in patient 3, 17%. In patient 4 an intermediate percentage of 25% was observed. These percentages correlated to the relative quality of the target muscle, which was best in patients nr. 1 and 2, and worst in patient nr. 3.

TABLE 1

|  | Patient 1 | Patient 2 | Patient 3 | Patient 4 |
| --- | --- | --- | --- | --- |
| Age (yrs) | 10 | 13 | 13 | 11 |
| Age at Loss of Ambulation (yrs) | 9 | 11 | 7 | 10 |
| Steroid Treatment | Yes | Yes | Never | Until January 2006 |
| Ratio Dystrophin/ laminin-alpha2 | 32% | 35% | 17% | 25% |

Conclusion: the effect of the PRO051 antisense compound was more prominent in those patients that were also subjected to corticosteroids.

Example 1A

Reproduced from Van Deutekom J C et al, (2007) Antisense Oligonucleotide PRO051 Restores Local Dystrophin in DMD Patients. N Engl J. Med., 357(26): 2677-86.

Methods

Patients and Study Design

Patients with Duchenne's muscular dystrophy who were between the ages of 8 and 16 years were eligible to participate in the study. All patients had deletions that were correctable by exon-51 skipping and had no evidence of dystrophin on previous diagnostic muscle biopsy. Concurrent glucocorticoid treatment was allowed. Written informed consent was obtained from the patients or their parents, as appropriate. During the prescreening period (up to 60 days), each patient's mutational status and positive exon-skipping response to PRO051 in vitro were confirmed, and the condition of the tibialis anterior muscle was determined by $T_1$-weighted magnetic resonance imaging (MRI).[62] For patients to be included in the study, fibrotic and adipose tissue could make up no more than 50% of their target muscle.

During the baseline visit, safety measures were assessed. In each patient, the leg that was to be injected was fixed with a tailor-made plastic mold and its position was recorded. A topical eutectic mixture of local anesthetics (EMLA) was used to numb the skin. Four injections of PRO051 were given along a line measuring 1.5 cm running between two small skin tattoos with the use of a 2.5-cm electromyographic needle (MyoJect Disposable Hypodermic Needle Electrode, TECA Accessories) to ensure intramuscular delivery. The volume of each injection was 200 µl containing 200 µg of PRO051, which was dispersed in equal portions at angles of approximately 30 degrees.

At day 28, safety measures were assessed again. The leg that had been injected was positioned with the use of the patient's own mold, and a semiopen muscle biopsy was performed between the tattoos under local anesthesia with a forceps with two sharp-edged jaws (Blakesley Conchotoma, DK Instruments).[63] The biopsy specimen was snap-frozen in 2-methylbutane cooled in liquid nitrogen.

Patients were treated sequentially from May 2006 through March 2007 and in compliance with Good Clinical Practice guidelines and the provisions of the Declaration of Helsinki. The study was approved by the Dutch Central Committee on Research Involving Human Subjects and by the local institutional review board at Leiden University Medical Center. All authors contributed to the study design, participated in the collection and analysis of the data, had complete and free access to the data, jointly wrote the manuscript, and vouch for the completeness and accuracy of the data and analyses presented.

Description of PRO051

PRO051 is a synthetic, modified RNA molecule with sequence 5'-UCAAGGAAGAUGGCAUUUCU-3'.[12] It carries full-length 2'-O-methyl-substituted ribose molecules and phosphorothioate internucleotide linkages. The drug was provided by Prosensa B.V. in vials of 1 mg of freeze-dried material with no excipient. It was dissolved and administered in sterile, unpreserved saline (0.9% sodium chloride). PRO051 was not found to be mutagenic by bacterial Ames testing. In regulatory Good Laboratory Practice safety studies, rats that received a single administration of up to 8 mg per kilogram of body weight intramuscularly and 50 mg per kilogram intravenously showed no adverse effects; monkeys receiving PRO051 for 1 month appeared to tolerate doses up to 16 mg per kilogram per week when the drug was administered by intravenous 1-hour infusion or by subcutaneous injection, without clinically relevant adverse effects.

In Vitro Prescreening

A preexisting primary myoblast culture[1] was used for the prescreening of Patient 4. For the other three patients, fibroblasts were converted into myogenic cells after infection with an adenoviral vector containing the gene for the myogenic transcription factor (MyoD) as described previously.[1,64,65] Myotube cultures were transfected with PRO051 (100 nM) and polyethylenimine (2 μl per microgram of PRO051), according to the manufacturer's instructions for ExGen500 (MBI Fermentas). RNA was isolated after 48 hours. Reverse transcriptase–polymerase chain reaction (RT-PCR), immunofluorescence, and Western blot analyses were performed as reported previously[1,12] PCR fragments were analyzed with the use of the 2100 Bioanalyzer (Agilent) and isolated for sequencing by the Leiden Genome Technology Center.

Safety Assessment

At baseline and at 2 hours, 1 day, and 28 days after injection, all patients received a full physical examination (including the measurement of vital signs) and underwent electrocardiography. In addition, plasma and urine were obtained to determine renal and liver function, electrolyte levels, complete cell counts, the activated partial-thromboplastin time, and complement activity values in the classical (CH50) and alternative (AP50) routes. The use of concomitant medications was recorded. At baseline and on day 28, the strength of the tibialis anterior muscle was assessed with the use of the Medical Research Council scale[66] to evaluate whether the procedures had affected muscle performance. (On this scale, a score of 0 indicates no movement and a score of 5 indicates normal muscle strength.) Since only a small area of the muscle was treated, clinical benefit in terms of increased muscle strength was not expected. At each visit, adverse events were recorded.

RNA Assessment

Serial sections (50 μm) of the frozen muscle-biopsy specimen were homogenized in RNA-Bee solution (Campro Scientific) and MagNA Lyser Green Beads (Roche Diagnostics). Total RNA was isolated and purified according to the manufacturer's instructions. For complementary DNA, synthesis was accomplished with Transcriptor reverse transcriptase (Roche Diagnostics) with the use of 500 ng of RNA in a 20-μl reaction at 55° C. for 30 minutes with human exon 53 or 54 specific reverse primers. PCR analyses were performed as described previously.[1,12] Products were analyzed on 2% agarose gels and sequenced. In addition, RT-PCR with the use of a primer set for the protein-truncation test[67] was used to rapidly screen for aspecific aberrant splicing events throughout the DMD gene.

Assessment of Protein Level

For immunofluorescence analysis, acetone-fixed sections were incubated for 90 minutes with monoclonal antibodies against the central rod domain (MANDYS106, Dr. G. Morris, United Kingdom) at a dilution of 1:60, the C-terminal domain (NCL-DYS2, Novocastra Laboratories) at a dilution of 1:30, or (as a reference) laminin (Chemicon International), a basal lamina protein that is unaffected by dystrophin deficiency, at a dilution of 1:150, followed by Alexa Fluor 488 goat anti-mouse IgG (H+L) antibody (Molecular Probes) at a dilution of 1:250 for 1 hour. Sections were mounted with Vectashield Mounting Medium (Vector Laboratories). ImageJ software (W. Rasband, National Institutes of Health, http://rsb.info.nih.gov/ij) was used for quantitative image analysis as described previously.[60,61] Entire cross sections were subdivided into series of 6 to 10 adjacent images, depending on the size of the section. To ensure reliable measurements, staining of the sections and recording of all images were performed during one session with the use of fixed exposure settings and the avoidance of pixel saturation. The lower-intensity threshold was set at background for Duchenne's muscular dystrophy, and positive fluorescence was quantified for each section (area percentage), both for dystrophin and laminin α2.

Western blot analysis was performed as described previously[1] with the use of pooled homogenates from sets of four serial 50-μm sections throughout the biopsy specimen. For each patient, two amounts of total protein—30 μg and 60 μg—were applied, and for the control sample, 3 μg. The Western blot was incubated overnight with dystrophin monoclonal antibody NCL-DYS1 (Novocastra Laboratories) at a dilution of 1:125, followed by horseradish-peroxidase-labeled goat antimouse IgG (Santa Cruz Biotechnology) at a dilution of 1:10,000 for 1 hour. Immunoreactive bands were visualized with the use of the ECL Plus Western blotting detection system (GE Healthcare) and Hyperfilm ECL (Amersham Biosciences). Signal intensities were measured with the use of ImageJ software.

Results

Prescreening of Patients

Figure 1:
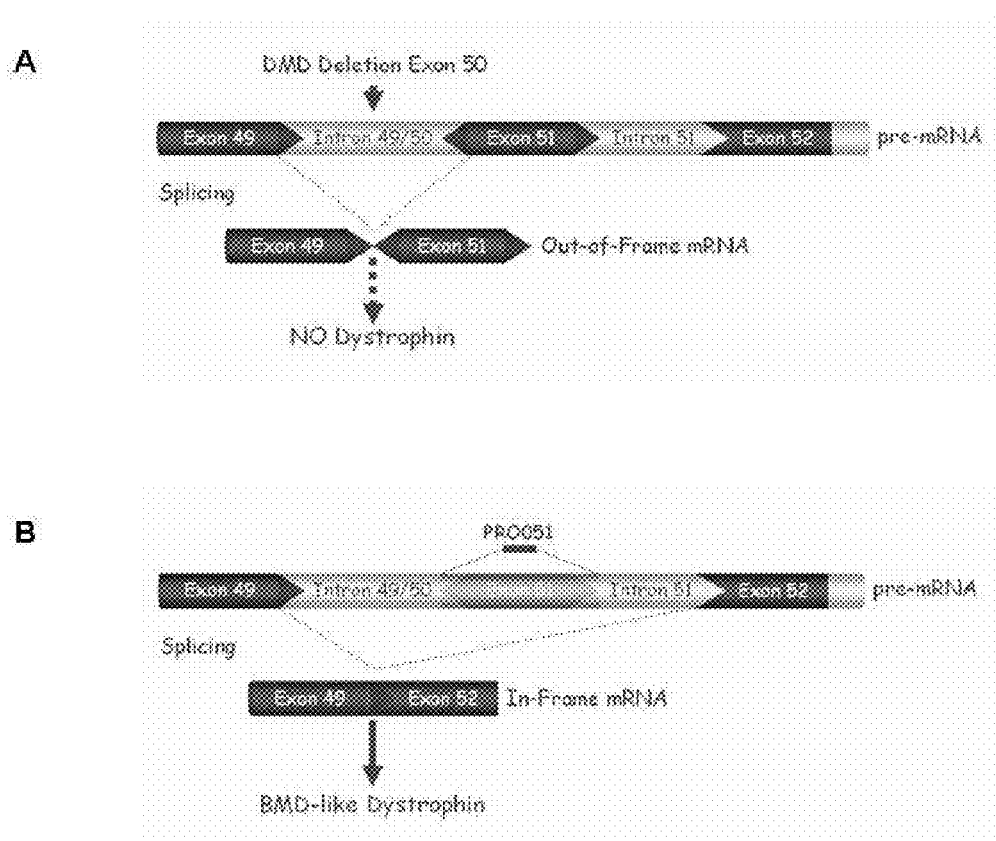
FIGS. 1A-1B. Schematic Representation of Exon Skipping.
Figure 2A:
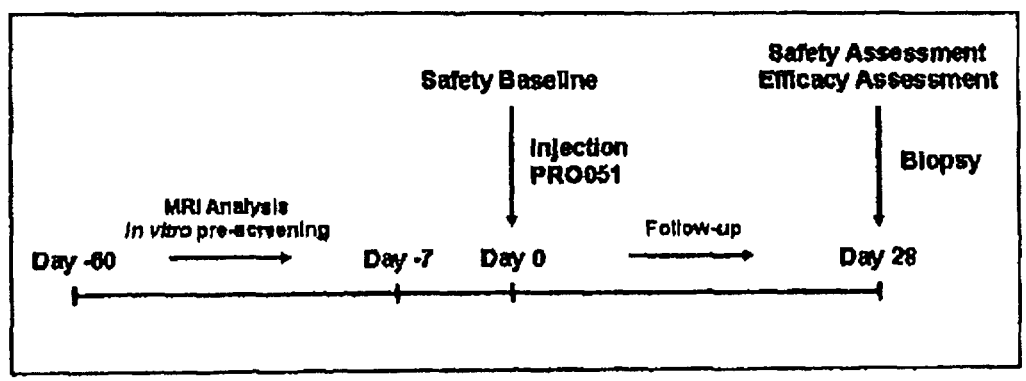
Figure 2C:
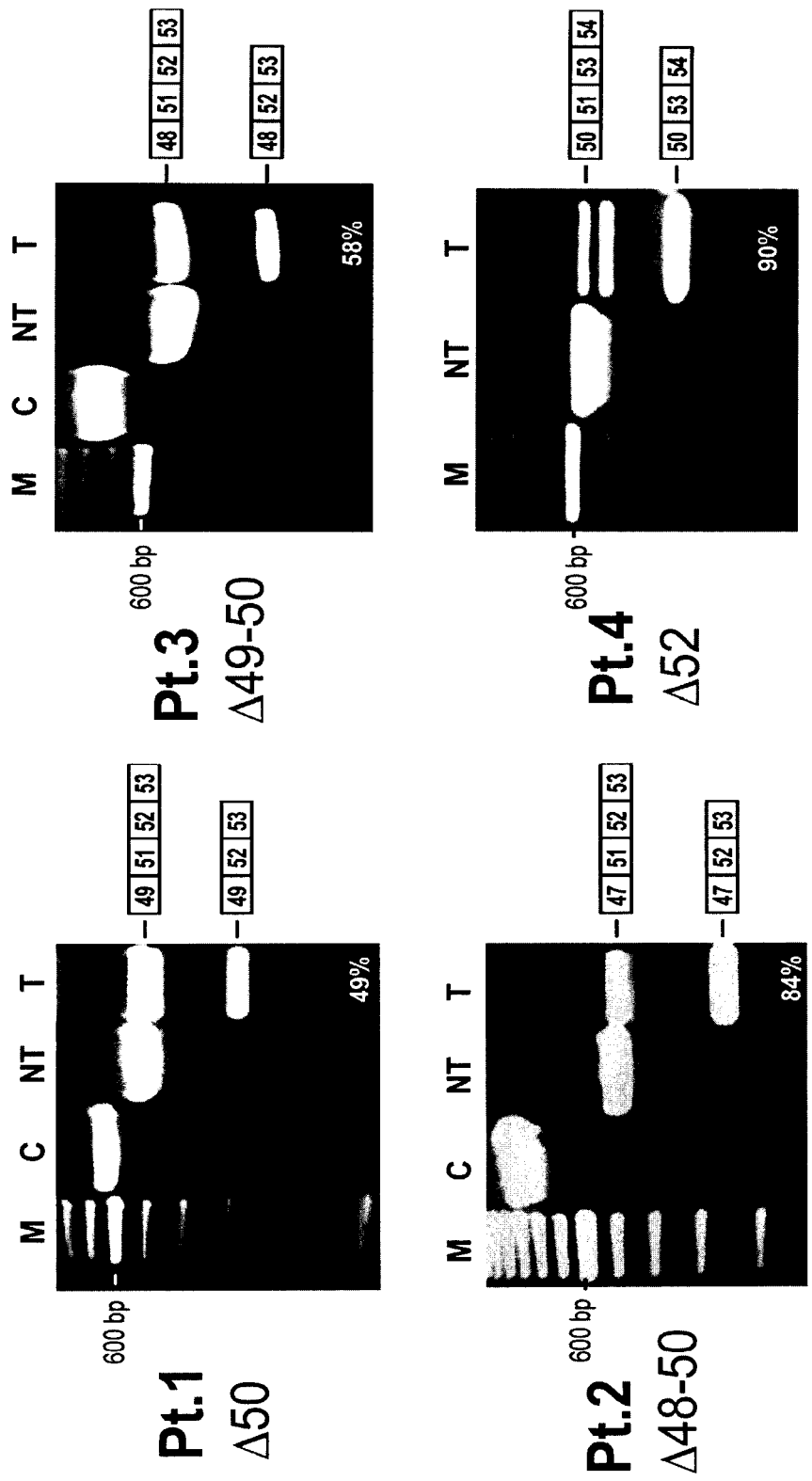
Figure 2D:
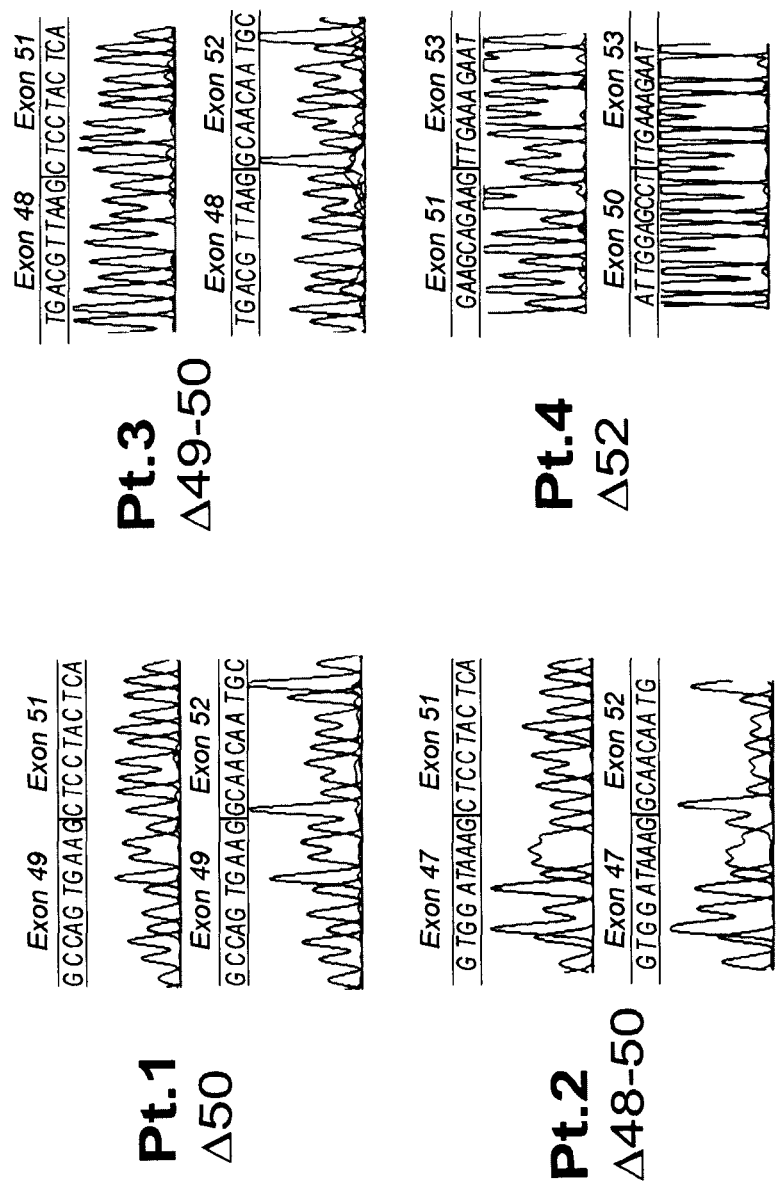

The study was planned to include four to six patients. Six patients were invited to participate, and one declined. The remaining five patients were prescreened. First, the condition of the tibialis anterior muscle was evaluated on MRI. The muscle condition of four patients was deemed to be adequate for the study (FIG. 2B), and the absence of dystrophin was confirmed in the patients' original biopsy specimens (FIG. 2B). Second, the mutational status and positive exon-skipping response to PRO051 of these four patients were confirmed in fibroblast cultures. PRO051 treatment generated a novel, shorter fragment of messenger RNA for each patient, representing 46% (in Patient 4) to 90% (in Patient 1) of the total RT-PCR product (FIG. 2C). Precise exon-51 skipping was confirmed by sequencing (FIG. 2D). No other transcript regions were found to be altered. Immunofluorescence analyses showed a preponderance of dystrophin-positive myotubes (FIG. 2E), a finding that was confirmed by Western blot analysis (not shown). Thus, the four patients were judged to be eligible for PRO051 treatment. Their baseline characteristics are shown in Table 2.

Safety and Adverse Events

All patients had one or more adverse events. However, only one patient reported mild local pain at the injection site, which was considered to be an adverse event related to the study drug. Other events included mild-to-moderate pain after the muscle biopsy. Two patients had blistering under the bandages used for wound closure. In the period between injection and biopsy, two patients reported a few days of flulike symptoms, and one patient had mild diarrhea for 1 day. At baseline, the muscle-strength scores of the treated tibialis anterior muscle in Patients 1, 2, 3, and 4 were 4, 2, 3, and 4, respectively, on the Medical Research Council scale. None of the patients showed changes in the strength of this muscle during the study or significant alterations in standard laboratory measures or increased measures of complement split products or activated partial-thromboplastin time. No local inflammatory or toxic response was detected in the muscle sections of the patients (data not shown). Patient 3 successfully underwent preplanned surgery for scoliosis in the month after the study was completed.

RNA and Protein Level

At day 28, a biopsy of the treated area was performed in each patient. Total muscle RNA was isolated from serial sections throughout the biopsy specimen. In all patients, RT-PCR identified a novel, shorter fragment caused by exon-51 skipping, as confirmed by sequencing (FIG. 3). Further transcript analysis showed no other alterations (data not shown). Immunofluorescence analyses of sections throughout the biopsy specimen of each patient showed clear sarcolemmal dystrophin signals in the majority of muscle fibers (FIGS. 4A and 4B). Dystrophin antibodies proximal and distal to the deletions that were used included MANDYS106 (FIGS. 4A and 4B) and NCL-DYS2 (similar to MANDYS106, not shown). The fibers in each section were manually counted after staining for laminin α2.[68] The individual numbers varied, consistent with the size of the biopsy specimen and the quality of the muscle. In the largest sections, Patient 2 had 726 fibers, of which 620 were dystrophin-positive, whereas Patient 3 had 120 fibers, of which 117 were dystrophin-positive (Data not shown). The dystrophin intensities were typically lower than those in a healthy muscle biopsy specimen (Data not shown). The single fibers with a more intense dystrophin signal in Patients 2 and 3 could well be revertant fibers (Data not shown).

Western blot analysis confirmed the presence of dystrophin in varying amounts (FIG. 4A). The dystrophin signals were scanned and correlated to the control (per microgram of total protein). The amounts varied from 3% in Patient 3, who had the most-dystrophic muscle, to 12% in Patient 2, who had the best-preserved muscle. Since such comparison on the basis of total protein does not correct for the varying amounts of fibrotic and adipose tissue in patients with Duchenne's muscular dystrophy, we also quantified the dystrophin fluorescence signal (Data not shown) relative to that of the similarly located laminin α2 in each section by ImageJ analysis. When the ratio of dystrophin to laminin α2 was set at 100 for the control section, Patients 1, 2, 3, and 4 had ratios of 33, 35, 17, and 25, respectively (Table 1).

Discussion

Our study showed that local intramuscular injection of PRO051, a 2OMePS antisense oligoribonucleotide complementary to a 20-nucleotide sequence within exon 51, induced exon-51 skipping, corrected the reading frame, and thus introduced dystrophin in the muscle in all four patients with Duchenne's muscular dystrophy who received therapy. Dystrophin-positive fibers were found throughout the patients' biopsy specimens, indicating dispersion of the compound in the injected area. Since no delivery-enhancing excipient was used, PRO051 uptake did not seem to be a major potentially limiting factor. We cannot rule out that increased permeability of the dystrophic fiber membrane had a favorable effect. The patients produced levels of dystrophin that were 3 to 12% of the level in healthy control muscle, as shown on Western blot analysis of total protein. Since the presence of fibrosis and fat may lead to some underestimation of dystrophin in total protein extracts, we determined the ratio of dystrophin to laminin α2 in the cross sections, which ranged from 17 to 35, as compared with 100 in control muscle. The dystrophin-restoring effect of PRO051 was limited to the treated area, and no strength improvement of the entire muscle was observed. Future systemic treatment will require repeated administration to increase and maintain dystrophin expression at a higher level and to obtain clinical efficacy.

Because of medical-ethics regulations regarding interventions in minors, we could not obtain a biopsy specimen from the patients' contralateral muscles that had not been injected. However, the patients showed less than 1% of revertant fibers in the original diagnostic biopsy specimens obtained 5 to 9 years before the initiation of the study (Table 2 and FIG. 2B). We consider it very likely that the effects we observed were related to the nature and sequence of the PRO051 reagent rather than to a marked increase in revertant fibers. Indeed, a single, possibly revertant fiber that had an increased dystrophin signal was observed in both Patient 2 and Patient 3 (FIG. 4B).

In summary, our study showed that local administration of PRO051 to muscle in four patients with Duchenne's muscular dystrophy restored dystrophin to levels ranging from 3 to 12% or 17 to 35%, depending on quantification relative to total protein or myofiber content. Consistent with the distinctly localized nature of the treatment, functional improvement was not observed. The consistently poorer result in Patient 3, who had the most advanced disease, suggests the importance of performing clinical trials in patients at a relatively young age, when relatively little muscle tissue has been replaced by fibrotic and adipose tissue. Our findings provide an indication that antisense-mediated exon skipping may be a potential approach to restoring dystrophin synthesis in the muscles of patients with Duchenne's muscular dystrophy.

Example 2

In a pre-clinical study in mdx mice (animal model for DMD) the effect of adjunct compound prednisone on AON-induced exon skipping was assessed.

Mdx mice (C57Bl/10ScSn-mdx/J) were obtained from Charles River Laboratories (The Netherlands). These mice are dystrophin-deficient due to a nonsense mutation in exon 23. AON-induced exon 23 skipping is therapeutic in mdx mice by removing the nonsense mutation and correction of the open reading frame. Two mdx mice per group were injected subcutaneously with: Group 1) physiologic salt (wk 1-8), Group 2) prednisolone (1 mg/kg, wk 1-8), Group 3) mouse-specific antisense oligonucleotide PS49 designed to specifically induce exon 23 skipping (100 mg/kg, wk 4 (5 times), week 5-8 (2 times), Group 4) prednisolone (1 mg/kg, wk 1-8)+PS49 (100 mg/kg, wk 4 (5 times), week 5-8 (2 times). PS49 (5' GGCCAAACCUCGGCUUACCU 3') has a full-length phosphorothioate backbone and 2'O-methyl modified ribose molecules.

All mice were sacrificed at 1 week post-last-injection. Different muscles groups, including quadriceps, tibialis anterior, and diaphragm muscles were isolated and frozen in liquid nitrogen-cooled 2-methylbutane. For RT-PCR analysis, the muscle samples were homogenized in the RNA-Bee solution (Campro Scientific, The Netherlands). Total RNA was isolated and purified according to the manufacturer's instructions. For cDNA synthesis with reverse transcriptase (Roche Diagnostics, The Netherlands), 300 ng of RNA was used in a 20 μl reaction at 55° C. for 30 min, reverse primed with mouse DMD gene-specific primers. First PCRs were performed with outer primer sets, for 20 cycles of 94° C. (40 sec), 60° C. (40 sec), and 72° C. (60 sec). One μl of this reaction (diluted 1:10) was then re-amplified using nested primer combinations in the exons directly flanking exon 23, with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands). No exon 23 skipping was observed in the muscles from mice treated with physiologic salt or prenisolone only (groups 1 and 2). Levels of exon 23 skipping were detected and per muscle group compared between mice treated with PS49 only (group 3) and mice treated with PS49 and adjunct compound prednisolone (group 4). In the quadriceps (Q), tibialis anterior (TA), and diaphragm (DIA) muscles, exon 23 skipping levels were typically higher in group 4 when compared to group 3 (FIG. 5). This indicates that adjunct compound prednisolone indeed enhances exon 23 skipping levels in mdx mice treated with PS49.

Example 3

A., B. Differentiated muscle cell cultures (myotubes) derived from a healthy control individual were transfected with 250 nM PS188 ([5' UCAGCUUCUGUUAGCCACUG 3'; SEQ ID NO:10] an AON optimized to specifically skip exon 44) or 250 nM PS221 ([5'AUUCAAUGUUCUGA-CAACAGUUUGC 3'; SEQ ID NO: 60] an AON optimized to specifically skip exon 45) in the presence of 0 to 0.5 mg/ml pentoxifylline, using the transfection reagent polymer UNIFectylin (2.0 µl UNIFectylin per µg AON in 0.15M NaCl). UNIFectylin interacts electrostatically with nucleic acids, provided that the nucleic acid is negatively charged (such as 2'-O-methyl phosphorothioate AONs). Pentoxyfillin (Sigma Aldrich) was dissolved in water. Total RNA was isolated 24 hrs after transfection in RNA-Bee solution (Campro Scientific, The Netherlands) according to the manufacturer's instructions. For cDNA synthesis with reverse transcriptase (Roche Diagnostics, The Netherlands), 500 ng of RNA was used in a 20 µl reaction at 55° C. for 30 min, reverse primed with DMD gene-specific primers. First PCRs were performed with outer primer sets, for 20 cycles of 94° C. (40 sec), 60° C. (40 sec), and 72° C. (60 sec). One µl of this reaction (diluted 1:10) was then re-amplified using nested primer combinations in the exons directly flanking exon 44 or 45, with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands).

Both with PS188 and PS221, increasing levels of exon 44 or 45 skipping were obtained with increasing concentrations of the adjunct compound pentoxifylline when compared to those obtained in cells that were not co-treated with pentoxyfilline (see FIG. 6). These results indicate that pentoxifylline enhances exon skipping levels in the muscle cells.

C.

In a pre-clinical study in mdx mice (animal model for DMD) the effect of adjunct compound pentoxyfilline on AON-induced exon skipping was assessed. Mdx mice (C57Bl/10ScSn-mdx/J) were obtained from Charles River Laboratories (The Netherlands). These mice are dystrophin-deficient due to a nonsense mutation in exon 23. AON-induced exon 23 skipping is therapeutic in mdx mice by removing the nonsense mutation and correction of the open reading frame. Two mdx mice per group were injected subcutaneously with: Group 1) pentoxyfilline (50 mg/kg, wk 1-2), Group 2) mouse-specific antisense oligonucleotide PS49 designed to specifically induce exon 23 skipping (100 mg/kg, wk 2 (2 times), Group 3) pentoxyfilline (50 mg/kg, wk 1-2)+ PS49 (100 mg/kg, wk 2 (2 times). PS49 (5' GGCCAAAC-CUCGGCUUACCU 3') has a full-length phosphorothioate backbone and 2'O-methyl modified ribose molecules.

All mice were sacrificed at 1 week post-last-injection. Different muscles groups, including quadriceps, tibialis anterior, triceps and heart muscles were isolated and frozen in liquid nitrogen-cooled 2-methylbutane. For RT-PCR analysis, the muscle samples were homogenized in the RNA-Bee solution (Campro Scientific, The Netherlands). Total RNA was isolated and purified according to the manufacturer's instructions. For cDNA synthesis with reverse transcriptase (Roche Diagnostics, The Netherlands), 300 ng of RNA was used in a 20 µl reaction at 55° C. for 30 min, reverse primed with mouse DMD gene-specific primers. First PCRs were performed with outer primer sets, for 20 cycles of 94° C. (40 sec), 60° C. (40 sec), and 72° C. (60 sec). One µl of this reaction (diluted 1:10) was then re-amplified using nested primer combinations in the exons directly flanking exon 23, with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands). No exon 23 skipping was observed in the muscles from mice treated with pentoxyfilline only (groups 1). Levels of exon 23 skipping were detected and per muscle group compared between mice treated with PS49 only (group 2) and mice treated with PS49 and adjunct compound pentoxyfilline (group 3). In the quadriceps (Q), tibialis anterior (TA), triceps (Tri) and heart (HRT) muscles, exon 23 skipping levels were typically higher in group 3 when compared to group 2 (FIG. 6c). This indicates that adjunct compound pentoxyfilline indeed enhances exon 23 skipping levels in mdx mice treated with PS49.

TABLE 2

Baseline characteristics of the DMD patients

|  | Patient 1 | Patient 2 | Patient 3 | Patient 4 |
|---|---|---|---|---|
| Age (yrs) | 10 | 13 | 13 | 11 |
| Deletion | Exon 50 | Exons 48-50 | Exons 49-50 | Exon 52 |
| Age at Loss of Ambulation (yrs) | 9 | 11 | 7 | 10 |
| Scoliosis | No | No | Yes | Yes |
| Creatine Kinase Levels (U/I)[1] | 5823 | 2531 | 717 | 4711 |
| Steroid treatment | Yes | Yes | Never | Until January 2006 |
| Strength TA muscle (MRC scale) | 4 | 2 | 3 | 4 |
| MRI status TA muscle | Moderate[2] | Moderate[2] | Moderate[2] | Moderate[2] |
| % Revertant fibers | N.D. | <1% | N.D. |  |

[1]normal level: <200 U/I
[2]less than 50% fat infiltration and/or fibrosis [Mercuri et al., 2005]

REFERENCES

1. Aartsma-Rus A, Janson A A, Kaman W E, et al. Therapeutic antisense-induced exon skipping in cultured muscle cells from six different DMD patients. Hum Mol Genet. 2003; 12(8):907-14.
2. Aartsma-Rus A, Janson A A, Kaman W E, et al. Antisense-induced multiexon skipping for Duchenne muscular dystrophy makes more sense. Am J Hum Genet. 2004; 74(1): 83-92.
3. Alter J, Lou F, Rabinowitz A, et al. Systemic delivery of morpholino oligonucleotide restores dystrophin expression bodywide and improves dystrophic pathology. Nat Med 2006; 12(2):175-7.
4. Goyenvalle A, Vulin A, Fougerousse F, et al. Rescue of dystrophic muscle through U7 snRNA-mediated exon skipping. Science 2004; 306(5702):1796-9.

5. Lu Q L, Mann C J, Lou F, et al. Functional amounts of dystrophin produced by skipping the mutated exon in the mdx dystrophic mouse. Nat Med 2003; 6:6.
6. Lu Q L, Rabinowitz A, Chen Y C, et al. Systemic delivery of antisense oligoribonucleotide restores dystrophin expression in body-wide skeletal muscles. Proc Natl Acad Sci USA 2005; 102(1):198-203.
7. McClorey G, Fall A M, Moulton H M, et al. Induced dystrophin exon skipping in human muscle explants. Neuromuscul Disord 2006; 16(9-10):583-90.
8. McClorey G, Moulton H M, Iversen P L, et al. Antisense oligonucleotide-induced exon skipping restores dystrophin expression in vitro in a canine model of DMD. Gene Ther 2006; 13(19):1373-81.
9. Pramono Z A, Takeshima Y, Alimsardjono H, Ishii A, Takeda S, Matsuo M. Induction of exon skipping of the dystrophin transcript in lymphoblastoid cells by transfecting an antisense oligodeoxynucleotide complementary to an exon recognition sequence. Biochem Biophys Res Commun 1996; 226(2):445-9.
10. Takeshima Y, Yagi M, Wada H, et al. Intravenous infusion of an antisense oligonucleotide results in exon skipping in muscle dystrophin mRNA of Duchenne muscular dystrophy. Pediatr Res 2006; 59(5):690-4.
11. van Deutekom J C, Bremmer-Bout M, Janson A A, et al. Antisense-induced exon skipping restores dystrophin expression in DMD patient derived muscle cells. Hum Mol Genet. 2001; 10(15):1547-54.
12. Aartsma-Rus A, Bremmer-Bout M, Janson A, den Dunnen J, van Ommen G, van Deutekom J. Targeted exon skipping as a potential gene correction therapy for Duchenne muscular dystrophy. Neuromuscul Disord 2002; 12 Suppl:S71-S77.
13. Aartsma-Rus A, De Winter C L, Janson A A, et al. Functional analysis of 114 exon-internal AONs for targeted DMD exon skipping: indication for steric hindrance of SR protein binding sites. Oligonucleotides 2005; 15(4):284-97.
14. Aartsma-Rus A, Janson A A, Heemskerk J A, CL de Winter, G J Van Ommen, J C Van Deutekom. Therapeutic Modulation of DMD Splicing by Blocking Exonic Splicing Enhancer Sites with Antisense Oligonucleotides. Annals of the New York Academy of Sciences 2006; 1082: 74-6.
15. Aartsma-Rus A, Kaman W E, Weij R, den Dunnen J T, van Ommen G J, van Deutekom J C. Exploring the frontiers of therapeutic exon skipping for Duchenne muscular dystrophy by double targeting within one or multiple exons. Mol Ther 2006; 14(3):401-7.
16. Welch E M, Barton E R, Zhuo J, et al. PTC124 targets genetic disorders caused by nonsense mutations. Nature 2007; 447(7140):87-91.
17. Hirawat S, Welch E M, Elfring G L, et al. Safety, tolerability, and pharmacokinetics of PTC124, a nonaminoglycoside nonsense mutation suppressor, following single- and multiple-dose administration to healthy male and female adult volunteers. Journal of clinical pharmacology 2007; 47(4):430-44.
18. Wang B, Li J, Xiao X. Adeno-associated virus vector carrying human minidystrophin genes effectively ameliorates muscular dystrophy in mdx mouse model. Proc Natl Acad Sci USA 2000; 97(25):13714-9.
19. Fabb S A, Wells D J, Serpente P, Dickson G. Adeno-associated virus vector gene transfer and sarcolemmal expression of a 144 kDa micro-dystrophin effectively restores the dystrophin-associated protein complex and inhibits myofibre degeneration in nude/mdx mice. Hum Mol Genet. 2002; 11(7):733-41.
20. Wang Z, Kuhr C S, Allen J M, et al. Sustained AAV-mediated dystrophin expression in a canine model of Duchenne muscular dystrophy with a brief course of immunosuppression. Mol Ther 2007; 15(6):1160-6.
21. Manzur A Y, Kuntzer T, Pike M, Swan A. Glucocorticoid corticosteroids for Duchenne muscular dystrophy. Cochrane Database Syst Rev 2004; 2.
22. Duboc D, Meune C, Pierre B, et al. Perindopril preventive treatment on mortality in Duchenne muscular dystrophy: 10 years' follow-up. American heart journal 2007; 154(3): 596-602.
23. Cohn R D, van Erp C, Habashi J P, et al. Angiotensin II type 1 receptor blockade attenuates TGF-beta-induced failure of muscle regeneration in multiple myopathic states. Nat Med 2007; 13(2):204-10.
24. Grounds M D, Torrisi J. Anti-TNFalpha (Remicade) therapy protects dystrophic skeletal muscle from necrosis. Faseb J 2004; 18(6):676-82.
25. Hodgetts S, Radley H, Davies M, Grounds M D. Reduced necrosis of dystrophic muscle by depletion of host neutrophils, or blocking TNFalpha function with Etanercept in mdx mice. Neuromuscul Disord 2006; 16(9-10):591-602.
26. Pierno S, Nico B, Burdi R, et al. Role of tumour necrosis factor alpha, but not of cyclo-oxygenase-2-derived eicosanoids, on functional and morphological indices of dystrophic progression in mdx mice: a pharmacological approach. Neuropathology and applied neurobiology 2007; 33(3):344-59.
27. Musaro A, McCullagh K, Paul A, et al. Localized Igf-1 transgene expression sustains hypertrophy and regeneration in senescent skeletal muscle. Nat Genet. 2001; 27(2): 195-200.
28. Barton E R, Morris L, Musaro A, Rosenthal N, Sweeney H L. Muscle-specific expression of insulin-like growth factor I counters muscle decline in mdx mice. J Cell Biol 2002; 157(1):137-48.
29. Disatnik M H, Dhawan J, Yu Y, et al. Evidence of oxidative stress in mdx mouse muscle: studies of the pre-necrotic state. J Neurol Sci 1998; 161(1):77-84.
30. Nelson S K, Bose S K, Grunwald G K, Myhill P, McCord J M. The induction of human superoxide dismutase and catalase in vivo: a fundamentally new approach to antioxidant therapy. Free radical biology & medicine 2006; 40(2): 341-7.
31. Hart P E, Lodi R, Rajagopalan B, et al. Antioxidant treatment of patients with Friedreich ataxia: four-year follow-up. Archives of neurology 2005; 62(4):621-6.
32. Rolland J F, De Luca A, Burdi R, Andreetta F, Confalonieri P, Conte Camerino D. Overactivity of exercise-sensitive cation channels and their impaired modulation by IGF-1 in mdx native muscle fibers: beneficial effect of pentoxifylline. Neurobiol Dis 2006; 24(3):466-74.
33. Whitehead N P, Streamer M, Lusambili L I, Sachs F, Allen D G. Streptomycin reduces stretch-induced membrane permeability in muscles from mdx mice. Neuromuscul Disord 2006; 16(12):845-54.
34. Badalamente M A, Stracher A. Delay of muscle degeneration and necrosis in mdx mice by calpain inhibition. Muscle Nerve 2000; 23(1):106-11.
35. Burdi R, Didonna M P, Pignol B, et al. First evaluation of the potential effectiveness in muscular dystrophy of a novel chimeric compound, BN 82270, acting as calpain-inhibitor and anti-oxidant. Neuromuscul Disord 2006; 16(4):237-48.

36. Bonuccelli G, Sotgia F, Schubert W, et al. Proteasome inhibitor (MG-132) treatment of mdx mice rescues the expression and membrane localization of dystrophin and dystrophin-associated proteins. Am J Pathol 2003; 163(4): 1663-75.
37. Voisin V, Sebrie C, Matecki S, et al. L-arginine improves dystrophic phenotype in mdx mice. Neurobiol Dis 2005; 20(1):123-30.
38. Soret J, Bakkour N, Maire S, et al. Selective modification of alternative splicing by indole derivatives that target serine-arginine-rich protein splicing factors. Proc Natl Acad Sci USA 2005; 102(24):8764-9.
39. Mann C J, Honeyman K, McClorey G, Fletcher S, Wilton S D. Improved antisense oligonucleotide induced exon skipping in the mdx mouse model of muscular dystrophy. J Gene Med 2002; 4(6):644-54.
40. Graham I R, Hill V J, Manoharan M, Inamati G B, Dickson G. Towards a therapeutic inhibition of dystrophin exon 23 splicing in mdx mouse muscle induced by antisense oligoribonucleotides (splicomers): target sequence optimisation using oligonucleotide arrays. J Gene Med 2004; 6(10):1149-58.
41. Mathews D H, Sabina J, Zuker M, Turner D H. Expanded sequence dependence of thermodynamic parameters improves prediction of RNA secondary structure. J Mol Biol 1999; 288(5):911-40.
42. Cartegni L, Chew S L, Kramer A R. Listening to silence and understanding nonsense: exonic mutations that affect splicing. Nat Rev Genet. 2002; 3(4):285-98.
43. Cartegni L, Wang J, Zhu Z, Zhang M Q, Krainer A R. ESEfinder: A web resource to identify exonic splicing enhancers. Nucleic Acids Res 2003; 31(13):3568-71.
44. Braasch D A, Corey D R. Locked nucleic acid (LNA): fine-tuning the recognition of DNA and RNA. Chem Biol 2001; 8(1):1-7.
45. Braasch D A, Corey D R. Novel antisense and peptide nucleic acid strategies for controlling gene expression. Biochemistry 2002; 41(14):4503-10.
46. Elayadi A N, Corey D R. Application of PNA and LNA oligomers to chemotherapy. Curr Opin Investig Drugs 2001; 2(4):558-61.
47. Larsen H J, Bentin T, Nielsen P E. Antisense properties of peptide nucleic acid. Biochim Biophys Acta 1999; 1489 (1):159-66.
48. Summerton J. Morpholino antisense oligomers: the case for an RNase H-independent structural type. Biochim Biophys Acta 1999; 1489(1):141-58.
49. Summerton J, Weller D. Morpholino antisense oligomers: design, preparation, and properties. Antisense Nucleic Acid Drug Dev 1997; 7(3):187-95.
50. Wahlestedt C, Salmi P, Good L, et al. Potent and nontoxic antisense oligonucleotides containing locked nucleic acids. Proc Natl Acad Sci USA 2000; 97(10):5633-8.
51. De Angelis F G, Sthandier O, Berarducci B, et al. Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 2002; 99(14):9456-61.
52. Denti M A, Rosa A, D'Antona G, et al. Chimeric adeno-associated virus/antisense U1 small nuclear RNA effectively rescues dystrophin synthesis and muscle function by local treatment of mdx mice. Hum Gene Ther 2006; 17(5): 565-74.
53. Gorman L, Suter D, Emerick V, Schumperli D, Kole R. Stable alteration of pre-mRNA splicing patterns by modified U7 small nuclear RNAs. Proc Natl Acad Sci USA 1998; 95(9):4929-34.
54. Suter D, Tomasini R, Reber U, Gorman L, Kole R, Schumperli D. Double-target antisense U7 snRNAs promote efficient skipping of an aberrant exon in three human beta-thalassemic mutations. Hum Mol Genet. 1999; 8(13): 2415-23.
55. Wagner K R, Hamed S, Hadley D W, et al. Gentamicin treatment of Duchenne and Becker muscular dystrophy due to nonsense mutations. Ann Neurol 2001; 49(6):706-11.
56. Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144.
57. Hodgetts S., et al, (2006), Neuromuscular Disorders, 16: 591-602.
58. Manzur A Y et al, (2008), Glucocorticoid corticosteroids for Duchenne muscular dystrophy (review), Wiley publishers, The Cochrane collaboration.
59. Van Deutekom J C et al, (2007) Antisense Oligonucleotide PRO051 Restores Local Dystrophin in DMD Patients. N Engl J. Med., 357(26): 2677-86.
60. Yuan H, Takeuchi E, Taylor G A, McLaughlin M, Brown D, Salant D J. Nephrin dissociates from actin, and its expression is reduced in early experimental membranous nephropathy. J Am Soc Nephrol 2002; 13:946-56.
61. Koop K, Bakker R C, Eikmans M, et al. Differentiation between chronic rejection and chronic cyclosporine toxicity by analysis of renal cortical mRNA. Kindney Int 2004; 66:2038-46.
62. Mercuri E, Bushby K, Ricci e., et al. Muscle MRI findings in patients with limb girdle muscular dystrophy with calpain 3 deficiency (LGMD2A) and early contractures. Neuromuscul Disord 2005; 15:164-71.
63. Dorph C, Nennesmo I, Lundberg I E. Percutaneous conchotome muscle biopsy: a useful diagnostic and assessment tool. J Rheumatol 2001; 28:1591-9.
64. Havenga M J, Lemckert A A, Ophorst O J, et al. Exploiting the natural diversity in adenovirus tropism for therapy and prevention of disease. J Virol 2002; 76:4612-20.
65. Roest P A, van der Tuijn A C, Ginjaar H B, et al. Application of in vitro Myo-differentation of non-muscle cells to enhance gene expression and facilitate analysis of muscle proteins. Neuromuscul Disord 1996; 6:195-202.
66. John J. Grading of muscular power: comparison of MRC and analogue scales by physiotherapists. Int J Rehabil Res 1984; 7:173-81.
67. Roest P A, Roberts R G, van der Tuijn A C, Heikoop J C, van Ommen G J, den Dunnen J T. Protein truncation test (PTT) to rapidly screen the DMD gene for translation terminating mutations. Neuromuscul Disord 1993; 3:391-4.
68. Cullen M J, Walsh J, Roberds S L, Campbell K P. Ultrastructural localization of adhalin, alpha-dystroglycan and merosin in normal and dystrophic muscle. Neuropathol Appl Neurobiol 1996; 22:30-7.

The invention claimed is:

1. A composition comprising:
a first compound that increases the level of a functional dystrophin protein produced in a muscle cell of a Duchenne Muscular Dystrophy (DMD) or Becker Muscular Dystrophy (BMD) individual,
wherein said first compound is an antisense oligonucleotide that induces skipping of exon 51 of human dystrophin pre-mRNA of said individual;
and a second compound comprising a steroid;
wherein, upon administration to a DMD or BMD patient, the composition increases the ratio of said dystrophin to laminin-α2 in muscle tissue of said patient as compared to the ratio of said dystrophin to laminin-α2 in muscle tissue of a patient administered with said first compound and not said second compound; and
wherein said antisense oligonucleotide is 100% complementary to a portion of exon 51 that is 13 to 50 nucleotides in length and wherein said oligonucleotide comprises a non naturally-occurring modification.

2. The composition of claim 1, wherein said antisense oligonucleotide is 100% complementary to a portion of exon 51 that is 14 to 25 nucleotides in length.

3. The composition of claim 1, wherein said antisense oligonucleotide is 100% complementary to a portion of exon 51 that is 20 to 25 nucleotides in length.

4. The composition of claim 1, wherein said oligonucleotide comprises one or more ribonucleotides, and wherein a said ribonucleotide contains a modification.

5. The composition of claim 4, wherein said modification is a 2'-O-methyl modified ribose.

6. The composition of claim 1, wherein said modification is selected from the group consisting of at least one of a peptide nucleic acid, a locked nucleic acid, and morpholino phosphorodiamidate.

7. A method for alleviating one or more symptom(s) of Duchenne Muscular Dystrophy or Becker Muscular Dystrophy in an individual, the method comprising administering to a DMD or BMD patient:
a first compound that increases the level of a functional dystrophin protein produced in a muscle cell of said individual in said individual,
wherein said first compound is an antisense oligonucleotide that induces skipping of exon 51 of dystrophin pre-mRNA of said individual, and
a second compound, comprising a steroid;
wherein, upon administration to a DMD or BMD patient, the composition increases the ratio of said dystrophin to laminin-α2 in muscle tissue of said patient as compared to the ratio of said dystrophin to laminin-α2 in muscle tissue of a patient administered with said first compound and not said second compound; and
wherein said antisense oligonucleotide is 100% complementary to a portion of exon 51 that is 13 to 50 nucleotides in length and wherein said oligonucleotide comprises a non naturally-occurring modification.

8. The method of claim 7, wherein said oligonucleotide comprises one or more ribonucleotides, and wherein a said ribonucleotide contains a modification.

9. The method of claim 8, wherein said modification is selected from the group consisting of a 2'-O-methyl modified ribose.

10. The method of claim 7, wherein said modification is selected from the group consisting of at least one of a peptide nucleic acid, a locked nucleic acid, and morpholino phosphorodiamidate.

11. A method for increasing the production of a functional dystrophin protein in a cell, said cell comprising pre-mRNA of a dystrophin gene encoding an aberrant dystrophin protein comprising:
providing said cell with a first compound for inhibiting inclusion of exon 51 into mRNA produced from splicing of said dystrophin pre-mRNA, wherein said first compound is an antisense oligonucleotide that induces the skipping of exon 51 of the human dystrophin pre-mRNA, and providing said cell with a second compound comprising a steroid,
said method further comprising allowing translation of mRNA produced from splicing of said pre-mRNA;
wherein, upon administration to a DMD or BMD patient, the composition increases the ratio of said dystrophin to laminin-α2 in muscle tissue of said patient as compared to the ratio of said dystrophin to laminin-α2 in muscle tissue of a patient administered with said first compound and not said second compound; and
wherein said antisense oligonucleotide is 100% complementary to a portion of exon 51 that is 13 to 50 nucleotides in length and wherein said oligonucleotide comprises a non naturally-occurring modification.

12. A pharmaceutical preparation comprising:
said first compound according to claim 1,
said second compound according to claim 1, comprising a steroid,
and a pharmaceutically acceptable carrier, adjuvant, diluent and/or excipient.

13. A kit comprising:
said first compound according to claim 1,
and said second compound according to claim 1.

14. The kit of claim 13, further comprising a pharmaceutically acceptable carrier, adjuvant, diluent and/or excipient.

15. The kit of claim 13, further comprising packaging means thereof.

16. The composition according to claim 1, wherein the oligonucleotide comprises a phosphorothioate internucleotide linkage, a 2'-O-methyl ribose and/or a LNA.

17. The kit according to claim 13, wherein the oligonucleotide comprises a phosphorothioate internucleotide linkage, a 2'-O-methyl ribose and/or a LNA.

18. A pharmaceutical composition comprising the composition of claim 1 and a pharmaceutically acceptable carrier, adjuvant, diluent, and/or excipient.

19. The method of claim 7 wherein said steroid is a glucocorticosteroid.

20. The method of claim 19 wherein said glucocorticosteroid is selected from a group consisting of prednisone, dexamethasone, prednizolone and deflazacort.

21. The method of claim 20 wherein said prednisone is present at a dosage of 0.5-1.0 mg/kg.

22. The method of claim 20 wherein said deflazacort is present at a dosage of 0.4-1.4 mg/kg.

\* \* \* \* \*

SEQUENCE LISTING

<160> NUMBER OF SEQ ID NOS: 314

<210> SEQ ID NO 1
<211> LENGTH: 3685
<212> TYPE: PRT
<213> ORGANISM: Homo sapiens

<400> SEQUENCE: 1

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365
```

-continued

```
Ser Asn Asp Val Glu Val Val Lys Asp Gln Phe His Thr His Glu Gly
    370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
                420                 425                 430
Cys Leu Arg Val Ala Ser Met Glu Lys Gln Ser Asn Leu His Arg Val
            435                 440                 445
Leu Met Asp Leu Gln Asn Gln Lys Leu Lys Glu Leu Asn Asp Trp Leu
450                 455                 460
Thr Lys Thr Glu Glu Arg Thr Arg Lys Met Glu Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
                500                 505                 510
Met Val Val Val Asp Glu Ser Ser Gly Asp His Ala Thr Ala Ala
            515                 520                 525
Leu Glu Glu Gln Leu Lys Val Leu Gly Asp Arg Trp Ala Asn Ile Cys
530                 535                 540
Arg Trp Thr Glu Asp Arg Trp Val Leu Leu Gln Asp Ile Leu Leu Lys
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
                580                 585                 590
Gln Asn Glu Met Leu Ser Ser Leu Gln Lys Leu Ala Val Leu Lys Ala
            595                 600                 605
Asp Leu Glu Lys Lys Lys Gln Ser Met Gly Lys Leu Tyr Ser Leu Lys
            610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
Lys Leu Glu Lys Ser Thr Ala Gln Ile Ser Gln Ala Val Thr Thr Thr
                660                 665                 670
Gln Pro Ser Leu Thr Gln Thr Thr Val Met Glu Thr Val Thr Thr Val
            675                 680                 685
Thr Thr Arg Glu Gln Ile Leu Val Lys His Ala Gln Glu Glu Leu Pro
690                 695                 700
Pro Pro Pro Pro Gln Lys Lys Arg Gln Ile Thr Val Asp Ser Glu Ile
705                 710                 715                 720
Arg Lys Arg Leu Asp Val Asp Ile Thr Glu Leu His Ser Trp Ile Thr
                725                 730                 735
Arg Ser Glu Ala Val Leu Gln Ser Pro Glu Phe Ala Ile Phe Arg Lys
                740                 745                 750
Glu Gly Asn Phe Ser Asp Leu Lys Glu Lys Val Asn Ala Ile Glu Arg
            755                 760                 765
Glu Lys Ala Glu Lys Phe Arg Lys Leu Gln Asp Ala Ser Arg Ser Ala
            770                 775                 780
Gln Ala Leu Val Glu Gln Met Val Asn Glu Gly Val Asn Ala Asp Ser
```

```
            785                 790                 795                 800
Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
                820                 825                 830

Ile Ala Phe Tyr Asn Gln Leu Gln Gln Leu Glu Gln Met Thr Thr Thr
                835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
                900                 905                 910

Ala Phe Thr Asn His Phe Lys Gln Val Phe Ser Asp Val Gln Ala Arg
                915                 920                 925

Glu Lys Glu Leu Gln Thr Ile Phe Asp Thr Leu Pro Pro Met Arg Tyr
930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
                980                 985                 990

Gln Ser Gly Leu Tyr Tyr Leu Ser Thr Thr Val Lys Glu Met Ser Lys
                995                 1000                1005

Lys Ala Pro Ser Glu Ile Ser Arg Lys Tyr Gln Ser Glu Phe Glu
        1010                1015                1020

Glu Ile Glu Gly Arg Trp Lys Lys Leu Ser Ser Gln Leu Val Glu
        1025                1030                1035

His Cys Gln Lys Leu Glu Glu Gln Met Asn Lys Leu Arg Lys Ile
        1040                1045                1050

Gln Asn His Ile Gln Thr Leu Lys Lys Trp Met Ala Glu Val Asp
        1055                1060                1065

Val Phe Leu Lys Glu Glu Trp Pro Ala Leu Gly Asp Ser Glu Ile
        1070                1075                1080

Leu Lys Lys Gln Leu Lys Gln Cys Arg Leu Leu Val Ser Asp Ile
        1085                1090                1095

Gln Thr Ile Gln Pro Ser Leu Asn Ser Val Asn Glu Gly Gly Gln
        1100                1105                1110

Lys Ile Lys Asn Glu Ala Glu Pro Glu Phe Ala Ser Arg Leu Glu
        1115                1120                1125

Thr Glu Leu Lys Glu Leu Asn Thr Gln Trp Asp His Met Cys Gln
        1130                1135                1140

Gln Val Tyr Ala Arg Lys Glu Ala Leu Lys Gly Gly Leu Glu Lys
        1145                1150                1155

Thr Val Ser Leu Gln Lys Asp Leu Ser Glu Met His Glu Trp Met
        1160                1165                1170

Thr Gln Ala Glu Glu Glu Tyr Leu Glu Arg Asp Phe Glu Tyr Lys
        1175                1180                1185

Thr Pro Asp Glu Leu Gln Lys Ala Val Glu Glu Met Lys Arg Ala
        1190                1195                1200
```

-continued

```
Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Gln Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
1490                1495                1500

His Cys Val Asn Leu Tyr Lys Ser Leu Ser Glu Val Lys Ser Glu
1505                1510                1515

Val Glu Met Val Ile Lys Thr Gly Arg Gln Ile Val Gln Lys Lys
1520                1525                1530

Gln Thr Glu Asn Pro Lys Glu Leu Asp Glu Arg Val Thr Ala Leu
1535                1540                1545

Lys Leu His Tyr Asn Glu Leu Gly Ala Lys Val Thr Glu Arg Lys
1550                1555                1560

Gln Gln Leu Glu Lys Cys Leu Lys Leu Ser Arg Lys Met Arg Lys
1565                1570                1575

Glu Met Asn Val Leu Thr Glu Trp Leu Ala Ala Thr Asp Met Glu
1580                1585                1590
```

```
Leu Thr Lys Arg Ser Ala Val Glu Gly Met Pro Ser Asn Leu Asp
1595                1600                1605

Ser Glu Val Ala Trp Gly Lys Ala Thr Gln Lys Glu Ile Glu Lys
1610                1615                1620

Gln Lys Val His Leu Lys Ser Ile Thr Glu Val Gly Glu Ala Leu
1625                1630                1635

Lys Thr Val Leu Gly Lys Lys Glu Thr Leu Val Glu Asp Lys Leu
1640                1645                1650

Ser Leu Leu Asn Ser Asn Trp Ile Ala Val Thr Ser Arg Ala Glu
1655                1660                1665

Glu Trp Leu Asn Leu Leu Glu Tyr Gln Lys His Met Glu Thr
1670                1675                1680

Phe Asp Gln Asn Val Asp His Ile Thr Lys Trp Ile Ile Gln Ala
1685                1690                1695

Asp Thr Leu Leu Asp Glu Ser Glu Lys Lys Lys Pro Gln Gln Lys
1700                1705                1710

Glu Asp Val Leu Lys Arg Leu Lys Ala Glu Leu Asn Asp Ile Arg
1715                1720                1725

Pro Lys Val Asp Ser Thr Arg Asp Gln Ala Ala Asn Leu Met Ala
1730                1735                1740

Asn Arg Gly Asp His Cys Arg Lys Leu Val Glu Pro Gln Ile Ser
1745                1750                1755

Glu Leu Asn His Arg Phe Ala Ala Ile Ser His Arg Ile Lys Thr
1760                1765                1770

Gly Lys Ala Ser Ile Pro Leu Lys Glu Leu Glu Gln Phe Asn Ser
1775                1780                1785

Asp Ile Gln Lys Leu Leu Glu Pro Leu Glu Ala Glu Ile Gln Gln
1790                1795                1800

Gly Val Asn Leu Lys Glu Glu Asp Phe Asn Lys Asp Met Asn Glu
1805                1810                1815

Asp Asn Glu Gly Thr Val Lys Glu Leu Leu Gln Arg Gly Asp Asn
1820                1825                1830

Leu Gln Gln Arg Ile Thr Asp Glu Arg Lys Arg Glu Glu Ile Lys
1835                1840                1845

Ile Lys Gln Gln Leu Leu Gln Thr Lys His Asn Ala Leu Lys Asp
1850                1855                1860

Leu Arg Ser Gln Arg Arg Lys Lys Ala Leu Glu Ile Ser His Gln
1865                1870                1875

Trp Tyr Gln Tyr Lys Arg Gln Ala Asp Asp Leu Leu Lys Cys Leu
1880                1885                1890

Asp Asp Ile Glu Lys Lys Leu Ala Ser Leu Pro Glu Pro Arg Asp
1895                1900                1905

Glu Arg Lys Ile Lys Glu Ile Asp Arg Glu Leu Gln Lys Lys Lys
1910                1915                1920

Glu Glu Leu Asn Ala Val Arg Arg Gln Ala Glu Gly Leu Ser Glu
1925                1930                1935

Asp Gly Ala Ala Met Ala Val Glu Pro Thr Gln Ile Gln Leu Ser
1940                1945                1950

Lys Arg Trp Arg Glu Ile Glu Ser Lys Phe Ala Gln Phe Arg Arg
1955                1960                1965

Leu Asn Phe Ala Gln Ile His Thr Val Arg Glu Glu Thr Met Met
1970                1975                1980

Val Met Thr Glu Asp Met Pro Leu Glu Ile Ser Tyr Val Pro Ser
```

```
            1985                1990                1995
Thr Tyr Leu Thr Glu Ile Thr His Val Ser Gln Ala Leu Leu Glu
        2000                2005                2010

Val Glu Gln Leu Leu Asn Ala Pro Asp Leu Cys Ala Lys Asp Phe
        2015                2020                2025

Glu Asp Leu Phe Lys Gln Glu Glu Ser Leu Lys Asn Ile Lys Asp
        2030                2035                2040

Ser Leu Gln Gln Ser Ser Gly Arg Ile Asp Ile Ile His Ser Lys
        2045                2050                2055

Lys Thr Ala Ala Leu Gln Ser Ala Thr Pro Val Glu Arg Val Lys
        2060                2065                2070

Leu Gln Glu Ala Leu Ser Gln Leu Asp Phe Gln Trp Glu Lys Val
        2075                2080                2085

Asn Lys Met Tyr Lys Asp Arg Gln Gly Arg Phe Asp Arg Ser Val
        2090                2095                2100

Glu Lys Trp Arg Arg Phe His Tyr Asp Ile Lys Ile Phe Asn Gln
        2105                2110                2115

Trp Leu Thr Glu Ala Glu Gln Phe Leu Arg Lys Thr Gln Ile Pro
        2120                2125                2130

Glu Asn Trp Glu His Ala Lys Tyr Lys Trp Tyr Leu Lys Glu Leu
        2135                2140                2145

Gln Asp Gly Ile Gly Gln Arg Gln Thr Val Val Arg Thr Leu Asn
        2150                2155                2160

Ala Thr Gly Glu Glu Ile Ile Gln Gln Ser Ser Lys Thr Asp Ala
        2165                2170                2175

Ser Ile Leu Gln Glu Lys Leu Gly Ser Leu Asn Leu Arg Trp Gln
        2180                2185                2190

Glu Val Cys Lys Gln Leu Ser Asp Arg Lys Lys Arg Leu Glu Glu
        2195                2200                2205

Gln Lys Asn Ile Leu Ser Glu Phe Gln Arg Asp Leu Asn Glu Phe
        2210                2215                2220

Val Leu Trp Leu Glu Glu Ala Asp Asn Ile Ala Ser Ile Pro Leu
        2225                2230                2235

Glu Pro Gly Lys Glu Gln Gln Leu Lys Glu Lys Leu Glu Gln Val
        2240                2245                2250

Lys Leu Leu Val Glu Glu Leu Pro Leu Arg Gln Gly Ile Leu Lys
        2255                2260                2265

Gln Leu Asn Glu Thr Gly Gly Pro Val Leu Val Ser Ala Pro Ile
        2270                2275                2280

Ser Pro Glu Glu Gln Asp Lys Leu Glu Asn Lys Leu Lys Gln Thr
        2285                2290                2295

Asn Leu Gln Trp Ile Lys Val Ser Arg Ala Leu Pro Glu Lys Gln
        2300                2305                2310

Gly Glu Ile Glu Ala Gln Ile Lys Asp Leu Gly Gln Leu Glu Lys
        2315                2320                2325

Lys Leu Glu Asp Leu Glu Glu Gln Leu Asn His Leu Leu Leu Trp
        2330                2335                2340

Leu Ser Pro Ile Arg Asn Gln Leu Glu Ile Tyr Asn Gln Pro Asn
        2345                2350                2355

Gln Glu Gly Pro Phe Asp Val Gln Glu Thr Glu Ile Ala Val Gln
        2360                2365                2370

Ala Lys Gln Pro Asp Val Glu Glu Ile Leu Ser Lys Gly Gln His
        2375                2380                2385
```

```
Leu Tyr Lys Glu Lys Pro Ala Thr Gln Pro Val Lys Arg Lys Leu
    2390            2395                2400

Glu Asp Leu Ser Ser Glu Trp Lys Ala Val Asn Arg Leu Leu Gln
    2405            2410                2415

Glu Leu Arg Ala Lys Gln Pro Asp Leu Ala Pro Gly Leu Thr Thr
    2420            2425                2430

Ile Gly Ala Ser Pro Thr Gln Thr Val Thr Leu Val Thr Gln Pro
    2435            2440                2445

Val Val Thr Lys Glu Thr Ala Ile Ser Lys Leu Glu Met Pro Ser
    2450            2455                2460

Ser Leu Met Leu Glu Val Pro Ala Leu Ala Asp Phe Asn Arg Ala
    2465            2470                2475

Trp Thr Glu Leu Thr Asp Trp Leu Ser Leu Leu Asp Gln Val Ile
    2480            2485                2490

Lys Ser Gln Arg Val Met Val Gly Asp Leu Glu Asp Ile Asn Glu
    2495            2500                2505

Met Ile Ile Lys Gln Lys Ala Thr Met Gln Asp Leu Glu Gln Arg
    2510            2515                2520

Arg Pro Gln Leu Glu Glu Leu Ile Thr Ala Ala Gln Asn Leu Lys
    2525            2530                2535

Asn Lys Thr Ser Asn Gln Glu Ala Arg Thr Ile Ile Thr Asp Arg
    2540            2545                2550

Ile Glu Arg Ile Gln Asn Gln Trp Asp Glu Val Gln Glu His Leu
    2555            2560                2565

Gln Asn Arg Arg Gln Gln Leu Asn Glu Met Leu Lys Asp Ser Thr
    2570            2575                2580

Gln Trp Leu Glu Ala Lys Glu Glu Ala Glu Gln Val Leu Gly Gln
    2585            2590                2595

Ala Arg Ala Lys Leu Glu Ser Trp Lys Glu Gly Pro Tyr Thr Val
    2600            2605                2610

Asp Ala Ile Gln Lys Lys Ile Thr Glu Thr Lys Gln Leu Ala Lys
    2615            2620                2625

Asp Leu Arg Gln Trp Gln Thr Asn Val Asp Val Ala Asn Asp Leu
    2630            2635                2640

Ala Leu Lys Leu Leu Arg Asp Tyr Ser Ala Asp Asp Thr Arg Lys
    2645            2650                2655

Val His Met Ile Thr Glu Asn Ile Asn Ala Ser Trp Arg Ser Ile
    2660            2665                2670

His Lys Arg Val Ser Glu Arg Glu Ala Ala Leu Glu Glu Thr His
    2675            2680                2685

Arg Leu Leu Gln Gln Phe Pro Leu Asp Leu Glu Lys Phe Leu Ala
    2690            2695                2700

Trp Leu Thr Glu Ala Glu Thr Thr Ala Asn Val Leu Gln Asp Ala
    2705            2710                2715

Thr Arg Lys Glu Arg Leu Leu Glu Asp Ser Lys Gly Val Lys Glu
    2720            2725                2730

Leu Met Lys Gln Trp Gln Asp Leu Gln Gly Glu Ile Glu Ala His
    2735            2740                2745

Thr Asp Val Tyr His Asn Leu Asp Glu Asn Ser Gln Lys Ile Leu
    2750            2755                2760

Arg Ser Leu Glu Gly Ser Asp Asp Ala Val Leu Leu Gln Arg Arg
    2765            2770                2775
```

```
Leu Asp Asn Met Asn Phe Lys Trp Ser Glu Leu Arg Lys Lys Ser
2780                2785                2790

Leu Asn Ile Arg Ser His Leu Glu Ala Ser Ser Asp Gln Trp Lys
2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
2825                2830                2835

Pro Ala Val Gln Lys Gln Asn Asp Val His Arg Ala Phe Lys Arg
2840                2845                2850

Glu Leu Lys Thr Lys Glu Pro Val Ile Met Ser Thr Leu Glu Thr
2855                2860                2865

Val Arg Ile Phe Leu Thr Glu Gln Pro Leu Glu Gly Leu Glu Lys
2870                2875                2880

Leu Tyr Gln Glu Pro Arg Glu Leu Pro Pro Glu Glu Arg Ala Gln
2885                2890                2895

Asn Val Thr Arg Leu Leu Arg Lys Gln Ala Glu Glu Val Asn Thr
2900                2905                2910

Glu Trp Glu Lys Leu Asn Leu His Ser Ala Asp Trp Gln Arg Lys
2915                2920                2925

Ile Asp Glu Thr Leu Glu Arg Leu Gln Glu Leu Gln Glu Ala Thr
2930                2935                2940

Asp Glu Leu Asp Leu Lys Leu Arg Gln Ala Glu Val Ile Lys Gly
2945                2950                2955

Ser Trp Gln Pro Val Gly Asp Leu Leu Ile Asp Ser Leu Gln Asp
2960                2965                2970

His Leu Glu Lys Val Lys Ala Leu Arg Gly Glu Ile Ala Pro Leu
2975                2980                2985

Lys Glu Asn Val Ser His Val Asn Asp Leu Ala Arg Gln Leu Thr
2990                2995                3000

Thr Leu Gly Ile Gln Leu Ser Pro Tyr Asn Leu Ser Thr Leu Glu
3005                3010                3015

Asp Leu Asn Thr Arg Trp Lys Leu Leu Gln Val Ala Val Glu Asp
3020                3025                3030

Arg Val Arg Gln Leu His Glu Ala His Arg Asp Phe Gly Pro Ala
3035                3040                3045

Ser Gln His Phe Leu Ser Thr Ser Val Gln Gly Pro Trp Glu Arg
3050                3055                3060

Ala Ile Ser Pro Asn Lys Val Pro Tyr Tyr Ile Asn His Glu Thr
3065                3070                3075

Gln Thr Thr Cys Trp Asp His Pro Lys Met Thr Glu Leu Tyr Gln
3080                3085                3090

Ser Leu Ala Asp Leu Asn Asn Val Arg Phe Ser Ala Tyr Arg Thr
3095                3100                3105

Ala Met Lys Leu Arg Arg Leu Gln Lys Ala Leu Cys Leu Asp Leu
3110                3115                3120

Leu Ser Leu Ser Ala Ala Cys Asp Ala Leu Asp Gln His Asn Leu
3125                3130                3135

Lys Gln Asn Asp Gln Pro Met Asp Ile Leu Gln Ile Ile Asn Cys
3140                3145                3150

Leu Thr Thr Ile Tyr Asp Arg Leu Glu Gln Glu His Asn Asn Leu
3155                3160                3165

Val Asn Val Pro Leu Cys Val Asp Met Cys Leu Asn Trp Leu Leu
```

```
                    3170            3175            3180
Asn Val Tyr Asp Thr Gly Arg Thr Gly Arg Ile Arg Val Leu Ser
        3185            3190            3195
Phe Lys Thr Gly Ile Ile Ser Leu Cys Lys Ala His Leu Glu Asp
        3200            3205            3210
Lys Tyr Arg Tyr Leu Phe Lys Gln Val Ala Ser Thr Gly Phe
        3215            3220            3225
Cys Asp Gln Arg Arg Leu Gly Leu Leu Leu His Asp Ser Ile Gln
        3230            3235            3240
Ile Pro Arg Gln Leu Gly Glu Val Ala Ser Phe Gly Gly Ser Asn
        3245            3250            3255
Ile Glu Pro Ser Val Arg Ser Cys Phe Gln Phe Ala Asn Asn Lys
        3260            3265            3270
Pro Glu Ile Glu Ala Ala Leu Phe Leu Asp Trp Met Arg Leu Glu
        3275            3280            3285
Pro Gln Ser Met Val Trp Leu Pro Val Leu His Arg Val Ala Ala
        3290            3295            3300
Ala Glu Thr Ala Lys His Gln Ala Lys Cys Asn Ile Cys Lys Glu
        3305            3310            3315
Cys Pro Ile Ile Gly Phe Arg Tyr Arg Ser Leu Lys His Phe Asn
        3320            3325            3330
Tyr Asp Ile Cys Gln Ser Cys Phe Phe Ser Gly Arg Val Ala Lys
        3335            3340            3345
Gly His Lys Met His Tyr Pro Met Val Glu Tyr Cys Thr Pro Thr
        3350            3355            3360
Thr Ser Gly Glu Asp Val Arg Asp Phe Ala Lys Val Leu Lys Asn
        3365            3370            3375
Lys Phe Arg Thr Lys Arg Tyr Phe Ala Lys His Pro Arg Met Gly
        3380            3385            3390
Tyr Leu Pro Val Gln Thr Val Leu Glu Gly Asp Asn Met Glu Thr
        3395            3400            3405
Pro Val Thr Leu Ile Asn Phe Trp Pro Val Asp Ser Ala Pro Ala
        3410            3415            3420
Ser Ser Pro Gln Leu Ser His Asp Asp Thr His Ser Arg Ile Glu
        3425            3430            3435
His Tyr Ala Ser Arg Leu Ala Glu Met Glu Asn Ser Asn Gly Ser
        3440            3445            3450
Tyr Leu Asn Asp Ser Ile Ser Pro Asn Glu Ser Ile Asp Asp Glu
        3455            3460            3465
His Leu Leu Ile Gln His Tyr Cys Gln Ser Leu Asn Gln Asp Ser
        3470            3475            3480
Pro Leu Ser Gln Pro Arg Ser Pro Ala Gln Ile Leu Ile Ser Leu
        3485            3490            3495
Glu Ser Glu Glu Arg Gly Glu Leu Glu Arg Ile Leu Ala Asp Leu
        3500            3505            3510
Glu Glu Glu Asn Arg Asn Leu Gln Ala Glu Tyr Asp Arg Leu Lys
        3515            3520            3525
Gln Gln His Glu His Lys Gly Leu Ser Pro Leu Pro Ser Pro Pro
        3530            3535            3540
Glu Met Met Pro Thr Ser Pro Gln Ser Pro Arg Asp Ala Glu Leu
        3545            3550            3555
Ile Ala Glu Ala Lys Leu Leu Arg Gln His Lys Gly Arg Leu Glu
        3560            3565            3570
```

```
Ala Arg Met Gln Ile Leu Glu Asp His Asn Lys Gln Leu Glu Ser
    3575                3580                3585

Gln Leu His Arg Leu Arg Gln Leu Leu Glu Gln Pro Gln Ala Glu
    3590                3595                3600

Ala Lys Val Asn Gly Thr Thr Val Ser Ser Pro Ser Thr Ser Leu
    3605                3610                3615

Gln Arg Ser Asp Ser Ser Gln Pro Met Leu Leu Arg Val Val Gly
    3620                3625                3630

Ser Gln Thr Ser Asp Ser Met Gly Glu Glu Asp Leu Leu Ser Pro
    3635                3640                3645

Pro Gln Asp Thr Ser Thr Gly Leu Glu Glu Val Met Glu Gln Leu
    3650                3655                3660

Asn Asn Ser Phe Pro Ser Ser Arg Gly Arg Asn Thr Pro Gly Lys
    3665                3670                3675

Pro Met Arg Glu Asp Thr Met
    3680                3685

<210> SEQ ID NO 2
<211> LENGTH: 153
<212> TYPE: PRT
<213> ORGANISM: Homo sapiens

<400> SEQUENCE: 2

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
            130                 135                 140

Ser Ala Gly Asn Lys Asn Tyr Arg Met
145                 150

<210> SEQ ID NO 3
<211> LENGTH: 20
<212> TYPE: DNA
<213> ORGANISM: Artificial
<220> FEATURE:
<223> OTHER INFORMATION: antisense nucleotide

<400> SEQUENCE: 3
cgaccugagc uuguuguag                                                    20

<210> SEQ ID NO 4
<211> LENGTH: 25
<212> TYPE: DNA
```

<213> ORGANISM: Artificial
<220> FEATURE:
<223> OTHER INFORMATION: antisense nucleotide

<400> SEQUENCE: 4
cgaccugagc uuuguuguag acuau                                    25

<210> SEQ ID NO 5
<211> LENGTH: 23
<212> TYPE: DNA
<213> ORGANISM: Artificial
<220> FEATURE:
<223> OTHER INFORMATION: antisense nucleotide

<400> SEQUENCE: 5
ccugagcuuu guuguagacu auc                                      23

<210> SEQ ID NO 6
<211> LENGTH: 23
<212> TYPE: DNA
<213> ORGANISM: Artificial
<220> FEATURE:
<223> OTHER INFORMATION: antisense nucleotide

<400> SEQUENCE: 6
cguugcacuu ugcaaugcug cug                                      23

<210> SEQ ID NO 7
<211> LENGTH: 19
<212> TYPE: DNA
<213> ORGANISM: Artificial
<220> FEATURE:
<223> OTHER INFORMATION: antisense nucleotide

<400> SEQUENCE: 7
cuguagcuuc acccuuucc                                           19

<210> SEQ ID NO 8
<211> LENGTH: 24
<212> TYPE: DNA
<213> ORGANISM: Artificial
<220> FEATURE:
<223> OTHER INFORMATION: antisense nucleotide

<400> SEQUENCE: 8
gagagagcuu ccuguagcuu cacc                                     24

<210> SEQ ID NO 9
<211> LENGTH: 27
<212> TYPE: DNA
<213> ORGANISM: Artificial
<220> FEATURE:
<223> OTHER INFORMATION: antisense nucleotide

<400> SEQUENCE: 9
guccuuguac auuuuguuaa cuuuuuc                                  27

<210> SEQ ID NO 10
<211> LENGTH: 20
<212> TYPE: DNA
<213> ORGANISM: Artificial
<220> FEATURE:
<223> OTHER INFORMATION: antisense nucleotide

<400> SEQUENCE: 10
ucagcuucug uuagccacug                                          20

<210> SEQ ID NO 11
<211> LENGTH: 20
<212> TYPE: DNA
<213> ORGANISM: Artificial
<220> FEATURE:
<223> OTHER INFORMATION: antisense nucleotide

<400> SEQUENCE: 11
uucagcuucu guuagccacu                                             20

<210> SEQ ID NO 12
<211> LENGTH: 21
<212> TYPE: DNA
<213> ORGANISM: Artificial
<220> FEATURE:
<223> OTHER INFORMATION: antisense nucleotide

<400> SEQUENCE: 12
uucagcuucu guuagccacu g                                           21

<210> SEQ ID NO 13
<211> LENGTH: 21
<212> TYPE: DNA
<213> ORGANISM: Artificial
<220> FEATURE:
<223> OTHER INFORMATION: antisense nucleotide

<400> SEQUENCE: 13
ucagcuucug uuagccacug a                                           21

<210> SEQ ID NO 14
<211> LENGTH: 22
<212> TYPE: DNA
<213> ORGANISM: Artificial
<220> FEATURE:
<223> OTHER INFORMATION: antisense nucleotide

<400> SEQUENCE: 14
uucagcuucu guuagccacu ga                                          22

<210> SEQ ID NO 15
<211> LENGTH: 21
<212> TYPE: DNA
<213> ORGANISM: Artificial
<220> FEATURE:
<223> OTHER INFORMATION: antisense nucleotide

<400> SEQUENCE: 15
ucagcuucug uuagccacug a                                           21

<210> SEQ ID NO 16
<211> LENGTH: 22
<212> TYPE: DNA
<213> ORGANISM: Artificial
<220> FEATURE:
<223> OTHER INFORMATION: antisense nucleotide

<400> SEQUENCE: 16
uucagcuucu guuagccacu ga                                          22

<210> SEQ ID NO 17
<211> LENGTH: 22
<212> TYPE: DNA
<213> ORGANISM: Artificial
<220> FEATURE:

-continued

<223> OTHER INFORMATION: antisense nucleotide

<400> SEQUENCE: 17
ucagcuucug uuagccacug au                                              22

<210> SEQ ID NO 18
<211> LENGTH: 23
<212> TYPE: DNA
<213> ORGANISM: Artificial
<220> FEATURE:
<223> OTHER INFORMATION: antisense nucleotide

<400> SEQUENCE: 18
uucagcuucu guuagccacu gau                                             23

<210> SEQ ID NO 19
<211> LENGTH: 23
<212> TYPE: DNA
<213> ORGANISM: Artificial
<220> FEATURE:
<223> OTHER INFORMATION: antisense nucleotide

<400> SEQUENCE: 19
ucagcuucug uuagccacug auu                                             23

<210> SEQ ID NO 20
<211> LENGTH: 24
<212> TYPE: DNA
<213> ORGANISM: Artificial
<220> FEATURE:
<223> OTHER INFORMATION: antisense nucleotide

<400> SEQUENCE: 20
uucagcuucu guuagccacu gauu                                            24

<210> SEQ ID NO 21
<211> LENGTH: 24
<212> TYPE: DNA
<213> ORGANISM: Artificial
<220> FEATURE:
<223> OTHER INFORMATION: antisense nucleotide

<400> SEQUENCE: 21
ucagcuucug uuagccacug auua                                            24

<210> SEQ ID NO 22
<211> LENGTH: 24
<212> TYPE: DNA
<213> ORGANISM: Artificial
<220> FEATURE:
<223> OTHER INFORMATION: antisense nucleotide

<400> SEQUENCE: 22
uucagcuucu guuagccacu gaua                                            24

<210> SEQ ID NO 23
<211> LENGTH: 25
<212> TYPE: DNA
<213> ORGANISM: Artificial
<220> FEATURE:
<223> OTHER INFORMATION: antisense nucleotide

<400> SEQUENCE: 23
ucagcuucug uuagccacug auuaa                                           25

```
<210> SEQ ID NO 24
<211> LENGTH: 26
<212> TYPE: DNA
<213> ORGANISM: Artificial
<220> FEATURE:
<223> OTHER INFORMATION: antisense nucleotide

<400> SEQUENCE: 24
uucagcuucu guuagccacu gauuaa                                              26

<210> SEQ ID NO 25
<211> LENGTH: 26
<212> TYPE: DNA
<213> ORGANISM: Artificial
<220> FEATURE:
<223> OTHER INFORMATION: antisense nucleotide

<400> SEQUENCE: 25
ucagcuucug uuagccacug auuaaa                                              26

<210> SEQ ID NO 26
<211> LENGTH: 27
<212> TYPE: DNA
<213> ORGANISM: Artificial
<220> FEATURE:
<223> OTHER INFORMATION: antisense nucleotide

<400> SEQUENCE: 26
uucagcuucu guuagccacu gauuaaa                                             27

<210> SEQ ID NO 27
<211> LENGTH: 19
<212> TYPE: DNA
<213> ORGANISM: Artificial
<220> FEATURE:
<223> OTHER INFORMATION: antisense nucleotide

<400> SEQUENCE: 27
cagcuucugu uagccacug                                                      19

<210> SEQ ID NO 28
<211> LENGTH: 21
<212> TYPE: DNA
<213> ORGANISM: Artificial
<220> FEATURE:
<223> OTHER INFORMATION: antisense nucleotide

<400> SEQUENCE: 28
cagcuucugu uagccacuga u                                                   21

<210> SEQ ID NO 29
<211> LENGTH: 21
<212> TYPE: DNA
<213> ORGANISM: Artificial
<220> FEATURE:
<223> OTHER INFORMATION: antisense nucleotide

<400> SEQUENCE: 29
agcuucuguu agccacugau u                                                   21

<210> SEQ ID NO 30
<211> LENGTH: 22
<212> TYPE: DNA
<213> ORGANISM: Artificial
<220> FEATURE:
<223> OTHER INFORMATION: antisense nucleotide
```

```
<400> SEQUENCE: 30
cagcuucugu uagccacuga uu                                              22

<210> SEQ ID NO 31
<211> LENGTH: 22
<212> TYPE: DNA
<213> ORGANISM: Artificial
<220> FEATURE:
<223> OTHER INFORMATION: antisense nucleotide

<400> SEQUENCE: 31
agcuucuguu agccacugau ua                                              22

<210> SEQ ID NO 32
<211> LENGTH: 23
<212> TYPE: DNA
<213> ORGANISM: Artificial
<220> FEATURE:
<223> OTHER INFORMATION: antisense nucleotide

<400> SEQUENCE: 32
cagcuucugu uagccacuga uua                                             23

<210> SEQ ID NO 33
<211> LENGTH: 23
<212> TYPE: DNA
<213> ORGANISM: Artificial
<220> FEATURE:
<223> OTHER INFORMATION: antisense nucleotide

<400> SEQUENCE: 33
agcuucuguu agccacugau uaa                                             23

<210> SEQ ID NO 34
<211> LENGTH: 24
<212> TYPE: DNA
<213> ORGANISM: Artificial
<220> FEATURE:
<223> OTHER INFORMATION: antisense nucleotide

<400> SEQUENCE: 34
cagcuucugu uagccacuga uuaa                                            24

<210> SEQ ID NO 35
<211> LENGTH: 24
<212> TYPE: DNA
<213> ORGANISM: Artificial
<220> FEATURE:
<223> OTHER INFORMATION: antisense nucleotide

<400> SEQUENCE: 35
agcuucuguu agccacugau uaaa                                            24

<210> SEQ ID NO 36
<211> LENGTH: 25
<212> TYPE: DNA
<213> ORGANISM: Artificial
<220> FEATURE:
<223> OTHER INFORMATION: antisense nucleotide

<400> SEQUENCE: 36
cagcuucugu uagccacuga uuaaa                                           25

<210> SEQ ID NO 37
<211> LENGTH: 24
```

```
<212> TYPE: DNA
<213> ORGANISM: Artificial
<220> FEATURE:
<223> OTHER INFORMATION: antisense nucleotide

<400> SEQUENCE: 37
agcuucuguu agccacugau uaaa                                              24

<210> SEQ ID NO 38
<211> LENGTH: 20
<212> TYPE: DNA
<213> ORGANISM: Artificial
<220> FEATURE:
<223> OTHER INFORMATION: antisense nucleotide

<400> SEQUENCE: 38
agcuucuguu agccacugau                                                   20

<210> SEQ ID NO 39
<211> LENGTH: 20
<212> TYPE: DNA
<213> ORGANISM: Artificial
<220> FEATURE:
<223> OTHER INFORMATION: antisense nucleotide

<400> SEQUENCE: 39
gcuucuguua gccacugauu                                                   20

<210> SEQ ID NO 40
<211> LENGTH: 21
<212> TYPE: DNA
<213> ORGANISM: Artificial
<220> FEATURE:
<223> OTHER INFORMATION: antisense nucleotide

<400> SEQUENCE: 40
agcuucuguu agccacugau u                                                 21

<210> SEQ ID NO 41
<211> LENGTH: 21
<212> TYPE: DNA
<213> ORGANISM: Artificial
<220> FEATURE:
<223> OTHER INFORMATION: antisense nucleotide

<400> SEQUENCE: 41
gcuucuguua gccacugauu a                                                 21

<210> SEQ ID NO 42
<211> LENGTH: 22
<212> TYPE: DNA
<213> ORGANISM: Artificial
<220> FEATURE:
<223> OTHER INFORMATION: antisense nucleotide

<400> SEQUENCE: 42
agcuucuguu agccacugau ua                                                22

<210> SEQ ID NO 43
<211> LENGTH: 22
<212> TYPE: DNA
<213> ORGANISM: Artificial
<220> FEATURE:
<223> OTHER INFORMATION: antisense nucleotide

<400> SEQUENCE: 43
```

```
gcuucuguua gccacugauu aa                                    22

<210> SEQ ID NO 44
<211> LENGTH: 23
<212> TYPE: DNA
<213> ORGANISM: Artificial
<220> FEATURE:
<223> OTHER INFORMATION: antisense nucleotide

<400> SEQUENCE: 44
agcuucuguu agccacugau uaa                                   23

<210> SEQ ID NO 45
<211> LENGTH: 23
<212> TYPE: DNA
<213> ORGANISM: Artificial
<220> FEATURE:
<223> OTHER INFORMATION: antisense nucleotide

<400> SEQUENCE: 45
gcuucuguua gccacugauu aaa                                   23

<210> SEQ ID NO 46
<211> LENGTH: 24
<212> TYPE: DNA
<213> ORGANISM: Artificial
<220> FEATURE:
<223> OTHER INFORMATION: antisense nucleotide

<400> SEQUENCE: 46
agcuucuguu agccacugau uaaa                                  24

<210> SEQ ID NO 47
<211> LENGTH: 23
<212> TYPE: DNA
<213> ORGANISM: Artificial
<220> FEATURE:
<223> OTHER INFORMATION: antisense nucleotide

<400> SEQUENCE: 47
gcuucuguua gccacugauu aaa                                   23

<210> SEQ ID NO 48
<211> LENGTH: 23
<212> TYPE: DNA
<213> ORGANISM: Artificial
<220> FEATURE:
<223> OTHER INFORMATION: antisense nucleotide

<400> SEQUENCE: 48
ccauuuguau uuagcauguu ccc                                   23

<210> SEQ ID NO 49
<211> LENGTH: 20
<212> TYPE: DNA
<213> ORGANISM: Artificial
<220> FEATURE:
<223> OTHER INFORMATION: antisense nucleotide

<400> SEQUENCE: 49
agauaccauu uguauuuagc                                       20

<210> SEQ ID NO 50
<211> LENGTH: 19
<212> TYPE: DNA
<213> ORGANISM: Artificial
```

```
<220> FEATURE:
<223> OTHER INFORMATION: antisense nucleotide

<400> SEQUENCE: 50
gccauuucuc aacagaucu                                              19

<210> SEQ ID NO 51
<211> LENGTH: 23
<212> TYPE: DNA
<213> ORGANISM: Artificial
<220> FEATURE:
<223> OTHER INFORMATION: antisense nucleotide

<400> SEQUENCE: 51
gccauuucuc aacagaucug uca                                         23

<210> SEQ ID NO 52
<211> LENGTH: 23
<212> TYPE: DNA
<213> ORGANISM: Artificial
<220> FEATURE:
<223> OTHER INFORMATION: antisense nucleotide

<400> SEQUENCE: 52
auucucagga auuugugucu uuc                                         23

<210> SEQ ID NO 53
<211> LENGTH: 21
<212> TYPE: DNA
<213> ORGANISM: Artificial
<220> FEATURE:
<223> OTHER INFORMATION: antisense nucleotide

<400> SEQUENCE: 53
ucucaggaau uugugucuuu c                                           21

<210> SEQ ID NO 54
<211> LENGTH: 18
<212> TYPE: DNA
<213> ORGANISM: Artificial
<220> FEATURE:
<223> OTHER INFORMATION: antisense nucleotide

<400> SEQUENCE: 54
guucagcuuc uguuagcc                                               18

<210> SEQ ID NO 55
<211> LENGTH: 21
<212> TYPE: DNA
<213> ORGANISM: Artificial
<220> FEATURE:
<223> OTHER INFORMATION: antisense nucleotide

<400> SEQUENCE: 55
cugauuaaau aucuuuauau c                                           21

<210> SEQ ID NO 56
<211> LENGTH: 18
<212> TYPE: DNA
<213> ORGANISM: Artificial
<220> FEATURE:
<223> OTHER INFORMATION: antisense nucleotide

<400> SEQUENCE: 56
gccgccauuu cucaacag                                               18
```

<210> SEQ ID NO 57
<211> LENGTH: 18
<212> TYPE: DNA
<213> ORGANISM: Artificial
<220> FEATURE:
<223> OTHER INFORMATION: antisense nucleotide

<400> SEQUENCE: 57
guauuuagca uguuccca                                              18

<210> SEQ ID NO 58
<211> LENGTH: 18
<212> TYPE: DNA
<213> ORGANISM: Artificial
<220> FEATURE:
<223> OTHER INFORMATION: antisense nucleotide

<400> SEQUENCE: 58
caggaauuug ugucuuuc                                              18

<210> SEQ ID NO 59
<211> LENGTH: 25
<212> TYPE: DNA
<213> ORGANISM: Artificial
<220> FEATURE:
<223> OTHER INFORMATION: antisense nucleotide

<400> SEQUENCE: 59
uuugccgcug cccaaugcca uccug                                      25

<210> SEQ ID NO 60
<211> LENGTH: 25
<212> TYPE: DNA
<213> ORGANISM: Artificial
<220> FEATURE:
<223> OTHER INFORMATION: antisense nucleotide

<400> SEQUENCE: 60
auucaauguu cugacaacag uuugc                                      25

<210> SEQ ID NO 61
<211> LENGTH: 25
<212> TYPE: DNA
<213> ORGANISM: Artificial
<220> FEATURE:
<223> OTHER INFORMATION: antisense nucleotide

<400> SEQUENCE: 61
ccaguugcau ucaauguucu gacaa                                      25

<210> SEQ ID NO 62
<211> LENGTH: 22
<212> TYPE: DNA
<213> ORGANISM: Artificial
<220> FEATURE:
<223> OTHER INFORMATION: antisense nucleotide

<400> SEQUENCE: 62
caguugcauu caauguucug ac                                         22

<210> SEQ ID NO 63
<211> LENGTH: 20
<212> TYPE: DNA
<213> ORGANISM: Artificial
<220> FEATURE:
<223> OTHER INFORMATION: antisense nucleotide -continued

```
<400> SEQUENCE: 63
aguugcauuc aauguucuga                                          20

<210> SEQ ID NO 64
<211> LENGTH: 21
<212> TYPE: DNA
<213> ORGANISM: Artificial
<220> FEATURE:
<223> OTHER INFORMATION: antisense nucleotide

<400> SEQUENCE: 64
gauugcugaa uuauuucuuc c                                        21

<210> SEQ ID NO 65
<211> LENGTH: 25
<212> TYPE: DNA
<213> ORGANISM: Artificial
<220> FEATURE:
<223> OTHER INFORMATION: antisense nucleotide

<400> SEQUENCE: 65
gauugcugaa uuauuucuuc cccag                                    25

<210> SEQ ID NO 66
<211> LENGTH: 25
<212> TYPE: DNA
<213> ORGANISM: Artificial
<220> FEATURE:
<223> OTHER INFORMATION: antisense nucleotide

<400> SEQUENCE: 66
auugcugaau uauuucuucc ccagu                                    25

<210> SEQ ID NO 67
<211> LENGTH: 25
<212> TYPE: DNA
<213> ORGANISM: Artificial
<220> FEATURE:
<223> OTHER INFORMATION: antisense nucleotide

<400> SEQUENCE: 67
uugcugaauu auuucuuccc caguu                                    25

<210> SEQ ID NO 68
<211> LENGTH: 25
<212> TYPE: DNA
<213> ORGANISM: Artificial
<220> FEATURE:
<223> OTHER INFORMATION: antisense nucleotide

<400> SEQUENCE: 68
ugcugaauua uuucuucccc aguug                                    25

<210> SEQ ID NO 69
<211> LENGTH: 25
<212> TYPE: DNA
<213> ORGANISM: Artificial
<220> FEATURE:
<223> OTHER INFORMATION: antisense nucleotide

<400> SEQUENCE: 69
gcugaauuau uucuucccca guugc                                    25

<210> SEQ ID NO 70
```

```
<211> LENGTH: 25
<212> TYPE: DNA
<213> ORGANISM: Artificial
<220> FEATURE:
<223> OTHER INFORMATION: antisense nucleotide

<400> SEQUENCE: 70
cugaauuauu ucuucccag uugca                                          25

<210> SEQ ID NO 71
<211> LENGTH: 25
<212> TYPE: DNA
<213> ORGANISM: Artificial
<220> FEATURE:
<223> OTHER INFORMATION: antisense nucleotide

<400> SEQUENCE: 71
ugaauuauuu cuucccagu ugcau                                          25

<210> SEQ ID NO 72
<211> LENGTH: 25
<212> TYPE: DNA
<213> ORGANISM: Artificial
<220> FEATURE:
<223> OTHER INFORMATION: antisense nucleotide

<400> SEQUENCE: 72
gaauuauuuc uucccaguu gcauu                                          25

<210> SEQ ID NO 73
<211> LENGTH: 25
<212> TYPE: DNA
<213> ORGANISM: Artificial
<220> FEATURE:
<223> OTHER INFORMATION: antisense nucleotide

<400> SEQUENCE: 73
aauuauuucu uccccaguug cauuc                                         25

<210> SEQ ID NO 74
<211> LENGTH: 25
<212> TYPE: DNA
<213> ORGANISM: Artificial
<220> FEATURE:
<223> OTHER INFORMATION: antisense nucleotide

<400> SEQUENCE: 74
auuauuucuu ccccaguugc auuca                                         25

<210> SEQ ID NO 75
<211> LENGTH: 25
<212> TYPE: DNA
<213> ORGANISM: Artificial
<220> FEATURE:
<223> OTHER INFORMATION: antisense nucleotide

<400> SEQUENCE: 75
uuauuucuuc cccaguugca uucaa                                         25

<210> SEQ ID NO 76
<211> LENGTH: 25
<212> TYPE: DNA
<213> ORGANISM: Artificial
<220> FEATURE:
<223> OTHER INFORMATION: antisense nucleotide

<400> SEQUENCE: 76
```
uauuucuucc ccaguugcau ucaau　　　　　　　　　　　　　　　　25

<210> SEQ ID NO 77
<211> LENGTH: 25
<212> TYPE: DNA
<213> ORGANISM: Artificial
<220> FEATURE:
<223> OTHER INFORMATION: antisense nucleotide

<400> SEQUENCE: 77
auuucuuccc caguugcauu caaug　　　　　　　　　　　　　　　　25

<210> SEQ ID NO 78
<211> LENGTH: 25
<212> TYPE: DNA
<213> ORGANISM: Artificial
<220> FEATURE:
<223> OTHER INFORMATION: antisense nucleotide

<400> SEQUENCE: 78 uuucuuccccc aguugcauuc aaugu　　　　　　　　　　　　　　　　25

<210> SEQ ID NO 79
<211> LENGTH: 25
<212> TYPE: DNA
<213> ORGANISM: Artificial
<220> FEATURE:
<223> OTHER INFORMATION: antisense nucleotide

<400> SEQUENCE: 79
uucuucccca guugcauuca auguu　　　　　　　　　　　　　　　　25

<210> SEQ ID NO 80
<211> LENGTH: 25
<212> TYPE: DNA
<213> ORGANISM: Artificial
<220> FEATURE:
<223> OTHER INFORMATION: antisense nucleotide

<400> SEQUENCE: 80 ucuucccag uugcauucaa uguuc　　　　　　　　　　　　　　　　25

<210> SEQ ID NO 81
<211> LENGTH: 25
<212> TYPE: DNA
<213> ORGANISM: Artificial
<220> FEATURE:
<223> OTHER INFORMATION: antisense nucleotide

<400> SEQUENCE: 81 cuucccagu ugcauucaau guucu　　　　　　　　　　　　　　　　25

<210> SEQ ID NO 82
<211> LENGTH: 25
<212> TYPE: DNA
<213> ORGANISM: Artificial
<220> FEATURE:
<223> OTHER INFORMATION: antisense nucleotide

<400> SEQUENCE: 82
uuccccaguu gcauucaaug uucug　　　　　　　　　　　　　　　　25

<210> SEQ ID NO 83
<211> LENGTH: 25
<212> TYPE: DNA

```
<213> ORGANISM: Artificial
<220> FEATURE:
<223> OTHER INFORMATION: antisense nucleotide

<400> SEQUENCE: 83
uccccaguug cauucaaugu ucuga                                              25

<210> SEQ ID NO 84
<211> LENGTH: 25
<212> TYPE: DNA
<213> ORGANISM: Artificial
<220> FEATURE:
<223> OTHER INFORMATION: antisense nucleotide

<400> SEQUENCE: 84
ccccaguugc auucaauguu cugac                                              25

<210> SEQ ID NO 85
<211> LENGTH: 25
<212> TYPE: DNA
<213> ORGANISM: Artificial
<220> FEATURE:
<223> OTHER INFORMATION: antisense nucleotide

<400> SEQUENCE: 85
cccaguugca uucaauguuc ugaca                                              25

<210> SEQ ID NO 86
<211> LENGTH: 25
<212> TYPE: DNA
<213> ORGANISM: Artificial
<220> FEATURE:
<223> OTHER INFORMATION: antisense nucleotide

<400> SEQUENCE: 86
ccaguugcau ucaauguucu gacaa                                              25

<210> SEQ ID NO 87
<211> LENGTH: 25
<212> TYPE: DNA
<213> ORGANISM: Artificial
<220> FEATURE:
<223> OTHER INFORMATION: antisense nucleotide

<400> SEQUENCE: 87
caguugcauu caauguucug acaac                                              25

<210> SEQ ID NO 88
<211> LENGTH: 25
<212> TYPE: DNA
<213> ORGANISM: Artificial
<220> FEATURE:
<223> OTHER INFORMATION: antisense nucleotide

<400> SEQUENCE: 88
aguugcauuc aauguucuga caaca                                              25

<210> SEQ ID NO 89
<211> LENGTH: 25
<212> TYPE: DNA
<213> ORGANISM: Artificial
<220> FEATURE:
<223> OTHER INFORMATION: antisense nucleotide

<400> SEQUENCE: 89
guugcauuca auguucugac aacag                                              25
```

```
<210> SEQ ID NO 90
<211> LENGTH: 25
<212> TYPE: DNA
<213> ORGANISM: Artificial
<220> FEATURE:
<223> OTHER INFORMATION: antisense nucleotide

<400> SEQUENCE: 90
uugcauucaa uguucugaca acagu                                              25

<210> SEQ ID NO 91
<211> LENGTH: 25
<212> TYPE: DNA
<213> ORGANISM: Artificial
<220> FEATURE:
<223> OTHER INFORMATION: antisense nucleotide

<400> SEQUENCE: 91
ugcauucaau guucugacaa caguu                                              25

<210> SEQ ID NO 92
<211> LENGTH: 25
<212> TYPE: DNA
<213> ORGANISM: Artificial
<220> FEATURE:
<223> OTHER INFORMATION: antisense nucleotide

<400> SEQUENCE: 92
gcauucaaug uucugacaac aguuu                                              25

<210> SEQ ID NO 93
<211> LENGTH: 25
<212> TYPE: DNA
<213> ORGANISM: Artificial
<220> FEATURE:
<223> OTHER INFORMATION: antisense nucleotide

<400> SEQUENCE: 93
cauucaaugu ucugacaaca guuug                                              25

<210> SEQ ID NO 94
<211> LENGTH: 25
<212> TYPE: DNA
<213> ORGANISM: Artificial
<220> FEATURE:
<223> OTHER INFORMATION: antisense nucleotide

<400> SEQUENCE: 94
auucaauguu cugacaacag uuugc                                              25

<210> SEQ ID NO 95
<211> LENGTH: 25
<212> TYPE: DNA
<213> ORGANISM: Artificial
<220> FEATURE:
<223> OTHER INFORMATION: antisense nucleotide

<400> SEQUENCE: 95
ucaauguucu gacaacaguu ugccg                                              25

<210> SEQ ID NO 96
<211> LENGTH: 25
<212> TYPE: DNA
<213> ORGANISM: Artificial
<220> FEATURE:
```

```
<223> OTHER INFORMATION: antisense nucleotide

<400> SEQUENCE: 96
caauguucug acaacaguuu gccgc                                              25

<210> SEQ ID NO 97
<211> LENGTH: 25
<212> TYPE: DNA
<213> ORGANISM: Artificial
<220> FEATURE:
<223> OTHER INFORMATION: antisense nucleotide

<400> SEQUENCE: 97
aauguucuga caacaguuug ccgcu                                              25

<210> SEQ ID NO 98
<211> LENGTH: 25
<212> TYPE: DNA
<213> ORGANISM: Artificial
<220> FEATURE:
<223> OTHER INFORMATION: antisense nucleotide

<400> SEQUENCE: 98
auguucugac aacaguuugc cgcug                                              25

<210> SEQ ID NO 99
<211> LENGTH: 25
<212> TYPE: DNA
<213> ORGANISM: Artificial
<220> FEATURE:
<223> OTHER INFORMATION: antisense nucleotide

<400> SEQUENCE: 99
uguucugaca acaguuugcc gcugc                                              25

<210> SEQ ID NO 100
<211> LENGTH: 25
<212> TYPE: DNA
<213> ORGANISM: Artificial
<220> FEATURE:
<223> OTHER INFORMATION: antisense nucleotide

<400> SEQUENCE: 100
guucugacaa caguuugccg cugcc                                              25

<210> SEQ ID NO 101
<211> LENGTH: 25
<212> TYPE: DNA
<213> ORGANISM: Artificial
<220> FEATURE:
<223> OTHER INFORMATION: antisense nucleotide

<400> SEQUENCE: 101
uucugacaac aguuugccgc ugccc                                              25

<210> SEQ ID NO 102
<211> LENGTH: 25
<212> TYPE: DNA
<213> ORGANISM: Artificial
<220> FEATURE:
<223> OTHER INFORMATION: antisense nucleotide

<400> SEQUENCE: 102
ucugacaaca guuugccgcu gccca                                              25
```

```
<210> SEQ ID NO 103
<211> LENGTH: 25
<212> TYPE: DNA
<213> ORGANISM: Artificial
<220> FEATURE:
<223> OTHER INFORMATION: antisense nucleotide

<400> SEQUENCE: 103
cugacaacag uuugccgcug cccaa                                            25

<210> SEQ ID NO 104
<211> LENGTH: 25
<212> TYPE: DNA
<213> ORGANISM: Artificial
<220> FEATURE:
<223> OTHER INFORMATION: antisense nucleotide

<400> SEQUENCE: 104
ugacaacagu uugccgcugc ccaau                                            25

<210> SEQ ID NO 105
<211> LENGTH: 25
<212> TYPE: DNA
<213> ORGANISM: Artificial
<220> FEATURE:
<223> OTHER INFORMATION: antisense nucleotide

<400> SEQUENCE: 105
gacaacaguu ugccgcugcc caaug                                            25

<210> SEQ ID NO 106
<211> LENGTH: 25
<212> TYPE: DNA
<213> ORGANISM: Artificial
<220> FEATURE:
<223> OTHER INFORMATION: antisense nucleotide

<400> SEQUENCE: 106
acaacaguuu gccgcugccc aaugc                                            25

<210> SEQ ID NO 107
<211> LENGTH: 25
<212> TYPE: DNA
<213> ORGANISM: Artificial
<220> FEATURE:
<223> OTHER INFORMATION: antisense nucleotide

<400> SEQUENCE: 107
caacaguuug ccgcugccca augcc                                            25

<210> SEQ ID NO 108
<211> LENGTH: 25
<212> TYPE: DNA
<213> ORGANISM: Artificial
<220> FEATURE:
<223> OTHER INFORMATION: antisense nucleotide

<400> SEQUENCE: 108
aacaguuugc cgcugcccaa ugcca                                            25

<210> SEQ ID NO 109
<211> LENGTH: 25
<212> TYPE: DNA
<213> ORGANISM: Artificial
<220> FEATURE:
<223> OTHER INFORMATION: antisense nucleotide
```

```
<400> SEQUENCE: 109
acaguuugcc gcugcccaau gccau                                           25

<210> SEQ ID NO 110
<211> LENGTH: 25
<212> TYPE: DNA
<213> ORGANISM: Artificial
<220> FEATURE:
<223> OTHER INFORMATION: antisense nucleotide

<400> SEQUENCE: 110
caguuugccg cugcccaaug ccauc                                           25

<210> SEQ ID NO 111
<211> LENGTH: 25
<212> TYPE: DNA
<213> ORGANISM: Artificial
<220> FEATURE:
<223> OTHER INFORMATION: antisense nucleotide

<400> SEQUENCE: 111
aguuugccgc ugcccaaugc caucc                                           25

<210> SEQ ID NO 112
<211> LENGTH: 25
<212> TYPE: DNA
<213> ORGANISM: Artificial
<220> FEATURE:
<223> OTHER INFORMATION: antisense nucleotide

<400> SEQUENCE: 112
guuugccgcu gcccaaugcc auccu                                           25

<210> SEQ ID NO 113
<211> LENGTH: 25
<212> TYPE: DNA
<213> ORGANISM: Artificial
<220> FEATURE:
<223> OTHER INFORMATION: antisense nucleotide

<400> SEQUENCE: 113
uuugccgcug cccaaugcca uccug                                           25

<210> SEQ ID NO 114
<211> LENGTH: 25
<212> TYPE: DNA
<213> ORGANISM: Artificial
<220> FEATURE:
<223> OTHER INFORMATION: antisense nucleotide

<400> SEQUENCE: 114
uugccgcugc ccaaugccau ccugg                                           25

<210> SEQ ID NO 115
<211> LENGTH: 25
<212> TYPE: DNA
<213> ORGANISM: Artificial
<220> FEATURE:
<223> OTHER INFORMATION: antisense nucleotide

<400> SEQUENCE: 115
ugccgcugcc caaugccauc cugga                                           25

<210> SEQ ID NO 116
<211> LENGTH: 25
```

```
<212> TYPE: DNA
<213> ORGANISM: Artificial
<220> FEATURE:
<223> OTHER INFORMATION: antisense nucleotide

<400> SEQUENCE: 116
gccgcugccc aaugccaucc uggag                                    25

<210> SEQ ID NO 117
<211> LENGTH: 25
<212> TYPE: DNA
<213> ORGANISM: Artificial
<220> FEATURE:
<223> OTHER INFORMATION: antisense nucleotide

<400> SEQUENCE: 117
ccgcugccca augccauccu ggagu                                    25

<210> SEQ ID NO 118
<211> LENGTH: 25
<212> TYPE: DNA
<213> ORGANISM: Artificial
<220> FEATURE:
<223> OTHER INFORMATION: antisense nucleotide

<400> SEQUENCE: 118
cgcugcccaa ugccauccug gaguu                                    25

<210> SEQ ID NO 119
<211> LENGTH: 25
<212> TYPE: DNA
<213> ORGANISM: Artificial
<220> FEATURE:
<223> OTHER INFORMATION: antisense nucleotide

<400> SEQUENCE: 119 gcuuucuuu uaguugcugc ucuuu                                     25

<210> SEQ ID NO 120
<211> LENGTH: 25
<212> TYPE: DNA
<213> ORGANISM: Artificial
<220> FEATURE:
<223> OTHER INFORMATION: antisense nucleotide

<400> SEQUENCE: 120 cuuucuuuu aguugcugcu cuuuu                                     25

<210> SEQ ID NO 121
<211> LENGTH: 25
<212> TYPE: DNA
<213> ORGANISM: Artificial
<220> FEATURE:
<223> OTHER INFORMATION: antisense nucleotide

<400> SEQUENCE: 121
uuuucuuuua guugcugcuc uuuuc                                    25

<210> SEQ ID NO 122
<211> LENGTH: 25
<212> TYPE: DNA
<213> ORGANISM: Artificial
<220> FEATURE:
<223> OTHER INFORMATION: antisense nucleotide

<400> SEQUENCE: 122
``` uucuuuuag uugcugcucu uuucc 25

<210> SEQ ID NO 123
<211> LENGTH: 25
<212> TYPE: DNA
<213> ORGANISM: Artificial
<220> FEATURE:
<223> OTHER INFORMATION: antisense nucleotide

<400> SEQUENCE: 123
uucuuuuagu ugcugcucuu uucca 25

<210> SEQ ID NO 124
<211> LENGTH: 25
<212> TYPE: DNA
<213> ORGANISM: Artificial
<220> FEATURE:
<223> OTHER INFORMATION: antisense nucleotide

<400> SEQUENCE: 124 ucuuuaguu gcugcucuuu uccag 25

<210> SEQ ID NO 125
<211> LENGTH: 25
<212> TYPE: DNA
<213> ORGANISM: Artificial
<220> FEATURE:
<223> OTHER INFORMATION: antisense nucleotide

<400> SEQUENCE: 125 cuuuaguug cugcucuuuu ccagg 25

<210> SEQ ID NO 126
<211> LENGTH: 25
<212> TYPE: DNA
<213> ORGANISM: Artificial
<220> FEATURE:
<223> OTHER INFORMATION: antisense nucleotide

<400> SEQUENCE: 126 uuuaguugc ugcucuuuuc caggu 25

<210> SEQ ID NO 127
<211> LENGTH: 25
<212> TYPE: DNA
<213> ORGANISM: Artificial
<220> FEATURE:
<223> OTHER INFORMATION: antisense nucleotide

<400> SEQUENCE: 127 uuaguugcu gcucuuucc agguu 25

<210> SEQ ID NO 128
<211> LENGTH: 25
<212> TYPE: DNA
<213> ORGANISM: Artificial
<220> FEATURE:
<223> OTHER INFORMATION: antisense nucleotide

<400> SEQUENCE: 128
uuaguugcug cucuuuucca gguuc 25

<210> SEQ ID NO 129
<211> LENGTH: 25
<212> TYPE: DNA
<213> ORGANISM: Artificial

```
<220> FEATURE:
<223> OTHER INFORMATION: antisense nucleotide

<400> SEQUENCE: 129
uaguugcugc ucuuuccag guuca                                          25

<210> SEQ ID NO 130
<211> LENGTH: 25
<212> TYPE: DNA
<213> ORGANISM: Artificial
<220> FEATURE:
<223> OTHER INFORMATION: antisense nucleotide

<400> SEQUENCE: 130
aguugcugcu cuuuccaggu ucaa                                          25

<210> SEQ ID NO 131
<211> LENGTH: 25
<212> TYPE: DNA
<213> ORGANISM: Artificial
<220> FEATURE:
<223> OTHER INFORMATION: antisense nucleotide

<400> SEQUENCE: 131
guugcugcuc uuuccaggu ucaag                                          25

<210> SEQ ID NO 132
<211> LENGTH: 25
<212> TYPE: DNA
<213> ORGANISM: Artificial
<220> FEATURE:
<223> OTHER INFORMATION: antisense nucleotide

<400> SEQUENCE: 132
uugcugcucu uuccagguu caagu                                          25

<210> SEQ ID NO 133
<211> LENGTH: 25
<212> TYPE: DNA
<213> ORGANISM: Artificial
<220> FEATURE:
<223> OTHER INFORMATION: antisense nucleotide

<400> SEQUENCE: 133
ugcugcucuu uuccagguuc aagug                                         25

<210> SEQ ID NO 134
<211> LENGTH: 25
<212> TYPE: DNA
<213> ORGANISM: Artificial
<220> FEATURE:
<223> OTHER INFORMATION: antisense nucleotide

<400> SEQUENCE: 134
gcugcucuuu uccagguuca agugg                                         25

<210> SEQ ID NO 135
<211> LENGTH: 25
<212> TYPE: DNA
<213> ORGANISM: Artificial
<220> FEATURE:
<223> OTHER INFORMATION: antisense nucleotide

<400> SEQUENCE: 135
cugcucuuuu ccagguucaa guggg                                         25
```

<210> SEQ ID NO 136
<211> LENGTH: 25
<212> TYPE: DNA
<213> ORGANISM: Artificial
<220> FEATURE:
<223> OTHER INFORMATION: antisense nucleotide

<400> SEQUENCE: 136
ugcucuuuuc cagguucaag uggga                                              25

<210> SEQ ID NO 137
<211> LENGTH: 25
<212> TYPE: DNA
<213> ORGANISM: Artificial
<220> FEATURE:
<223> OTHER INFORMATION: antisense nucleotide

<400> SEQUENCE: 137
gcucuuuucc agguucaagu gggac                                              25

<210> SEQ ID NO 138
<211> LENGTH: 25
<212> TYPE: DNA
<213> ORGANISM: Artificial
<220> FEATURE:
<223> OTHER INFORMATION: antisense nucleotide

<400> SEQUENCE: 138
cucuuuucca gguucaagug ggaua                                              25

<210> SEQ ID NO 139
<211> LENGTH: 25
<212> TYPE: DNA
<213> ORGANISM: Artificial
<220> FEATURE:
<223> OTHER INFORMATION: antisense nucleotide

<400> SEQUENCE: 139
ucuuuuccag guucaagugg gauac                                              25

<210> SEQ ID NO 140
<211> LENGTH: 25
<212> TYPE: DNA
<213> ORGANISM: Artificial
<220> FEATURE:
<223> OTHER INFORMATION: antisense nucleotide

<400> SEQUENCE: 140
cuuuuccagg uucaaguggg auacu                                              25

<210> SEQ ID NO 141
<211> LENGTH: 25
<212> TYPE: DNA
<213> ORGANISM: Artificial
<220> FEATURE:
<223> OTHER INFORMATION: antisense nucleotide

<400> SEQUENCE: 141
uuuuccaggu ucaaguggga uacua                                              25

<210> SEQ ID NO 142
<211> LENGTH: 25
<212> TYPE: DNA
<213> ORGANISM: Artificial
<220> FEATURE:
<223> OTHER INFORMATION: antisense nucleotide

```
<400> SEQUENCE: 142
uuuccagguu caagugggau acuag                                              25

<210> SEQ ID NO 143
<211> LENGTH: 25
<212> TYPE: DNA
<213> ORGANISM: Artificial
<220> FEATURE:
<223> OTHER INFORMATION: antisense nucleotide

<400> SEQUENCE: 143
uuccagguuc aagugggaua cuagc                                              25

<210> SEQ ID NO 144
<211> LENGTH: 25
<212> TYPE: DNA
<213> ORGANISM: Artificial
<220> FEATURE:
<223> OTHER INFORMATION: antisense nucleotide

<400> SEQUENCE: 144
uccagguuca agugggauac uagca                                              25

<210> SEQ ID NO 145
<211> LENGTH: 25
<212> TYPE: DNA
<213> ORGANISM: Artificial
<220> FEATURE:
<223> OTHER INFORMATION: antisense nucleotide

<400> SEQUENCE: 145
ccagguucaa gugggauacu agcaa                                              25

<210> SEQ ID NO 146
<211> LENGTH: 25
<212> TYPE: DNA
<213> ORGANISM: Artificial
<220> FEATURE:
<223> OTHER INFORMATION: antisense nucleotide

<400> SEQUENCE: 146
cagguucaag ugggauacua gcaau                                              25

<210> SEQ ID NO 147
<211> LENGTH: 25
<212> TYPE: DNA
<213> ORGANISM: Artificial
<220> FEATURE:
<223> OTHER INFORMATION: antisense nucleotide

<400> SEQUENCE: 147
agguucaagu gggauacuag caaug                                              25

<210> SEQ ID NO 148
<211> LENGTH: 25
<212> TYPE: DNA
<213> ORGANISM: Artificial
<220> FEATURE:
<223> OTHER INFORMATION: antisense nucleotide

<400> SEQUENCE: 148
gguucaagug ggauacuagc aaugu                                              25

<210> SEQ ID NO 149
```

```
<211> LENGTH: 25
<212> TYPE: DNA
<213> ORGANISM: Artificial
<220> FEATURE:
<223> OTHER INFORMATION: antisense nucleotide

<400> SEQUENCE: 149
guucaagugg gauacuagca auguu                                     25

<210> SEQ ID NO 150
<211> LENGTH: 25
<212> TYPE: DNA
<213> ORGANISM: Artificial
<220> FEATURE:
<223> OTHER INFORMATION: antisense nucleotide

<400> SEQUENCE: 150
uucaaguggg auacuagcaa uguua                                     25

<210> SEQ ID NO 151
<211> LENGTH: 25
<212> TYPE: DNA
<213> ORGANISM: Artificial
<220> FEATURE:
<223> OTHER INFORMATION: antisense nucleotide

<400> SEQUENCE: 151
ucaaguggga uacuagcaau guuau                                     25

<210> SEQ ID NO 152
<211> LENGTH: 25
<212> TYPE: DNA
<213> ORGANISM: Artificial
<220> FEATURE:
<223> OTHER INFORMATION: antisense nucleotide

<400> SEQUENCE: 152
caagugggau acuagcaaug uuauc                                     25

<210> SEQ ID NO 153
<211> LENGTH: 25
<212> TYPE: DNA
<213> ORGANISM: Artificial
<220> FEATURE:
<223> OTHER INFORMATION: antisense nucleotide

<400> SEQUENCE: 153
aagugggaua cuagcaaugu uaucu                                     25

<210> SEQ ID NO 154
<211> LENGTH: 25
<212> TYPE: DNA
<213> ORGANISM: Artificial
<220> FEATURE:
<223> OTHER INFORMATION: antisense nucleotide

<400> SEQUENCE: 154
agugggauac uagcaauguu aucug                                     25

<210> SEQ ID NO 155
<211> LENGTH: 25
<212> TYPE: DNA
<213> ORGANISM: Artificial
<220> FEATURE:
<223> OTHER INFORMATION: antisense nucleotide

<400> SEQUENCE: 155
```
gugggauacu agcaauguua ucugc            25

<210> SEQ ID NO 156
<211> LENGTH: 25
<212> TYPE: DNA
<213> ORGANISM: Artificial
<220> FEATURE:
<223> OTHER INFORMATION: antisense nucleotide

<400> SEQUENCE: 156
ugggauacua gcaauguuau cugcu            25

<210> SEQ ID NO 157
<211> LENGTH: 25
<212> TYPE: DNA
<213> ORGANISM: Artificial
<220> FEATURE:
<223> OTHER INFORMATION: antisense nucleotide

<400> SEQUENCE: 157
gggauacuag caauguuauc ugcuu            25

<210> SEQ ID NO 158
<211> LENGTH: 25
<212> TYPE: DNA
<213> ORGANISM: Artificial
<220> FEATURE:
<223> OTHER INFORMATION: antisense nucleotide

<400> SEQUENCE: 158
ggauacuagc aauguuaucu gcuuc            25

<210> SEQ ID NO 159
<211> LENGTH: 25
<212> TYPE: DNA
<213> ORGANISM: Artificial
<220> FEATURE:
<223> OTHER INFORMATION: antisense nucleotide

<400> SEQUENCE: 159
gauacuagca auguuaucug cuucc            25

<210> SEQ ID NO 160
<211> LENGTH: 25
<212> TYPE: DNA
<213> ORGANISM: Artificial
<220> FEATURE:
<223> OTHER INFORMATION: antisense nucleotide

<400> SEQUENCE: 160
auacuagcaa uguuaucugc uuccu            25

<210> SEQ ID NO 161
<211> LENGTH: 25
<212> TYPE: DNA
<213> ORGANISM: Artificial
<220> FEATURE:
<223> OTHER INFORMATION: antisense nucleotide

<400> SEQUENCE: 161
uacuagcaau guuaucugcu uccuc            25

<210> SEQ ID NO 162
<211> LENGTH: 25
<212> TYPE: DNA

<213> ORGANISM: Artificial
<220> FEATURE:
<223> OTHER INFORMATION: antisense nucleotide

<400> SEQUENCE: 162
acuagcaaug uuaucugcuu ccucc                                    25

<210> SEQ ID NO 163
<211> LENGTH: 25
<212> TYPE: DNA
<213> ORGANISM: Artificial
<220> FEATURE:
<223> OTHER INFORMATION: antisense nucleotide

<400> SEQUENCE: 163
cuagcaaugu uaucugcuuc cucca                                    25

<210> SEQ ID NO 164
<211> LENGTH: 25
<212> TYPE: DNA
<213> ORGANISM: Artificial
<220> FEATURE:
<223> OTHER INFORMATION: antisense nucleotide

<400> SEQUENCE: 164
uagcaauguu aucugcuucc uccaa                                    25

<210> SEQ ID NO 165
<211> LENGTH: 25
<212> TYPE: DNA
<213> ORGANISM: Artificial
<220> FEATURE:
<223> OTHER INFORMATION: antisense nucleotide

<400> SEQUENCE: 165
agcaauguua ucugcuuccu ccaac                                    25

<210> SEQ ID NO 166
<211> LENGTH: 25
<212> TYPE: DNA
<213> ORGANISM: Artificial
<220> FEATURE:
<223> OTHER INFORMATION: antisense nucleotide

<400> SEQUENCE: 166
gcaauguuau cugcuuccuc caacc                                    25

<210> SEQ ID NO 167
<211> LENGTH: 25
<212> TYPE: DNA
<213> ORGANISM: Artificial
<220> FEATURE:
<223> OTHER INFORMATION: antisense nucleotide

<400> SEQUENCE: 167
caauguuauc ugcuuccucc aacca                                    25

<210> SEQ ID NO 168
<211> LENGTH: 25
<212> TYPE: DNA
<213> ORGANISM: Artificial
<220> FEATURE:
<223> OTHER INFORMATION: antisense nucleotide

<400> SEQUENCE: 168
aauguuaucu gcuuccucca accau                                    25

<210> SEQ ID NO 169
<211> LENGTH: 25
<212> TYPE: DNA
<213> ORGANISM: Artificial
<220> FEATURE:
<223> OTHER INFORMATION: antisense nucleotide

<400> SEQUENCE: 169
auguuaucug cuuccuccaa ccaua                                          25

<210> SEQ ID NO 170
<211> LENGTH: 25
<212> TYPE: DNA
<213> ORGANISM: Artificial
<220> FEATURE:
<223> OTHER INFORMATION: antisense nucleotide

<400> SEQUENCE: 170
uguuaucugc uuccuccaac cauaa                                          25

<210> SEQ ID NO 171
<211> LENGTH: 25
<212> TYPE: DNA
<213> ORGANISM: Artificial
<220> FEATURE:
<223> OTHER INFORMATION: antisense nucleotide

<400> SEQUENCE: 171
guuaucugcu uccuccaacc auaaa                                          25

<210> SEQ ID NO 172
<211> LENGTH: 19
<212> TYPE: DNA
<213> ORGANISM: Artificial
<220> FEATURE:
<223> OTHER INFORMATION: antisense nucleotide

<400> SEQUENCE: 172
gcugcucuuu uccagguuc                                                 19

<210> SEQ ID NO 173
<211> LENGTH: 20
<212> TYPE: DNA
<213> ORGANISM: Artificial
<220> FEATURE:
<223> OTHER INFORMATION: antisense nucleotide

<400> SEQUENCE: 173 ucuuuccag guucaagugg                                                 20

<210> SEQ ID NO 174
<211> LENGTH: 19
<212> TYPE: DNA
<213> ORGANISM: Artificial
<220> FEATURE:
<223> OTHER INFORMATION: antisense nucleotide

<400> SEQUENCE: 174
agguucaagu gggauacua                                                 19

<210> SEQ ID NO 175
<211> LENGTH: 20
<212> TYPE: DNA
<213> ORGANISM: Artificial
<220> FEATURE:

```
<223> OTHER INFORMATION: antisense nucleotide

<400> SEQUENCE: 175
cucagcucuu gaaguaaacg                                                    20

<210> SEQ ID NO 176
<211> LENGTH: 20
<212> TYPE: DNA
<213> ORGANISM: Artificial
<220> FEATURE:
<223> OTHER INFORMATION: antisense nucleotide

<400> SEQUENCE: 176
ccucagcucu ugaaguaaac                                                    20

<210> SEQ ID NO 177
<211> LENGTH: 21
<212> TYPE: DNA
<213> ORGANISM: Artificial
<220> FEATURE:
<223> OTHER INFORMATION: antisense nucleotide

<400> SEQUENCE: 177
ccucagcucu ugaaguaaac g                                                  21

<210> SEQ ID NO 178
<211> LENGTH: 21
<212> TYPE: DNA
<213> ORGANISM: Artificial
<220> FEATURE:
<223> OTHER INFORMATION: antisense nucleotide

<400> SEQUENCE: 178
auagugguca guccaggagc u                                                  21

<210> SEQ ID NO 179
<211> LENGTH: 21
<212> TYPE: DNA
<213> ORGANISM: Artificial
<220> FEATURE:
<223> OTHER INFORMATION: antisense nucleotide

<400> SEQUENCE: 179
caguccagga gcuaggucag g                                                  21

<210> SEQ ID NO 180
<211> LENGTH: 25
<212> TYPE: DNA
<213> ORGANISM: Artificial
<220> FEATURE:
<223> OTHER INFORMATION: antisense nucleotide

<400> SEQUENCE: 180
uaguggucag uccaggagcu agguc                                              25

<210> SEQ ID NO 181
<211> LENGTH: 25
<212> TYPE: DNA
<213> ORGANISM: Artificial
<220> FEATURE:
<223> OTHER INFORMATION: antisense nucleotide

<400> SEQUENCE: 181
agagcaggua ccuccaacau caagg                                              25
```

<210> SEQ ID NO 182
<211> LENGTH: 25
<212> TYPE: DNA
<213> ORGANISM: Artificial
<220> FEATURE:
<223> OTHER INFORMATION: antisense nucleotide

<400> SEQUENCE: 182
gagcagguac cuccaacauc aagga                                          25

<210> SEQ ID NO 183
<211> LENGTH: 25
<212> TYPE: DNA
<213> ORGANISM: Artificial
<220> FEATURE:
<223> OTHER INFORMATION: antisense nucleotide

<400> SEQUENCE: 183
agcagguacc uccaacauca aggaa                                          25

<210> SEQ ID NO 184
<211> LENGTH: 25
<212> TYPE: DNA
<213> ORGANISM: Artificial
<220> FEATURE:
<223> OTHER INFORMATION: antisense nucleotide

<400> SEQUENCE: 184
gcagguaccu ccaacaucaa ggaag                                          25

<210> SEQ ID NO 185
<211> LENGTH: 25
<212> TYPE: DNA
<213> ORGANISM: Artificial
<220> FEATURE:
<223> OTHER INFORMATION: antisense nucleotide

<400> SEQUENCE: 185
cagguaccuc caacaucaag gaaga                                          25

<210> SEQ ID NO 186
<211> LENGTH: 25
<212> TYPE: DNA
<213> ORGANISM: Artificial
<220> FEATURE:
<223> OTHER INFORMATION: antisense nucleotide

<400> SEQUENCE: 186
agguaccucc aacaucaagg aagau                                          25

<210> SEQ ID NO 187
<211> LENGTH: 25
<212> TYPE: DNA
<213> ORGANISM: Artificial
<220> FEATURE:
<223> OTHER INFORMATION: antisense nucleotide

<400> SEQUENCE: 187
gguaccucca acaucaagga agaug                                          25

<210> SEQ ID NO 188
<211> LENGTH: 25
<212> TYPE: DNA
<213> ORGANISM: Artificial
<220> FEATURE:
<223> OTHER INFORMATION: antisense nucleotide

```
<400> SEQUENCE: 188
guaccuccaa caucaaggaa gaugg                                        25

<210> SEQ ID NO 189
<211> LENGTH: 25
<212> TYPE: DNA
<213> ORGANISM: Artificial
<220> FEATURE:
<223> OTHER INFORMATION: antisense nucleotide

<400> SEQUENCE: 189
uaccuccaac aucaaggaag auggc                                        25

<210> SEQ ID NO 190
<211> LENGTH: 25
<212> TYPE: DNA
<213> ORGANISM: Artificial
<220> FEATURE:
<223> OTHER INFORMATION: antisense nucleotide

<400> SEQUENCE: 190
accuccaaca ucaaggaaga uggca                                        25

<210> SEQ ID NO 191
<211> LENGTH: 25
<212> TYPE: DNA
<213> ORGANISM: Artificial
<220> FEATURE:
<223> OTHER INFORMATION: antisense nucleotide

<400> SEQUENCE: 191
ccuccaacau caaggaagau ggcau                                        25

<210> SEQ ID NO 192
<211> LENGTH: 25
<212> TYPE: DNA
<213> ORGANISM: Artificial
<220> FEATURE:
<223> OTHER INFORMATION: antisense nucleotide

<400> SEQUENCE: 192
cuccaacauc aaggaagaug gcauu                                        25

<210> SEQ ID NO 193
<211> LENGTH: 30
<212> TYPE: DNA
<213> ORGANISM: Artificial
<220> FEATURE:
<223> OTHER INFORMATION: antisense nucleotide

<400> SEQUENCE: 193
cuccaacauc aaggaagaug gcauuucuag                                   30

<210> SEQ ID NO 194
<211> LENGTH: 25
<212> TYPE: DNA
<213> ORGANISM: Artificial
<220> FEATURE:
<223> OTHER INFORMATION: antisense nucleotide

<400> SEQUENCE: 194
uccaacauca aggaagaugg cauuu                                        25

<210> SEQ ID NO 195
<211> LENGTH: 25
```

```
<212> TYPE: DNA
<213> ORGANISM: Artificial
<220> FEATURE:
<223> OTHER INFORMATION: antisense nucleotide

<400> SEQUENCE: 195
ccaacaucaa ggaagauggc auuuc                                              25

<210> SEQ ID NO 196
<211> LENGTH: 25
<212> TYPE: DNA
<213> ORGANISM: Artificial
<220> FEATURE:
<223> OTHER INFORMATION: antisense nucleotide

<400> SEQUENCE: 196
caacaucaag gaagauggca uuucu                                              25

<210> SEQ ID NO 197
<211> LENGTH: 25
<212> TYPE: DNA
<213> ORGANISM: Artificial
<220> FEATURE:
<223> OTHER INFORMATION: antisense nucleotide

<400> SEQUENCE: 197
aacaucaagg aagauggcau uucua                                              25

<210> SEQ ID NO 198
<211> LENGTH: 25
<212> TYPE: DNA
<213> ORGANISM: Artificial
<220> FEATURE:
<223> OTHER INFORMATION: antisense nucleotide

<400> SEQUENCE: 198
acaucaagga agauggcauu ucuag                                              25

<210> SEQ ID NO 199
<211> LENGTH: 30
<212> TYPE: DNA
<213> ORGANISM: Artificial
<220> FEATURE:
<223> OTHER INFORMATION: antisense nucleotide

<400> SEQUENCE: 199
acaucaagga agauggcauu ucuaguuugg                                         30

<210> SEQ ID NO 200
<211> LENGTH: 25
<212> TYPE: DNA
<213> ORGANISM: Artificial
<220> FEATURE:
<223> OTHER INFORMATION: antisense nucleotide

<400> SEQUENCE: 200
acaucaagga agauggcauu ucuag                                              25

<210> SEQ ID NO 201
<211> LENGTH: 25
<212> TYPE: DNA
<213> ORGANISM: Artificial
<220> FEATURE:
<223> OTHER INFORMATION: antisense nucleotide

<400> SEQUENCE: 201
```
caucaaggaa gauggcauuu cuagu                                          25

<210> SEQ ID NO 202
<211> LENGTH: 25
<212> TYPE: DNA
<213> ORGANISM: Artificial
<220> FEATURE:
<223> OTHER INFORMATION: antisense nucleotide

<400> SEQUENCE: 202
aucaaggaag auggcauuuc uaguu                                          25

<210> SEQ ID NO 203
<211> LENGTH: 25
<212> TYPE: DNA
<213> ORGANISM: Artificial
<220> FEATURE:
<223> OTHER INFORMATION: antisense nucleotide

<400> SEQUENCE: 203
ucaaggaaga uggcauuucu aguuu                                          25

<210> SEQ ID NO 204
<211> LENGTH: 20
<212> TYPE: DNA
<213> ORGANISM: Artificial
<220> FEATURE:
<223> OTHER INFORMATION: antisense nucleotide

<400> SEQUENCE: 204
ucaaggaaga uggcauuucu                                                20

<210> SEQ ID NO 205
<211> LENGTH: 25
<212> TYPE: DNA
<213> ORGANISM: Artificial
<220> FEATURE:
<223> OTHER INFORMATION: antisense nucleotide

<400> SEQUENCE: 205
caaggaagau ggcauuucua guuug                                          25

<210> SEQ ID NO 206
<211> LENGTH: 25
<212> TYPE: DNA
<213> ORGANISM: Artificial
<220> FEATURE:
<223> OTHER INFORMATION: antisense nucleotide

<400> SEQUENCE: 206
aaggaagaug gcauuucuag uuugg                                          25

<210> SEQ ID NO 207
<211> LENGTH: 25
<212> TYPE: DNA
<213> ORGANISM: Artificial
<220> FEATURE:
<223> OTHER INFORMATION: antisense nucleotide

<400> SEQUENCE: 207
aggaagaugg cauuucuagu uugga                                          25

<210> SEQ ID NO 208
<211> LENGTH: 25
<212> TYPE: DNA
<213> ORGANISM: Artificial

```
-continued

<220> FEATURE:
<223> OTHER INFORMATION: antisense nucleotide

<400> SEQUENCE: 208
ggaagauggc auuucuaguu uggag                                    25

<210> SEQ ID NO 209
<211> LENGTH: 25
<212> TYPE: DNA
<213> ORGANISM: Artificial
<220> FEATURE:
<223> OTHER INFORMATION: antisense nucleotide

<400> SEQUENCE: 209
gaagauggca uuucuaguuu ggaga                                    25

<210> SEQ ID NO 210
<211> LENGTH: 25
<212> TYPE: DNA
<213> ORGANISM: Artificial
<220> FEATURE:
<223> OTHER INFORMATION: antisense nucleotide

<400> SEQUENCE: 210
aagauggcau uucuaguuug gagau                                    25

<210> SEQ ID NO 211
<211> LENGTH: 25
<212> TYPE: DNA
<213> ORGANISM: Artificial
<220> FEATURE:
<223> OTHER INFORMATION: antisense nucleotide

<400> SEQUENCE: 211
agauggcauu ucuaguuugg agaug                                    25

<210> SEQ ID NO 212
<211> LENGTH: 25
<212> TYPE: DNA
<213> ORGANISM: Artificial
<220> FEATURE:
<223> OTHER INFORMATION: antisense nucleotide

<400> SEQUENCE: 212
gauggcauuu cuaguuugga gaugg                                    25

<210> SEQ ID NO 213
<211> LENGTH: 25
<212> TYPE: DNA
<213> ORGANISM: Artificial
<220> FEATURE:
<223> OTHER INFORMATION: antisense nucleotide

<400> SEQUENCE: 213
auggcauuuc uaguuuggag auggc                                    25

<210> SEQ ID NO 214
<211> LENGTH: 25
<212> TYPE: DNA
<213> ORGANISM: Artificial
<220> FEATURE:
<223> OTHER INFORMATION: antisense nucleotide

<400> SEQUENCE: 214
uggcauuucu aguuuggaga uggca                                    25
```

```
<210> SEQ ID NO 215
<211> LENGTH: 25
<212> TYPE: DNA
<213> ORGANISM: Artificial
<220> FEATURE:
<223> OTHER INFORMATION: antisense nucleotide

<400> SEQUENCE: 215
ggcauuucua guuggagau ggcag                                                  25

<210> SEQ ID NO 216
<211> LENGTH: 25
<212> TYPE: DNA
<213> ORGANISM: Artificial
<220> FEATURE:
<223> OTHER INFORMATION: antisense nucleotide

<400> SEQUENCE: 216
gcauuucuag uuggagaug gcagu                                                  25

<210> SEQ ID NO 217
<211> LENGTH: 25
<212> TYPE: DNA
<213> ORGANISM: Artificial
<220> FEATURE:
<223> OTHER INFORMATION: antisense nucleotide

<400> SEQUENCE: 217
cauuucuagu uggagaugg caguu                                                  25

<210> SEQ ID NO 218
<211> LENGTH: 25
<212> TYPE: DNA
<213> ORGANISM: Artificial
<220> FEATURE:
<223> OTHER INFORMATION: antisense nucleotide

<400> SEQUENCE: 218
auuucuaguu uggagauggc aguuu                                                 25

<210> SEQ ID NO 219
<211> LENGTH: 25
<212> TYPE: DNA
<213> ORGANISM: Artificial
<220> FEATURE:
<223> OTHER INFORMATION: antisense nucleotide

<400> SEQUENCE: 219
uuucuaguuu ggagauggca guuuc                                                 25

<210> SEQ ID NO 220
<211> LENGTH: 25
<212> TYPE: DNA
<213> ORGANISM: Artificial
<220> FEATURE:
<223> OTHER INFORMATION: antisense nucleotide

<400> SEQUENCE: 220
uucuaguuug gagauggcag uuucc                                                 25

<210> SEQ ID NO 221
<211> LENGTH: 25
<212> TYPE: DNA
<213> ORGANISM: Artificial
<220> FEATURE:
<223> OTHER INFORMATION: antisense nucleotide
```

```
<400> SEQUENCE: 221
ccucuugauu gcuggucuug uuuuu                                          25

<210> SEQ ID NO 222
<211> LENGTH: 25
<212> TYPE: DNA
<213> ORGANISM: Artificial
<220> FEATURE:
<223> OTHER INFORMATION: antisense nucleotide

<400> SEQUENCE: 222
cucuugauug cuggucuugu uuuuc                                          25

<210> SEQ ID NO 223
<211> LENGTH: 25
<212> TYPE: DNA
<213> ORGANISM: Artificial
<220> FEATURE:
<223> OTHER INFORMATION: antisense nucleotide

<400> SEQUENCE: 223
ucuugauugc uggucuuguu uuuca                                          25

<210> SEQ ID NO 224
<211> LENGTH: 25
<212> TYPE: DNA
<213> ORGANISM: Artificial
<220> FEATURE:
<223> OTHER INFORMATION: antisense nucleotide

<400> SEQUENCE: 224
cuugauugcu ggucuuguuu ucaa                                           25

<210> SEQ ID NO 225
<211> LENGTH: 25
<212> TYPE: DNA
<213> ORGANISM: Artificial
<220> FEATURE:
<223> OTHER INFORMATION: antisense nucleotide

<400> SEQUENCE: 225
uugauugcug gucuuguuuu ucaaa                                          25

<210> SEQ ID NO 226
<211> LENGTH: 25
<212> TYPE: DNA
<213> ORGANISM: Artificial
<220> FEATURE:
<223> OTHER INFORMATION: antisense nucleotide

<400> SEQUENCE: 226
ugauugcugg ucuuguuuuu caaau                                          25

<210> SEQ ID NO 227
<211> LENGTH: 25
<212> TYPE: DNA
<213> ORGANISM: Artificial
<220> FEATURE:
<223> OTHER INFORMATION: antisense nucleotide

<400> SEQUENCE: 227
gauugcuggu cuuguuuuc aaauu                                           25

<210> SEQ ID NO 228
```

```
<211> LENGTH: 25
<212> TYPE: DNA
<213> ORGANISM: Artificial
<220> FEATURE:
<223> OTHER INFORMATION: antisense nucleotide

<400> SEQUENCE: 228 auugcgguc uuguuuuca aauuu                                               25

<210> SEQ ID NO 229
<211> LENGTH: 25
<212> TYPE: DNA
<213> ORGANISM: Artificial
<220> FEATURE:
<223> OTHER INFORMATION: antisense nucleotide

<400> SEQUENCE: 229
uugcuggucu uguuuucaa auuu                                               25

<210> SEQ ID NO 230
<211> LENGTH: 25
<212> TYPE: DNA
<213> ORGANISM: Artificial
<220> FEATURE:
<223> OTHER INFORMATION: antisense nucleotide

<400> SEQUENCE: 230
ugcuggucuu guuuucaaa uuuug                                              25

<210> SEQ ID NO 231
<211> LENGTH: 25
<212> TYPE: DNA
<213> ORGANISM: Artificial
<220> FEATURE:
<223> OTHER INFORMATION: antisense nucleotide

<400> SEQUENCE: 231
gcuggucuug uuuucaaau uuugg                                              25

<210> SEQ ID NO 232
<211> LENGTH: 25
<212> TYPE: DNA
<213> ORGANISM: Artificial
<220> FEATURE:
<223> OTHER INFORMATION: antisense nucleotide

<400> SEQUENCE: 232
cuggucuugu uuucaaauu uuggg                                              25

<210> SEQ ID NO 233
<211> LENGTH: 25
<212> TYPE: DNA
<213> ORGANISM: Artificial
<220> FEATURE:
<223> OTHER INFORMATION: antisense nucleotide

<400> SEQUENCE: 233
uggucuuguu uucaaauuu ugggc                                              25

<210> SEQ ID NO 234
<211> LENGTH: 25
<212> TYPE: DNA
<213> ORGANISM: Artificial
<220> FEATURE:
<223> OTHER INFORMATION: antisense nucleotide

<400> SEQUENCE: 234
``` ggcuuguuu uucaaauuuu gggca        25

<210> SEQ ID NO 235
<211> LENGTH: 25
<212> TYPE: DNA
<213> ORGANISM: Artificial
<220> FEATURE:
<223> OTHER INFORMATION: antisense nucleotide

<400> SEQUENCE: 235
gucuuguuuu ucaaauuuug gcag        25

<210> SEQ ID NO 236
<211> LENGTH: 25
<212> TYPE: DNA
<213> ORGANISM: Artificial
<220> FEATURE:
<223> OTHER INFORMATION: antisense nucleotide

<400> SEQUENCE: 236
ucuuguuuuu caaauuuugg gcagc        25

<210> SEQ ID NO 237
<211> LENGTH: 25
<212> TYPE: DNA
<213> ORGANISM: Artificial
<220> FEATURE:
<223> OTHER INFORMATION: antisense nucleotide

<400> SEQUENCE: 237 cuuguuuuc aaauuuggg cagcg        25

<210> SEQ ID NO 238
<211> LENGTH: 25
<212> TYPE: DNA
<213> ORGANISM: Artificial
<220> FEATURE:
<223> OTHER INFORMATION: antisense nucleotide

<400> SEQUENCE: 238 uuguuuuca aauuugggc agcgg        25

<210> SEQ ID NO 239
<211> LENGTH: 25
<212> TYPE: DNA
<213> ORGANISM: Artificial
<220> FEATURE:
<223> OTHER INFORMATION: antisense nucleotide

<400> SEQUENCE: 239 uguuuucaa auuugggca gcggu        25

<210> SEQ ID NO 240
<211> LENGTH: 25
<212> TYPE: DNA
<213> ORGANISM: Artificial
<220> FEATURE:
<223> OTHER INFORMATION: antisense nucleotide

<400> SEQUENCE: 240 guuuucaaa uuugggcag cggua        25

<210> SEQ ID NO 241
<211> LENGTH: 25
<212> TYPE: DNA

```
<213> ORGANISM: Artificial
<220> FEATURE:
<223> OTHER INFORMATION: antisense nucleotide

<400> SEQUENCE: 241
uuuuucaaau uugggcagc gguaa                                      25

<210> SEQ ID NO 242
<211> LENGTH: 25
<212> TYPE: DNA
<213> ORGANISM: Artificial
<220> FEATURE:
<223> OTHER INFORMATION: antisense nucleotide

<400> SEQUENCE: 242
uuuucaaauu uugggcagcg guaau                                     25

<210> SEQ ID NO 243
<211> LENGTH: 25
<212> TYPE: DNA
<213> ORGANISM: Artificial
<220> FEATURE:
<223> OTHER INFORMATION: antisense nucleotide

<400> SEQUENCE: 243
uuucaaauuu ugggcagcgg uaaug                                     25

<210> SEQ ID NO 244
<211> LENGTH: 25
<212> TYPE: DNA
<213> ORGANISM: Artificial
<220> FEATURE:
<223> OTHER INFORMATION: antisense nucleotide

<400> SEQUENCE: 244
uucaaauuuu gggcagcggu aauga                                     25

<210> SEQ ID NO 245
<211> LENGTH: 25
<212> TYPE: DNA
<213> ORGANISM: Artificial
<220> FEATURE:
<223> OTHER INFORMATION: antisense nucleotide

<400> SEQUENCE: 245
ucaaauuuug ggcagcggua augag                                     25

<210> SEQ ID NO 246
<211> LENGTH: 25
<212> TYPE: DNA
<213> ORGANISM: Artificial
<220> FEATURE:
<223> OTHER INFORMATION: antisense nucleotide

<400> SEQUENCE: 246
caaauuuugg gcagcgguaa ugagu                                     25

<210> SEQ ID NO 247
<211> LENGTH: 25
<212> TYPE: DNA
<213> ORGANISM: Artificial
<220> FEATURE:
<223> OTHER INFORMATION: antisense nucleotide

<400> SEQUENCE: 247
aaauuuuggg cagcgguaau gaguu                                     25
```

<210> SEQ ID NO 248
<211> LENGTH: 25
<212> TYPE: DNA
<213> ORGANISM: Artificial
<220> FEATURE:
<223> OTHER INFORMATION: antisense nucleotide

<400> SEQUENCE: 248 aauuugggc agcgguaaug aguuc					25

<210> SEQ ID NO 249
<211> LENGTH: 25
<212> TYPE: DNA
<213> ORGANISM: Artificial
<220> FEATURE:
<223> OTHER INFORMATION: antisense nucleotide

<400> SEQUENCE: 249 auuugggca gcgguaauga guucu					25

<210> SEQ ID NO 250
<211> LENGTH: 25
<212> TYPE: DNA
<213> ORGANISM: Artificial
<220> FEATURE:
<223> OTHER INFORMATION: antisense nucleotide

<400> SEQUENCE: 250
ccauuguguu gaauccuuua acauu					25

<210> SEQ ID NO 251
<211> LENGTH: 22
<212> TYPE: DNA
<213> ORGANISM: Artificial
<220> FEATURE:
<223> OTHER INFORMATION: antisense nucleotide

<400> SEQUENCE: 251
ccauuguguu gaauccuuua ac					22

<210> SEQ ID NO 252
<211> LENGTH: 20
<212> TYPE: DNA
<213> ORGANISM: Artificial
<220> FEATURE:
<223> OTHER INFORMATION: antisense nucleotide

<400> SEQUENCE: 252
auuguguuga auccuuuaac					20

<210> SEQ ID NO 253
<211> LENGTH: 20
<212> TYPE: DNA
<213> ORGANISM: Artificial
<220> FEATURE:
<223> OTHER INFORMATION: antisense nucleotide

<400> SEQUENCE: 253
ccugaccuaa gaccugcuca					20

<210> SEQ ID NO 254
<211> LENGTH: 25
<212> TYPE: DNA
<213> ORGANISM: Artificial
<220> FEATURE:

<223> OTHER INFORMATION: antisense nucleotide

<400> SEQUENCE: 254
cuuuuggauu gcaucuacug uauag					25

<210> SEQ ID NO 255
<211> LENGTH: 25
<212> TYPE: DNA
<213> ORGANISM: Artificial
<220> FEATURE:
<223> OTHER INFORMATION: antisense nucleotide

<400> SEQUENCE: 255
cauucaacug uugccuccgg uucug					25

<210> SEQ ID NO 256
<211> LENGTH: 24
<212> TYPE: DNA
<213> ORGANISM: Artificial
<220> FEATURE:
<223> OTHER INFORMATION: antisense nucleotide

<400> SEQUENCE: 256 cguugccuc cgguucugaa ggug					24

<210> SEQ ID NO 257
<211> LENGTH: 31
<212> TYPE: DNA
<213> ORGANISM: Artificial
<220> FEATURE:
<223> OTHER INFORMATION: antisense nucleotide

<400> SEQUENCE: 257
cauucaacug uugccuccgg uucugaaggu g				31

<210> SEQ ID NO 258
<211> LENGTH: 25
<212> TYPE: DNA
<213> ORGANISM: Artificial
<220> FEATURE:
<223> OTHER INFORMATION: antisense nucleotide

<400> SEQUENCE: 258
cugaaggugu ucuuguacuu caucc					25

<210> SEQ ID NO 259
<211> LENGTH: 27
<212> TYPE: DNA
<213> ORGANISM: Artificial
<220> FEATURE:
<223> OTHER INFORMATION: antisense nucleotide

<400> SEQUENCE: 259
uguauaggga cccuccuucc augacuc					27

<210> SEQ ID NO 260
<211> LENGTH: 20
<212> TYPE: DNA
<213> ORGANISM: Artificial
<220> FEATURE:
<223> OTHER INFORMATION: antisense nucleotide

<400> SEQUENCE: 260
aucccacuga uucugaauuc						20

```
<210> SEQ ID NO 261
<211> LENGTH: 22
<212> TYPE: DNA
<213> ORGANISM: Artificial
<220> FEATURE:
<223> OTHER INFORMATION: antisense nucleotide

<400> SEQUENCE: 261
uuggcucugg ccuguccuaa ga                                              22

<210> SEQ ID NO 262
<211> LENGTH: 35
<212> TYPE: DNA
<213> ORGANISM: Artificial
<220> FEATURE:
<223> OTHER INFORMATION: antisense nucleotide

<400> SEQUENCE: 262
aagaccugcu cagcuucuuc cuuagcuucc agcca                                35

<210> SEQ ID NO 263
<211> LENGTH: 20
<212> TYPE: DNA
<213> ORGANISM: Artificial
<220> FEATURE:
<223> OTHER INFORMATION: antisense nucleotide

<400> SEQUENCE: 263
ggagagagcu uccuguagcu                                                 20

<210> SEQ ID NO 264
<211> LENGTH: 23
<212> TYPE: DNA
<213> ORGANISM: Artificial
<220> FEATURE:
<223> OTHER INFORMATION: antisense nucleotide

<400> SEQUENCE: 264
ucacccuuuc cacaggcguu gca                                             23

<210> SEQ ID NO 265
<211> LENGTH: 32
<212> TYPE: DNA
<213> ORGANISM: Artificial
<220> FEATURE:
<223> OTHER INFORMATION: antisense nucleotide

<400> SEQUENCE: 265
ugcacuuugc aaugcugcug ucuucuugcu au                                   32

<210> SEQ ID NO 266
<211> LENGTH: 35
<212> TYPE: DNA
<213> ORGANISM: Artificial
<220> FEATURE:
<223> OTHER INFORMATION: antisense nucleotide

<400> SEQUENCE: 266
ucauaaugaa aacgccgcca uuucucaaca gaucu                                35

<210> SEQ ID NO 267
<211> LENGTH: 20
<212> TYPE: DNA
<213> ORGANISM: Artificial
<220> FEATURE:
<223> OTHER INFORMATION: antisense nucleotide
```

<400> SEQUENCE: 267
uuugugucuu ucugagaaac                                           20

<210> SEQ ID NO 268
<211> LENGTH: 30
<212> TYPE: DNA
<213> ORGANISM: Artificial
<220> FEATURE:
<223> OTHER INFORMATION: antisense nucleotide

<400> SEQUENCE: 268
uuuagcaugu ucccaauucu caggaauuug                                30

<210> SEQ ID NO 269
<211> LENGTH: 20
<212> TYPE: DNA
<213> ORGANISM: Artificial
<220> FEATURE:
<223> OTHER INFORMATION: antisense nucleotide

<400> SEQUENCE: 269
uccuguagaa uacuggcauc                                           20

<210> SEQ ID NO 270
<211> LENGTH: 27
<212> TYPE: DNA
<213> ORGANISM: Artificial
<220> FEATURE:
<223> OTHER INFORMATION: antisense nucleotide

<400> SEQUENCE: 270
ugcagaccuc cugccaccgc agauuca                                   27

<210> SEQ ID NO 271
<211> LENGTH: 34
<212> TYPE: DNA
<213> ORGANISM: Artificial
<220> FEATURE:
<223> OTHER INFORMATION: antisense nucleotide

<400> SEQUENCE: 271
uugcagaccu ccugccaccg cagauucagg cuuc                           34

<210> SEQ ID NO 272
<211> LENGTH: 20
<212> TYPE: DNA
<213> ORGANISM: Artificial
<220> FEATURE:
<223> OTHER INFORMATION: antisense nucleotide

<400> SEQUENCE: 272
uguuuuugag gauugcugaa                                           20

<210> SEQ ID NO 273
<211> LENGTH: 40
<212> TYPE: DNA
<213> ORGANISM: Artificial
<220> FEATURE:
<223> OTHER INFORMATION: antisense nucleotide

<400> SEQUENCE: 273
uguucugaca acaguuugcc gcugcccaau gccauccugg                     40

<210> SEQ ID NO 274
<211> LENGTH: 30

```
<212> TYPE: DNA
<213> ORGANISM: Artificial
<220> FEATURE:
<223> OTHER INFORMATION: antisense nucleotide

<400> SEQUENCE: 274
cucuuuucca gguucaagug ggauacuagc                                    30

<210> SEQ ID NO 275
<211> LENGTH: 31
<212> TYPE: DNA
<213> ORGANISM: Artificial
<220> FEATURE:
<223> OTHER INFORMATION: antisense nucleotide

<400> SEQUENCE: 275
caagcuuuuc uuuuaguugc ugcucuuuuc c                                  31

<210> SEQ ID NO 276
<211> LENGTH: 30
<212> TYPE: DNA
<213> ORGANISM: Artificial
<220> FEATURE:
<223> OTHER INFORMATION: antisense nucleotide

<400> SEQUENCE: 276
uauucuuuug uucuucuagc cuggagaaag                                    30

<210> SEQ ID NO 277
<211> LENGTH: 28
<212> TYPE: DNA
<213> ORGANISM: Artificial
<220> FEATURE:
<223> OTHER INFORMATION: antisense nucleotide

<400> SEQUENCE: 277
cugcuuccuc caaccauaaa acaaauuc                                      28

<210> SEQ ID NO 278
<211> LENGTH: 29
<212> TYPE: DNA
<213> ORGANISM: Artificial
<220> FEATURE:
<223> OTHER INFORMATION: antisense nucleotide

<400> SEQUENCE: 278
ccacucagag cucagaucuu cuaacuucc                                     29

<210> SEQ ID NO 279
<211> LENGTH: 27
<212> TYPE: DNA
<213> ORGANISM: Artificial
<220> FEATURE:
<223> OTHER INFORMATION: antisense nucleotide

<400> SEQUENCE: 279
cuuccacuca gagcucagau cuucuaa                                       27

<210> SEQ ID NO 280
<211> LENGTH: 30
<212> TYPE: DNA
<213> ORGANISM: Artificial
<220> FEATURE:
<223> OTHER INFORMATION: antisense nucleotide

<400> SEQUENCE: 280
```
caguccagga gcuaggucag gcugcuuugc                                    30

<210> SEQ ID NO 281
<211> LENGTH: 37
<212> TYPE: DNA
<213> ORGANISM: Artificial
<220> FEATURE:
<223> OTHER INFORMATION: antisense nucleotide

<400> SEQUENCE: 281
ucuugaagua aacgguuuac cgccuuccac ucagagc                            37

<210> SEQ ID NO 282
<211> LENGTH: 30
<212> TYPE: DNA
<213> ORGANISM: Artificial
<220> FEATURE:
<223> OTHER INFORMATION: antisense nucleotide

<400> SEQUENCE: 282
uccaacuggg gacgccucug uuccaaaucc                                    30

<210> SEQ ID NO 283
<211> LENGTH: 21
<212> TYPE: DNA
<213> ORGANISM: Artificial
<220> FEATURE:
<223> OTHER INFORMATION: antisense nucleotide

<400> SEQUENCE: 283
acuggggacg ccucuguucc a                                             21

<210> SEQ ID NO 284
<211> LENGTH: 20
<212> TYPE: DNA
<213> ORGANISM: Artificial
<220> FEATURE:
<223> OTHER INFORMATION: antisense nucleotide

<400> SEQUENCE: 284
ccguaaugau uguucuagcc                                               20

<210> SEQ ID NO 285
<211> LENGTH: 25
<212> TYPE: DNA
<213> ORGANISM: Artificial
<220> FEATURE:
<223> OTHER INFORMATION: antisense nucleotide

<400> SEQUENCE: 285
uuuugggcag cgguaaugag uucuu                                         25

<210> SEQ ID NO 286
<211> LENGTH: 25
<212> TYPE: DNA
<213> ORGANISM: Artificial
<220> FEATURE:
<223> OTHER INFORMATION: antisense nucleotide

<400> SEQUENCE: 286
uuugggcagc gguaaugagu ucuuc                                         25

<210> SEQ ID NO 287
<211> LENGTH: 25
<212> TYPE: DNA
<213> ORGANISM: Artificial

```
<220> FEATURE:
<223> OTHER INFORMATION: antisense nucleotide

<400> SEQUENCE: 287
uugggcagcg guaaugaguu cuucc                                          25

<210> SEQ ID NO 288
<211> LENGTH: 25
<212> TYPE: DNA
<213> ORGANISM: Artificial
<220> FEATURE:
<223> OTHER INFORMATION: antisense nucleotide

<400> SEQUENCE: 288
ugggcagcgg uaaugaguuc uucca                                          25

<210> SEQ ID NO 289
<211> LENGTH: 25
<212> TYPE: DNA
<213> ORGANISM: Artificial
<220> FEATURE:
<223> OTHER INFORMATION: antisense nucleotide

<400> SEQUENCE: 289
gggcagcggu aaugaguucu uccaa                                          25

<210> SEQ ID NO 290
<211> LENGTH: 25
<212> TYPE: DNA
<213> ORGANISM: Artificial
<220> FEATURE:
<223> OTHER INFORMATION: antisense nucleotide

<400> SEQUENCE: 290
ggcagcggua augaguucuu ccaac                                          25

<210> SEQ ID NO 291
<211> LENGTH: 25
<212> TYPE: DNA
<213> ORGANISM: Artificial
<220> FEATURE:
<223> OTHER INFORMATION: antisense nucleotide

<400> SEQUENCE: 291
gcagcgguaa ugaguucuuc caacu                                          25

<210> SEQ ID NO 292
<211> LENGTH: 25
<212> TYPE: DNA
<213> ORGANISM: Artificial
<220> FEATURE:
<223> OTHER INFORMATION: antisense nucleotide

<400> SEQUENCE: 292
cagcgguaau gaguucuucc aacug                                          25

<210> SEQ ID NO 293
<211> LENGTH: 25
<212> TYPE: DNA
<213> ORGANISM: Artificial
<220> FEATURE:
<223> OTHER INFORMATION: antisense nucleotide

<400> SEQUENCE: 293
agcgguaaug aguucuucca acugg                                          25
```

```
<210> SEQ ID NO 294
<211> LENGTH: 25
<212> TYPE: DNA
<213> ORGANISM: Artificial
<220> FEATURE:
<223> OTHER INFORMATION: antisense nucleotide

<400> SEQUENCE: 294
gcgguaauga guucuuccaa cuggg                                              25

<210> SEQ ID NO 295
<211> LENGTH: 25
<212> TYPE: DNA
<213> ORGANISM: Artificial
<220> FEATURE:
<223> OTHER INFORMATION: antisense nucleotide

<400> SEQUENCE: 295
cgguaaugag uucuuccaac ugggg                                              25

<210> SEQ ID NO 296
<211> LENGTH: 25
<212> TYPE: DNA
<213> ORGANISM: Artificial
<220> FEATURE:
<223> OTHER INFORMATION: antisense nucleotide

<400> SEQUENCE: 296
gguaaugagu ucuuccaacu gggga                                              25

<210> SEQ ID NO 297
<211> LENGTH: 25
<212> TYPE: DNA
<213> ORGANISM: Artificial
<220> FEATURE:
<223> OTHER INFORMATION: antisense nucleotide

<400> SEQUENCE: 297
guaaugaguu cuuccaacug gggac                                              25

<210> SEQ ID NO 298
<211> LENGTH: 25
<212> TYPE: DNA
<213> ORGANISM: Artificial
<220> FEATURE:
<223> OTHER INFORMATION: antisense nucleotide

<400> SEQUENCE: 298
uaaugaguuc uuccaacugg ggacg                                              25

<210> SEQ ID NO 299
<211> LENGTH: 25
<212> TYPE: DNA
<213> ORGANISM: Artificial
<220> FEATURE:
<223> OTHER INFORMATION: antisense nucleotide

<400> SEQUENCE: 299
aaugaguucu uccaacuggg gacgc                                              25

<210> SEQ ID NO 300
<211> LENGTH: 25
<212> TYPE: DNA
<213> ORGANISM: Artificial
<220> FEATURE:
<223> OTHER INFORMATION: antisense nucleotide
```

```
<400> SEQUENCE: 300
augaguucuu ccaacugggg acgcc                                          25

<210> SEQ ID NO 301
<211> LENGTH: 25
<212> TYPE: DNA
<213> ORGANISM: Artificial
<220> FEATURE:
<223> OTHER INFORMATION: antisense nucleotide

<400> SEQUENCE: 301
ugaguucuuc caacugggga cgccu                                          25

<210> SEQ ID NO 302
<211> LENGTH: 25
<212> TYPE: DNA
<213> ORGANISM: Artificial
<220> FEATURE:
<223> OTHER INFORMATION: antisense nucleotide

<400> SEQUENCE: 302
gaguucuucc aacugggac gccuc                                           25

<210> SEQ ID NO 303
<211> LENGTH: 25
<212> TYPE: DNA
<213> ORGANISM: Artificial
<220> FEATURE:
<223> OTHER INFORMATION: antisense nucleotide

<400> SEQUENCE: 303
aguucuucca acugggacg ccucu                                           25

<210> SEQ ID NO 304
<211> LENGTH: 25
<212> TYPE: DNA
<213> ORGANISM: Artificial
<220> FEATURE:
<223> OTHER INFORMATION: antisense nucleotide

<400> SEQUENCE: 304
guucuuccaa cugggacgc cucug                                           25

<210> SEQ ID NO 305
<211> LENGTH: 25
<212> TYPE: DNA
<213> ORGANISM: Artificial
<220> FEATURE:
<223> OTHER INFORMATION: antisense nucleotide

<400> SEQUENCE: 305
uucuuccaac uggggacgcc ucugu                                          25

<210> SEQ ID NO 306
<211> LENGTH: 25
<212> TYPE: DNA
<213> ORGANISM: Artificial
<220> FEATURE:
<223> OTHER INFORMATION: antisense nucleotide

<400> SEQUENCE: 306
ucuuccaacu ggggacgccu cuguu                                          25

<210> SEQ ID NO 307
```

```
<211> LENGTH: 25
<212> TYPE: DNA
<213> ORGANISM: Artificial
<220> FEATURE:
<223> OTHER INFORMATION: antisense nucleotide

<400> SEQUENCE: 307
cuuccaacug gggacgccuc uguuc                                           25

<210> SEQ ID NO 308
<211> LENGTH: 25
<212> TYPE: DNA
<213> ORGANISM: Artificial
<220> FEATURE:
<223> OTHER INFORMATION: antisense nucleotide

<400> SEQUENCE: 308
uuccaacugg ggacgccucu guucc                                           25

<210> SEQ ID NO 309
<211> LENGTH: 20
<212> TYPE: DNA
<213> ORGANISM: Artificial
<220> FEATURE:
<223> OTHER INFORMATION: antisense nucleotide

<400> SEQUENCE: 309
gauugcuggu cuuguuuuuc                                                 20

<210> SEQ ID NO 310
<211> LENGTH: 20
<212> TYPE: DNA
<213> ORGANISM: Artificial
<220> FEATURE:
<223> OTHER INFORMATION: antisense nucleotide

<400> SEQUENCE: 310
ccucuugauu gcuggucuug                                                 20

<210> SEQ ID NO 311
<211> LENGTH: 22
<212> TYPE: DNA
<213> ORGANISM: Artificial
<220> FEATURE:
<223> OTHER INFORMATION: antisense nucleotide

<400> SEQUENCE: 311
gguaaugagu ucuuccaacu gg                                              22

<210> SEQ ID NO 312
<211> LENGTH: 20
<212> TYPE: DNA
<213> ORGANISM: Artificial
<220> FEATURE:
<223> OTHER INFORMATION: antisense nucleotide

<400> SEQUENCE: 312 acugggacg ccucuguucc                                                  20

<210> SEQ ID NO 313
<211> LENGTH: 20
<212> TYPE: DNA
<213> ORGANISM: Artificial
<220> FEATURE:
<223> OTHER INFORMATION: PRO 51

<400> SEQUENCE: 313
```

```
ucaaggaaga uggcauuucu                                                   20

<210> SEQ ID NO 314
<211> LENGTH: 20
<212> TYPE: DNA
<213> ORGANISM: Artificial
<220> FEATURE:
<223> OTHER INFORMATION: PS 49

<400> SEQUENCE: 314
ggccaaaccu cggcuuaccu                                                   20
```